(12) United States Patent
Kamen et al.

(10) Patent No.: US 9,402,987 B2
(45) Date of Patent: Aug. 2, 2016

(54) DEVICES AND METHODS FOR OCCLUDING A FLEXIBLE TUBE

(71) Applicant: DEKA Products Limited Partnership, Manchester, NH (US)

(72) Inventors: Dean Kamen, Bedford, NH (US); Rodney S. Kenley, Libertyville, IL (US); Kevin L. Grant, Litchfield, NH (US); Larry B. Gray, Merrimack, NH (US); Jason A. Demers, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 14/617,173

(22) Filed: Feb. 9, 2015

(65) Prior Publication Data

US 2015/0151105 A1 Jun. 4, 2015

Related U.S. Application Data

(63) Continuation of application No. 12/714,056, filed on Feb. 26, 2010, now Pat. No. 8,950,728.

(60) Provisional application No. 61/158,174, filed on Mar. 6, 2009.

(51) Int. Cl.
 *A61M 39/28* (2006.01)
 *F16K 7/06* (2006.01)

(52) U.S. Cl.
 CPC ............... *A61M 39/281* (2013.01); *F16K 7/06* (2013.01); *F16K 7/063* (2013.01)

(58) Field of Classification Search
 USPC ................................................ 251/4, 8, 9
 See application file for complete search history.

(56) References Cited

U.S. PATENT DOCUMENTS

| | | | | |
|---|---|---|---|---|
| 3,254,869 A * | 6/1966 | Easey | ................... | A61M 39/28 222/507 |
| 5,257,978 A * | 11/1993 | Haber | ................. | A61M 39/281 251/9 |
| 5,704,584 A * | 1/1998 | Winterer | ............ | A61M 39/286 251/7 |
| 5,826,621 A * | 10/1998 | Jemmott | ........... | A61M 5/16831 137/853 |
| 5,954,485 A * | 9/1999 | Johnson | ............ | A61M 5/16831 417/474 |
| 6,203,528 B1 * | 3/2001 | Deckert | ................ | A61M 5/142 604/131 |
| 6,659,976 B2 * | 12/2003 | Beck | ................. | A61M 5/14232 604/118 |
| 7,540,859 B2 * | 6/2009 | Claude | ................ | A61M 1/3655 251/4 |
| 2004/0220542 A1 * | 11/2004 | Cise | ........................ | A61M 5/142 604/500 |
| 2007/0265559 A1 * | 11/2007 | Kunishige | ........... | A61M 39/281 604/7 |
| 2007/0269324 A1 * | 11/2007 | Goldor | .............. | A61M 5/14228 417/474 |
| 2009/0221964 A1 * | 9/2009 | Rotem | .............. | A61M 5/14228 604/151 |
| 2009/0306592 A1 * | 12/2009 | Kasai | ................ | A61M 5/14228 604/131 |
| 2011/0313358 A1 * | 12/2011 | Hariharesan | ...... | A61M 5/14228 604/151 |

* cited by examiner

*Primary Examiner* — Kevin Murphy
*Assistant Examiner* — Jonathan Waddy
(74) *Attorney, Agent, or Firm* — Marc J. Gorayeb

(57) ABSTRACT

A device for occluding a flexible tube comprising a first body frictionally connected to a second body by a spring-loaded clip. A flexible tube having a first end and a second end is secured in a bent position to each body by a plurality of clamps. When the two bodies are separated by a predetermined threshold force acting axially on either the first end or second end of the tube so as to cause the bent section of tubing to straighten, the spring-load clip occludes the tube secured by the second body.

9 Claims, 53 Drawing Sheets

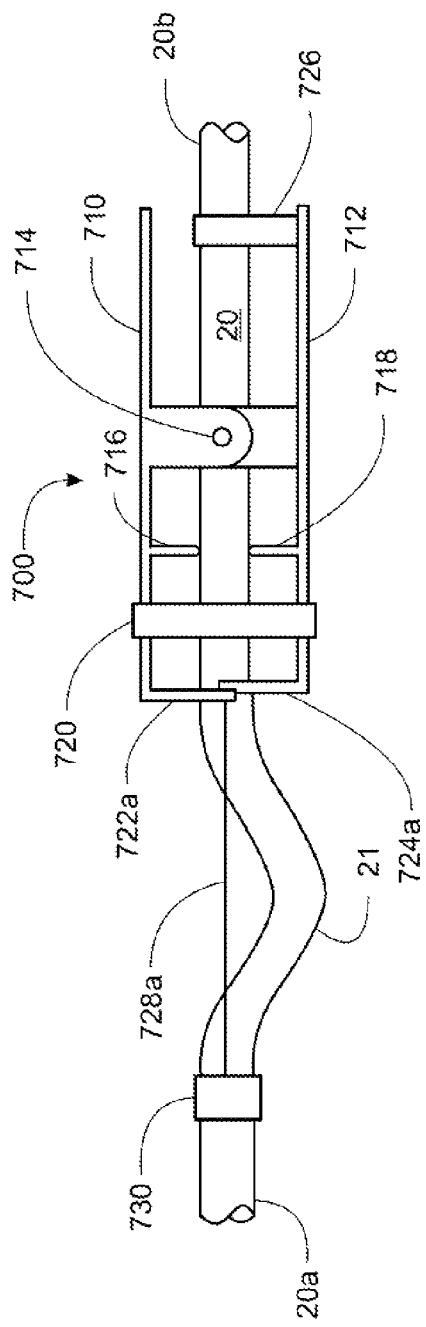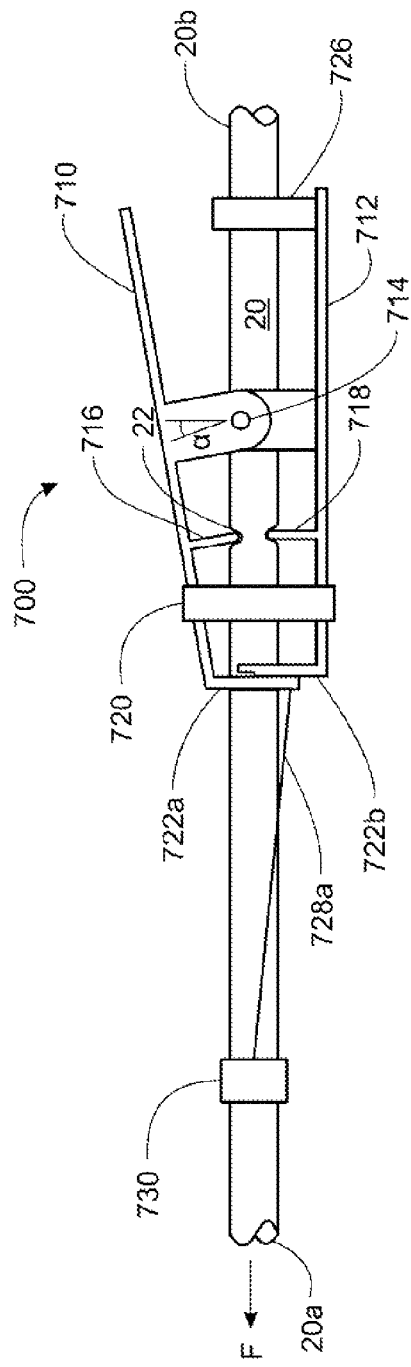

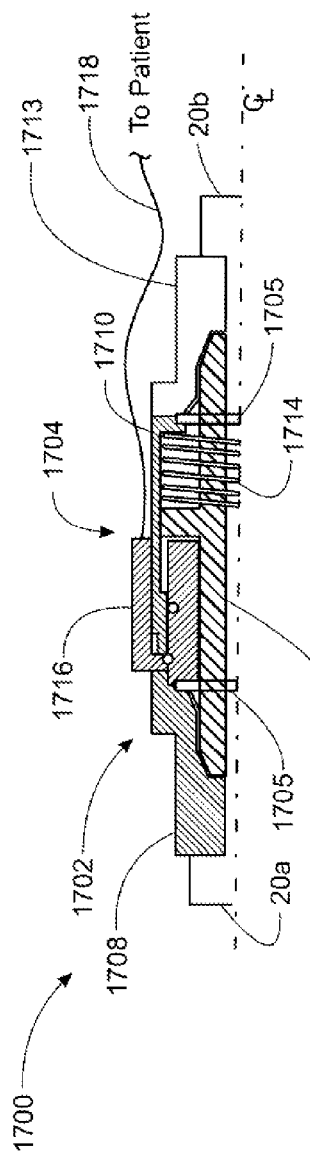
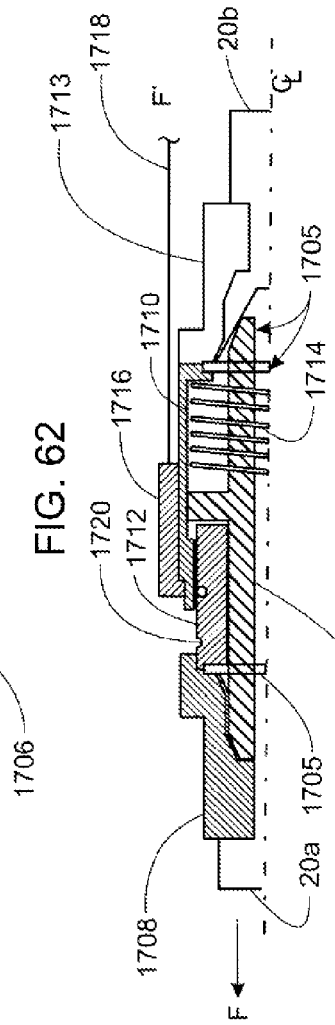
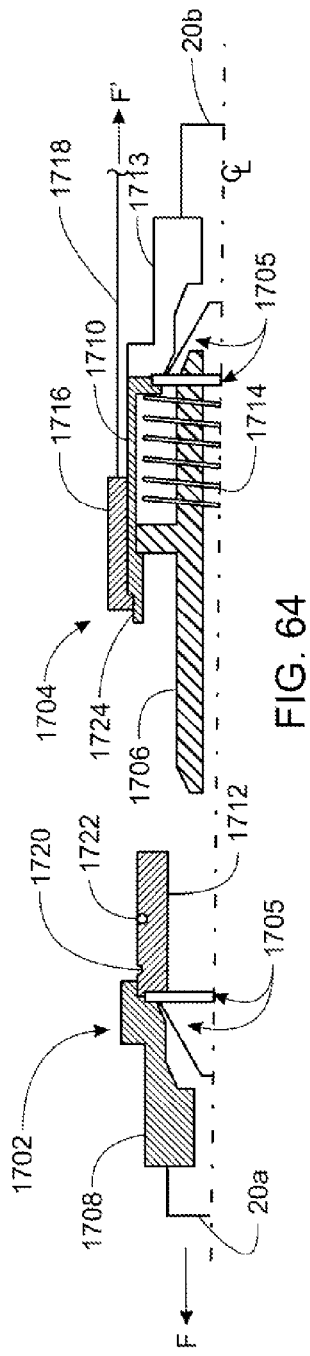

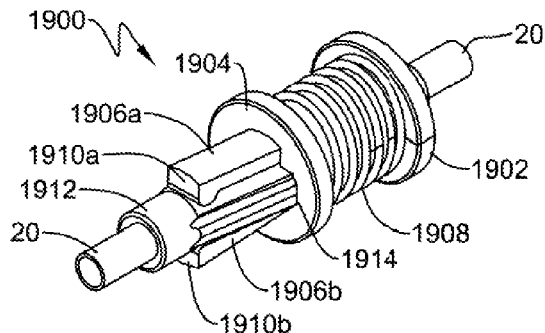
FIG. 71
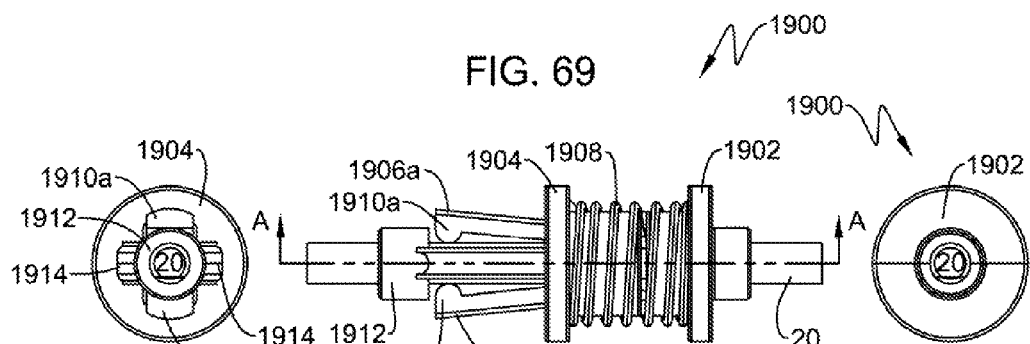
FIG. 69
FIG. 75  FIG. 76
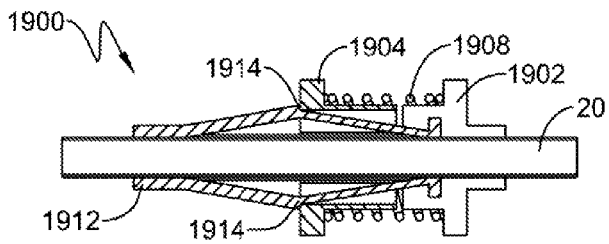
FIG. 70

DEVICES AND METHODS FOR OCCLUDING A FLEXIBLE TUBE

RELATED APPLICATIONS

This application is a continuation application of U.S. patent application Ser. No. 12/714,056, filed Feb. 26, 2010 and entitled Devices and Methods for Occluding a Flexible Tube, now U.S. Pat. No. 8,950,728, issued, Feb. 10, 2015 which claims priority to U.S. Provisional Patent Application Ser. No. 61/158,174, filed Mar. 6, 2009, and entitled Device and Method for Occluding a Flexible Tube, which is incorporated by reference herein in its entirety.

FIELD OF THE INVENTION

The invention relates to devices and methods for occluding or constricting the lumen of a segment of flexible tubing by compressing the wall of the tubing. In an exemplary application, it relates to the partial or complete occlusion of flexible tubing in fluid communication with the blood vessel of a patient.

BACKGROUND

Systems that use flexible tubes to transfer fluids from one location to another frequently take advantage of the compressibility of the tubes to adjust, restrict or stop fluid flow within them. This is particularly useful in medical applications in which biological or therapeutic fluids are transferred between a source or destination and a patient by means of an electro-mechanical instrument. In hemodialysis, for example, blood is pumped from a patient's body through a dialyzer to remove wastes and excess fluid from the blood. Blood is removed from the patient, pumped through the dialyzer, and then returned back to the patient in a closed-loop system. External blood loss can occur if the intravenous (IV) needle (e.g. a fistula needle) returning the treated blood is removed or dislodged from the patient's body and the blood pump is not stopped in a timely manner. Generally, a dislodgement of an arterial needle or catheter (in which blood is being drawn to the machine from the patient) can be readily detected by the machine's air-in-line detectors. It is much more difficult, however, to detect dislodgement of a venous needle or catheter. This risk is heightened when a patient is asleep or otherwise unaware that tension applied to the intravenous line has resulted in dislodgement of the IV needle. Current dialysis systems cannot readily detect when an indwelling venous IV needle delivering blood from the dialysis machine to the patient has become dislodged from the patient's body. However, such machines can detect an increase in the back-pressure on the pump discharge line, typically from an occlusion or kink in the blood tubing downstream of the pump, which can trigger an alarm and pump shutdown. A device that can compress the flexible tubing transporting fluid to the patient can provide the necessary increase in intraluminal pressure, or possibly even provide complete occlusion, that can prevent excessive fluid loss from a dislodged catheter. The problem is how a threatened intravascular catheter dislodgement can be made to trigger such an occluding device.

It is therefore an object of this invention to provide a device to occlude any flexible tubing carrying a fluid, in which the device can be triggered by the application of a pulling or traction force on a segment of the flexible tubing, the pulling force being sufficient to cause movement of the tubing (if there is slack in the tubing) or elastic stretching of the tubing (if there is no slack in the tubing). In medical applications, such as, for example hemodialysis applications, either the blood tubing connected to the dialyzer or the tubing connected to the intravascular catheter or needle can serve as such a segment of flexible tubing. When a predetermined threshold amount of pulling force occurs along a segment of the tubing between the blood pump and the IV needle, a portion of that segment of tubing will either move or stretch in an amount sufficient to trigger an attached occluding device. The threshold tension required to trigger the device can be set to be less than the force that could cause dislodgement of an indwelling needle or catheter assembly that has been taped to a person's arm or other part of the body. Since dialysis machines are generally programmed to detect an occlusion on the pump discharge tubing, the invention can be easily integrated into an existing dialysis system by locating the occluder on the tubing between the blood pump and the IV needle, thus reducing the risk of accidental exsanguination.

SUMMARY

The present invention is directed to a device and method for occluding or constricting the lumen of a segment of a flexible tube. In some applications, such a device will help prevent accidental blood loss by occluding flexible tubing coupled to an intravenous catheter or needle. The occlusion can be partial or complete. In either case, the increase in flow resistance or change in intraluminal pressure can be detected by appropriate sensors in the fluid line, resulting in the generation of a pump controller alarm and a pump shutdown signal. A device having features of the present invention comprises generally an occluder assembly having an actuator constructed and positioned to cause one or more occluding elements to act on the walls of the flexible tube. The actuator functions when a predetermined threshold amount of pulling force along the length of a segment of the tube causes a portion of the segment of tube to move or to stretch slightly. Certain embodiments of the present invention provide a device and method for constricting the lumen of a segment of flexible tube a portion of which is moved or stretched in response to a pulling force being applied to the tube.

In an embodiment, the device includes a grip for holding a segment of a flexible tube, at least one occluder under an elastic force urging the occluder to compress a flexible tube held by the grip, and at least one occluder stop connected to or comprising the grip to engage and block the occluder from moving under influence of the elastic force. Movement of the grip in response to a pulling force on a segment of flexible tube being held by the grip can disengage the occluder stop from the occluder, releasing the occluder to compress the tube.

The device can also include a frame for holding a segment of flexible tubing, the frame having a first end and a second end, the first end connected to or comprising the grip, wherein the occluder is movably connected to the frame near the second end of the frame.

The device can also include an arm having an occluding end and a connecting end, the connecting end being slidably connected to the frame near the second end. The occluding end can have a surface for engaging the occluder stop and an occluding element adapted to compress a segment of flexible tube held by the grip, such that movement of the grip away from the occluder causes disengagement of the occluder stop from the occluding end of the occluder.

The occluder can also be pivotally mounted near the second end of the frame to a base unit, the base unit being slidably mounted to the frame, so that disengagement of the occluder stop from the occluder causes movement of the frame away from the base unit.

The base unit can have a first end and a second end, the occluder being mounted to the base unit near the first end of the base unit; and a second grip can be attached to the second end of the base unit.

The device can also have an actuator that is slidably mounted to the frame between the base unit and the first end of the frame, the actuator contacting the arm of the occluder and urging the occluding element toward a tube on the frame as the actuator slides toward the first end of the frame.

An actuator spring can be mounted between the actuator and the base unit, the actuator spring urging the actuator to move away from the base unit and toward the first end of the frame, the actuator then being able to actuate the occluder upon disengagement of the occluder from the occluder stop.

The actuator arm can have a jog feature is included on the actuator arm against which the actuator can be positioned when the occluder is in contact with the occluder stop.

The frame can further comprise a triggering spring compressible by the base unit, wherein the occluder can be actuated upon the application of a pulling force on a tube being held by the grip, the pulling force being sufficient to compress the triggering spring and cause movement of the frame away from the base unit.

The base unit can further comprise a dowel disposed in a slot near the second end of the frame, wherein movement of the dowel within the slot causes contact between the dowel and the triggering spring.

The grip can have a channel in which a segment of flexible tubing can be positioned, the surface of the channel having raised features such as ridges, ribs, cross hatches, or scales; and a second latch can be hingedly mounted on the second grip, the second latch being closeable over the channel.

In a further embodiment, the device can have a mounting pad for mounting the base unit, frame and occluder to a surface such as a person's body, the mounting pad connectable to the base unit and having one or more extensions to which tape or adhesive can be applied to secure the mounting pad to the surface.

The mounting pad can be pivotably connectable to the base unit, allowing the base unit, frame and occluder to rotate in a plane that is generally parallel to the surface on which the mounting pad is mounted.

The mounting pad can be slidably connectable to the base unit. The mounting pad can also be attachable to a member, the member slidably connected to the base unit through a slot of the base unit, and disposed within a recess of the frame, wherein a pulling force on a segment of tubing held by the second grip causes the member to contact a wall of the recess, urging the frame to move away from the base unit and the occluder stop to disengage from the occluder.

The frame can include a post, the post being capable of contacting a pair of cams on the mounting pad, wherein rotation of the frame in a first direction can cause contact between the post and a first cam, and rotation of the frame in a second direction can cause contact between the post and a second cam, and either contact creating a force to urge the frame to move away from the base unit and the occluder stop to disengage from the occluder.

In another embodiment, the device can comprise two or more occluders, and the at least one occluder stop comprises two or more occluder stops. In some embodiments, the pulling force on the tube comprises stretching of at least a segment of the tube.

Another aspect of the present invention includes an occluder having an elastic force actuating member (e.g. torsion spring, leaf spring, elastic band). The elastic member remains in a compressed or tensioned position until a threshold force triggers the elastic member to move the occluder from a first position to a second position causing fluid flow within the flexible tubing to be restricted.

In another embodiment of the present invention, the occluder includes a tapered housing having two openings where a flexible tube may enter and exit the housing. The housing also encloses a cylindrical body which may engage the tube. The housing is tapered allowing the body to pinch the tube against an interior wall as the tube moves toward the tapered end of the housing.

In another embodiment of the present invention, a single coil of flexible tubing is enclosed by a cylindrical housing having a first opening and a second opening along a circumferential edge. The tube enters the housing at the first opening and exits the housing at the second opening. The tube occludes itself by kinking when the flexible tube is exposed to a predetermined threshold force between the first and second openings of the housing.

In another embodiment of the present invention, the flexible tube is releasably attached to the occluder at a first location and restrained between two cylindrical bodies rotatably connected to the occluder. As the tubes move from a first position to a second position, the bodies rotate towards each other and apply a generally equal and opposite pinching force on the tube capable of occluding the tube.

In another embodiment of the present invention, a single coil of flexible tubing is enclosed by a cylindrical housing. An occluding edge is located along an interior loop of the enclosed coil whereby the tube is occluded along the edge when a predetermined threshold force is applied along the tube.

In another embodiment of the present invention, the device includes a first body having a pair of support arms pivotably attached to the body. The flexible tube is demountable attached to the support arms. A second body having an occluding edge perpendicular to the tube is pivotably attached to a hinge on the first body. A spring abuts the first and second body in order to provide the necessary force to occlude the tube when a threshold tensional force acts on the tube. The force moves the support arms into a second position, whereby the spring-loaded body occluded the tube along the occluding edge.

In another embodiment of the present invention, the device includes a body having a pair of support arms pivotably attached to the body. A flexible tube to be occluded is releasably attached to the support arms. A plunger is slideably attached to the body and a spring is compressed between the body and plunger. A notch near the distal end of the plunger temporarily engages one of the support arms. The plunger is triggered into a second position when the support arms rotate away from each other. The spring then provides a compressive force necessary to occlude the flexible tube.

In another embodiment of the invention, the device includes a first body and a second body pivotably attached at a central hinge. An occluding tab engages a flexible tube releasably attached to the first body by a pair of clips. A spring provides a compressive force necessary to rotate the occluding tab about the central hinge to occlude the flexible tube. The bodies are held in a first position by locking engagement of a retaining tab mounted on the bottom surface of the second body near the spring. The restraining tab extends away from the second body and lockingly engages the first body at a flexible arm. A rod extends outwardly and away from the flexible arm where a clip is attached to the distal end of the rod. The tube is releasably attached to the clip. A predetermined threshold amount a force along the flexible tube moves the flexible arm from a first position to a second position thus disengaging the restraining tab from the flexible arm, activating the spring, and occluding the flexible tube through the occluding tab.

In another embodiment of the invention, the device includes a housing which positions the flexible tubing into an s-shaped configuration without any restriction of flow within the tube. As one end of the tube is pulled by a predetermined force outwardly and away from the housing, the tube in the housing is occluded.

In another embodiment of the invention, the device includes a tab slideably attached to a first body. A flexible tube is releasably attached to the tab and the first body. As a predetermined force pulls on the flexible tube, the tab slides outwardly and away from the first body, thus triggers a second body to occlude the tube. An occluding edge, located along a bottom surface of the second body, normally rests on the tab but occludes the tube when the tube moves from a first position to a second position.

In additional embodiments of the invention, the device includes a cylindrical tube having a tapered first end and a tapered second end. The first end is inserted into a first valve wherein the tube creates an open flow path through the first valve. The second end is inserted into a second valve wherein the tube creates an open flow path through the second valve. The first and second valves are located in a female and male coupling respectively. A compression spring is also housed within the couplings while engaged. When the couplings are brought into locking engagement the spring is compressed and the tapered ends of the tube penetrate the first and second valves to create a continuous flow path between a first and second flexible tube. A predetermined threshold amount of tension acting on the distal end of a least one of the tubes disengages couplings allowing the compression spring to expand and separate the couplings from locking engagement with each other. As the spring expands the tube is withdrawn from both the first and second valves, whereby any flow between the flexible tubes is blocked.

In some methods of the invention, the method can include the steps of: providing an occluder having a force actuating element; mounting the occluder to the flexible tube having a first end and a second end; applying a tensional force along a central axis of the flexible tube between the first end and the second end wherein the flexible tube moves relative to the occluder; and occluding the flexible tube using the force actuating element in combination with the occluder.

A typical method for occluding a flexible tube as embodied in this invention generally comprises the steps of: providing an occluding device having an occluding member; coupling the device to a flexible tube to be occluded; applying a predetermined threshold amount of tension to one end of the tubing; triggering the occluding member to occlude the tube.

Another method for occluding a flexible tube as embodied in this invention generally comprises the steps of: providing a device having an elastic actuating member and an occluding member; coupling the device to a flexible tube to be occluded; applying a predetermined threshold amount of tension to the tubing; triggering the elastic actuating member; occluding the tube with the occluding member.

Another method includes arming an occluding device, the occluding device comprising a grip for holding a segment of the tube, an occluder under an elastic force urging the occluder to compress the flexible tube held by the grip, and an occluder stop connected to the grip to block the occluder from moving under influence of the elastic force, the method comprising: moving the occluder to engage the occluder with the occluder stop, positioning the tube next to the occluder, and securing a segment of the tube to the grip.

In an additional embodiment, the occluding device can further comprise a frame for holding a segment of flexible tubing and having a first end connected to or comprising the grip and a second end, a base unit slidably mounted to the frame near the second end, an actuator slidably mounted to the frame between the base unit and the first end, and an actuator spring mounted between the actuator and the base unit, wherein the occluder comprises an arm that makes contact with the actuator and has an occluding end and a connecting end, the occluding end having a surface for engaging the occluder stop and the connecting end pivotably mounted to the base unit, wherein movement of the actuator toward the first end of the frame causes the occluder to pivot toward the segment of tube, the method of engaging the occluder with the occluder stop further comprising: moving the actuator toward the base unit while compressing the actuator spring, moving the occluder stop toward the occluding end of the occluder, and pivoting the occluder to engage the occluding end of the occluder with the occluder stop.

In another embodiment, a method of constricting the lumen of a flexible tube includes using an occluding device comprising a grip for holding a segment of the tube, an occluder under an elastic force urging the occluder to compress the tube, and an occluder stop connected to the grip to block the occluder from moving under influence of the elastic force, the method comprising: securing a segment of tube to the grip, positioning the tube next to the occluder, applying a pulling force on the tube near the grip, disengaging the occluder stop from the occluder, and releasing the occluder to compress the tube. The device can further comprise a frame for holding a segment of the tube and having a first end and a second end, the first end connected to or comprising the grip, wherein the occluder comprises an arm having an occluding end and a connecting end, the connecting end being slidably connected to the frame near the second end, and the occluding end having a surface for engaging the occluder stop and an occluding element for compressing the tube, and wherein applying a pulling force on the tube near the grip further comprises the method of increasing the distance between the grip and the occluder. The device can further comprise a base unit slidably mounted to the frame near the second end, an actuator slidably mounted to the frame between the base unit and the first end, and an actuator spring mounted between the actuator and the base unit, the occluder arm making contact with the actuator and the connecting end of the occluder being pivotably mounted to the base unit, wherein releasing the occluder further comprises the method of releasing the actuator to move toward the first end under influence of the actuator spring, and allowing the actuator to slide along the occluder arm, causing the occluder arm to pivot toward the tube.

Still another method for occluding a flexible tube as embodied in this invention generally comprises the steps of: providing a normally-closed valve at each end of two tubes to be hydraulically connected; establishing fluid communication between the two tubes by inserting a hollow cylinder into the body of each valve; compressing a spring between the two valves; restraining the cylinder using a male and female coupling; applying a predetermined threshold axial force along at least one of the tubes; disengaging the male and female couplings; urging the coupling apart using the spring; and closing both valves.

Another aspect of the present invention provides a method for occluding a flexible tube. The method includes the steps of: providing a normally-closed valve at each end of two tubes to be hydraulically connected; establishing fluid communication between the two tubes by inserting a hollow cylinder into the body of each valve; compressing a spring between the two valves; restraining the cylinder using a male and female coupling; applying a predetermined axial force along at least one of the tubes; disengaging the male and female couplings; urging the coupling apart using the spring; and closing both valves thereby preventing further fluid flow from either end resulting in an occlusion alarm on the dialysis machine and preventing blood egress from the patient. A further aspect of the present invention is a method whereby if the axial force exerted along at least one of the tubes is great enough, the device will completely separate between the two valves after the valves have closed thereby removing the axial force from further acting on the tubing connected to the IV needle and assuring that it will not be accidentally removed.

Yet another aspect of the present invention provides a method for stopping a blood pump when a force is applied to an IV tube during dialysis treatment. The method includes the steps of: providing an occluder releasably attached to the IV tube having a first and second end, the first end hydraulically connected to a discharge of the blood pump, the second end hydraulically attached to an IV needle, wherein the IV needle is connected to a patient receiving dialysis treatment; applying a tensional force along the IV tube between the first end and the second end; occluding the IV tube; triggering an occlusion alarm; and stopping the blood pump.

BRIEF DESCRIPTION OF THE DRAWINGS

These and other features, aspects, and advantages of the present invention will become better understood with regard to the following description and accompanying drawings:

FIG. 31 is a top view of the embodiment shown in FIG. 30 with a flexible tube in an unoccluded position;

FIG. 32 is a top view of the embodiment shown in FIG. 30 with a flexible tube in an occluded position;

FIG. 62 is a cross-section view of an embodiment of the invention in an unoccluded position taken along the centerline with a flexible tube attached;

FIG. 63 is a cross-section view of the embodiment in FIG. 62 in a partially occluded position taken along the centerline with a flexible tube attached;

FIG. 64 is a cross-section view of the embodiment of FIG. 62 in an occluded position taken along the centerline with a flexible tube attached;

FIG. 69 is a side view of an embodiment of the invention in an unoccluded position with a flexible tube attached;

FIG. 70 is a cross-sectional view of the embodiment shown in FIG. 69 taken along the line A-A;

FIG. 71 is a perspective view of the embodiment shown in FIG. 69 in an unoccluded position with a flexible tube attached;

FIG. 75 is a front view of the embodiment shown in FIG. 69 in an unoccluded position with a flexible tube attached;

FIG. 76 is a rear view of the embodiment shown in FIG. 69 in an unoccluded position with a flexible tube attached;

DETAILED DESCRIPTION

Figure 1:
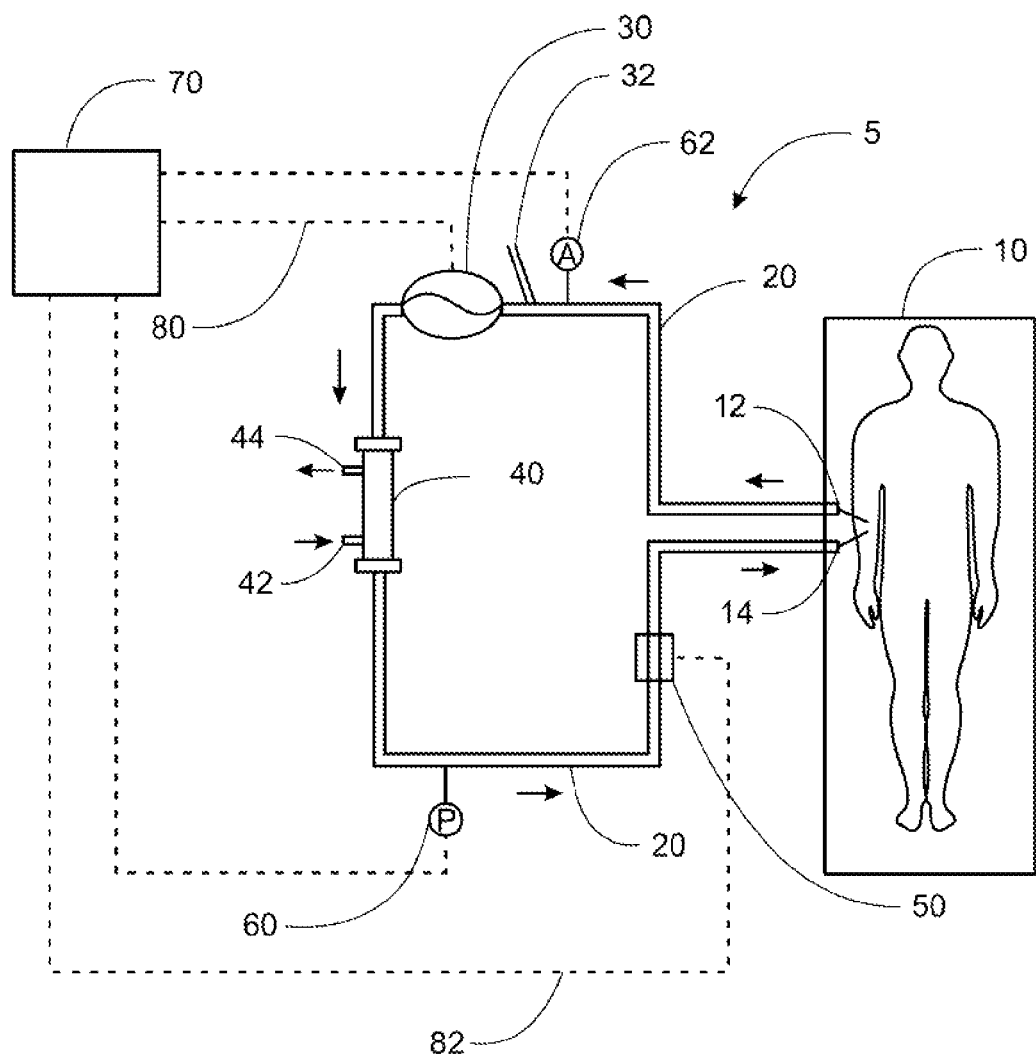
FIG. 1 is a schematic view of an extracorporeal blood circuit that embodies features of the invention.

As shown in FIG. 1, a typical hemodialysis system includes an extracorporeal blood circuit 5 connected to a patient 10. The extracorporeal circuit 5 generally includes two sections of flexible intravenous ("IV") tubing 20 configured for hemodialysis treatment (commonly referred to as arterial and venous blood sets). In a two-needle arrangement, blood is withdrawn from the patient through an arterial access catheter or needle 12 and returned through a venous access catheter or needle 14, each of which may have an attached or connected length of extension tubing that is typically of smaller diameter than the blood sets of the extracorporeal circuit. Each access catheter/needle also typically terminates in a female luer locking connector. Blood from the arterial catheter/needle is transferred via a blood pump 30 to a dialyzer 40 mostly continuously during a given therapy session at anywhere between 200 and 800 ml/min. Dialysate, a clean solution, is pumped to the inlet 42 of the dialyzer 40 where it flows in a counter-current direction to the blood and exits the dialyzer at the outlet 44. Heparin, an anticoagulant, is typically added to the extracorporeal blood circuit 5 at an injection site 32 upstream of the dialyzer 40. The treated blood leaves the dialyzer 40 and is pumped through the venous blood set before the blood is returned to the patient 10 through a venous catheter/needle 14 with or without extension tubing. In some embodiments, the occluding device 50 that is the subject of this invention may either be located on the venous or arterial blood set, or along the extension tubing between the venous or arterial blood set and the venous or arterial catheter/needle by incorporating male and female locking luer connectors on the ends of tubing segments and the connecting end of the venous catheter/needle assembly. It may be preferable to place the occluding device 50 over a segment of intervening extension tubing because it is typically of smaller diameter and therefore more easily occluded. In any case, the occluding device 50 is preferably located sufficiently close to the venous fistula needle 14 such that any force tending to dislodge the needle from the patient's arm will also be applied to the occluding device 50, triggering its actuation before a dislodged needle can cause significant blood loss.

Certain elements of the circuit may communicate with a dialysis control system 70. The control system 70 may receive pressure signals from a number of pressure sensors, and most particularly form pressure sensor 60 on the venous return line of extracorporeal circuit 5. The control system 70 may also receive signals from a number of air-in-line sensors, and most particularly from air-in-line sensor 62 on the arterial side of extracorporeal circuit 5. Detection by sensor 62 of any air in the arterial line can result in an alarm-level signal being sent to controller 70, which can then send a stop command to blood pump 30, and signal an audible and/or visual alarm to the patient 10 or a health care provider. Detection by sensor 60 of intraluminal pressure above or below a predetermined operating pressure range can trigger control system 70 to issue an alarm signifying partial or complete occlusion of the venous tubing in circuit 5, resulting, for example in a stop command 80 being sent to blood pump 30. Pressure in the extracorporeal blood circuit 5 can be affected by an obstruction or flow restriction within the blood tubing 20 of the extracorporeal circuit (an "occlusion"). Typically occlusions in the blood sets or needle sets downstream from blood pump 30 are caused by kinking or bending of flexible tube 20, reducing the cross-sectional area of the tube enough to restrict the flow of blood through tube 20 and creating excessive back pressure in the upstream blood circuit, and detectable, for example, by pressure sensor 60. If an occlusion occurs upstream of blood pump 30, an additional pressure sensor in the arterial line may detect a pressure below the predetermined operating range. In either case, an occlusion alarm can be triggered in the control system 70, sending, for example, a stop command 80 to blood pump 30.

The presence of occluding device 50 for compressing or occluding a flexible tube 20 can cause a similar stop command 80 if there is a threatened dislodgement of catheter/needle 14 from the patient's body 10. Triggering of the device 50 will raise intraluminal pressure in the venous tubing 20 sufficiently to send an alarm-level signal to controller 70 via pressure sensor 60. The predetermined operating pressure range can be programmed independently for pressure sensor 60, as well as any other pressure sensors in the system.

In an additional embodiment, and as part of a redundant or failsafe safety system, the occluding device 50 may also include a mechanical, electrical or magnetic switch or sensor capable of sending an occlusion signal 82 to control system 70 upon actuation of the occluding device 50, the control system then transmitting a stop command 80 to blood pump 30. The occlusion signal 82 may be transmitted to control system 70 wirelessly or by conventional means such as a signal wire.

In an embodiment, the occluder assembly is a tubing tension-activated clamp that is capable of applying an occluding force on the wall of a flexible tubing, restricting the flow of fluid within the tubing and increasing its intraluminal pressure, in response to a pulling force being applied to the tubing on either end of the device. The occluder assembly is triggered whenever a pulling force is applied to a length of the flexible tubing that would be sufficient to risk dislodgment of an intravascular needle connected to the flexible tubing and secured to the patient by standard means such as taping. The invention takes advantage of the fact that tension on a length of tubing can cause a certain degree of stretching of the tubing before it causes an attached intravascular catheter to dislodge, assuming that a section of the tubing or catheter is secured to a person's body by tape. Alternatively, tension on a length of tubing can cause a length of that tubing to move if a sufficient amount of slack exists in a segment of the tubing located in an occluder assembly. In this example, the occluder assembly is relatively flatter in one dimension than an orthogonal dimension, allowing it to rest reasonably securely and comfortably on a patient's arm or other part of the body. Preferably, the occluder assembly allows the user to easily load a length of tubing into the assembly and reset or rearm the assembly using one hand.

Figure 2:
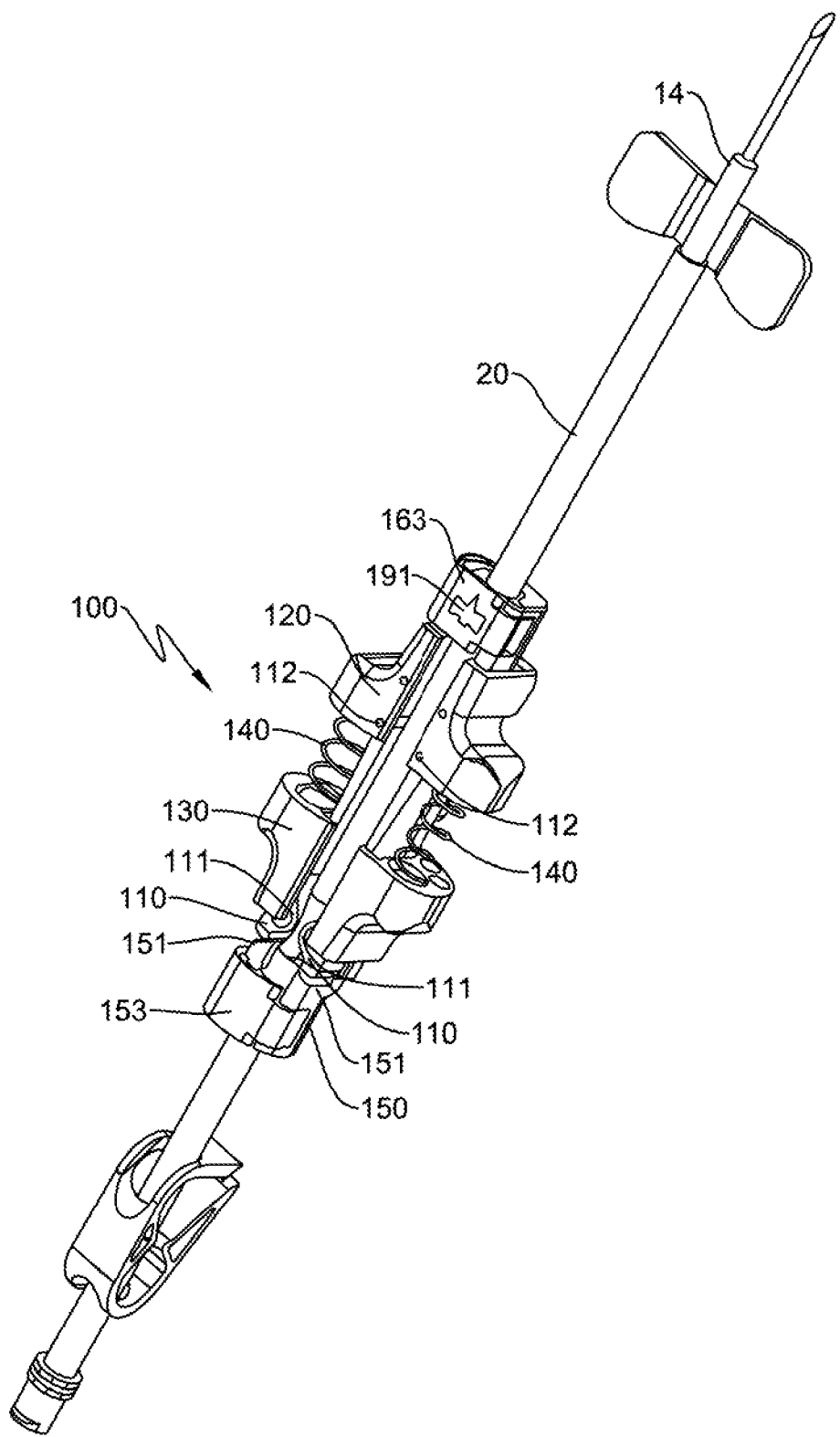
FIG. 2 is a perspective view of an embodiment of the invention in an occluded position with a segment of flexible tube latched within the device.

FIG. 2 illustrates an occluder assembly 100 in which a segment of flexible tubing 20 attached to access needle 14 is mounted. In this embodiment, the occluder assembly 100 includes one or more occluders 110 having occluding elements 111 at the distal end of occluders 110, the occluders 110 being pivotally connected at their proximal ends 112 to a base unit 120. The one or more occluders 110 can be forced together (or forced toward a stationary member in the case of a single occluder), directing occluding elements 111 toward the enclosed tubing 20 by the actuator 130 as it advances distally toward the distal end of the one or more occluders 110. The clamping action of the one or more occluders 110 is not unlike the clamping action that a collet exerts on an internally disposed object when a collet socket is advanced over the collet. In this example, the flexible tubing 20 is colleted within one or more occluders 110 as an enclosing actuator 130 advances distally along the outer surface of the one or more occluders 110. (Note that pairs or a plurality of components of the occluder assembly 100 will be described below, assuming the presence of two or more occluders. Although two or more occluders may be a preferred embodiment, the description should not be interpreted to exclude the possibility of having single components as appropriate if only one occluder is contemplated for the invention.)

The actuator 130 is driven distally by actuator springs 140, and in so doing forces the distal ends of occluders 110 toward each other (or toward a stationary member in the case of a single occluder). Frame 150 includes occluder stops 151 that support the distal ends of occluders 110 in an open or 'armed' position, preventing actuator springs 140 from moving actuator 130 distally along occluders 110. Upon application of a pulling force on flexible tubing 20, frame 150 is distracted from base unit 120. The distraction is sufficient to move the distal ends of occluders 110 off the occluder stops 151, thereby allowing the occluders 110 to move toward each other and the actuator 130 to advance distally under the force of actuator springs 140. Any stretching force applied to tubing 20 is translated into a distracting force between base unit 120 and frame 150 because the tubing 20 is gripped securely at each end of occluder assembly 100. In this case, the spring force needed to drive the actuator 130 along occluders 110 can be divided among two or more springs in order to minimize the diameter or thickness of the individual springs, allowing the assembly 100 as a whole to have a flatter profile in one plane.

Figure 3:
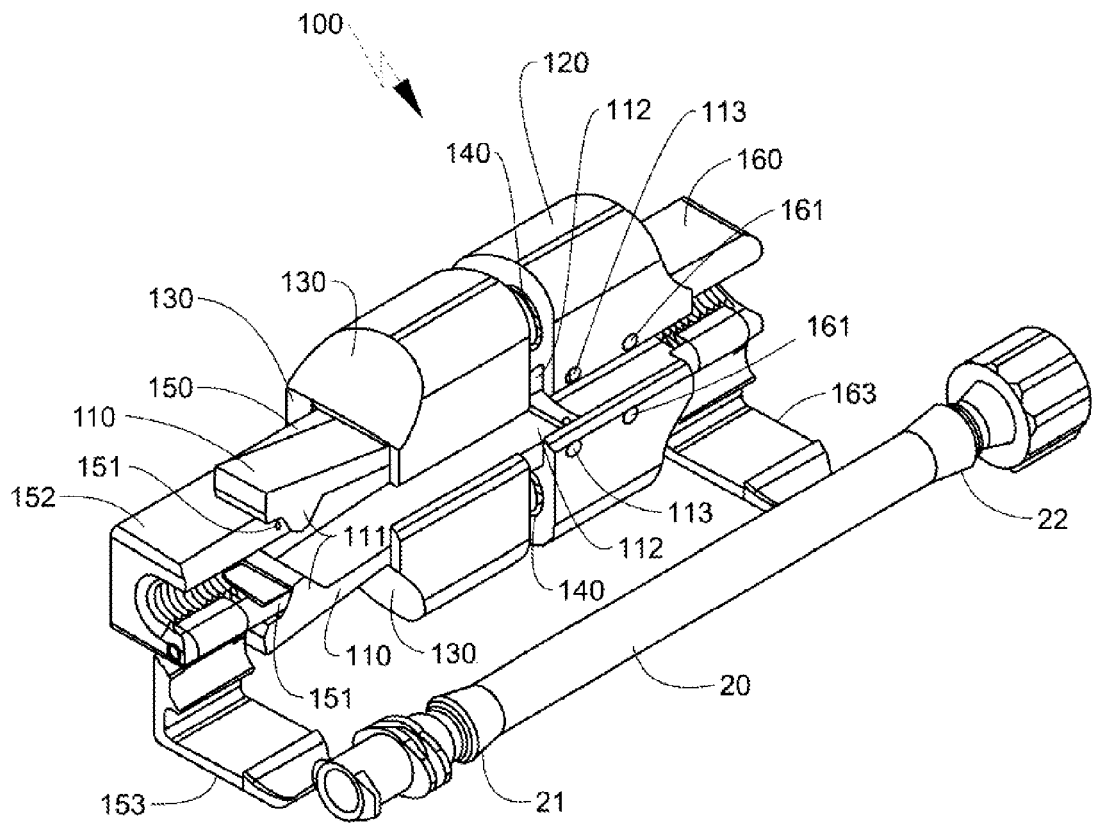
FIG. 3 is a perspective view of an embodiment of the invention in an unoccluded position with a segment of flexible tube removed from the device.

FIG. 3 is a perspective view of an exemplary dual-spring occluder assembly 100. A c-shaped actuator 130 has two actuator segments 130a and 130b, each of which is driven by a separate actuator spring 140 (more clearly shown in FIGS. 4 and 5). The two actuator springs 140 are on one end partially housed in—or otherwise attached to—base unit 120, and on the other end partially housed in—or otherwise attached to—actuator segments 130a and 130b of actuator 130. Actuator 130 is guided by frame 150 of occluding assembly 100, frame 150 in this case also incorporating or attached to front tubing grip 152. A rear tubing grip 160 can be connected or attached to base unit 120, in this example by means of dowels or spindles 161. In the example shown, occluders 110 interact with actuator segments 130a and 130b of actuator 130 to apply a pinching force against the sides of tubing segment 20. The proximal ends 112 of occluders 110 are secured and pivot about occluder dowels or spindles 113 mounted in base unit 120. In other embodiments, a single occluding arm may be present, the opposing member acting merely as a stationary guide for the opposing actuator segment of the actuator. Tubing segment 20 can be placed between occluders 110 and the two actuator segments 130a and 130b of actuator 130. Base unit 120 is also c-shaped to accommodate the placement of tubing segment 20 in the center of occluding assembly 100.

Figure 4:
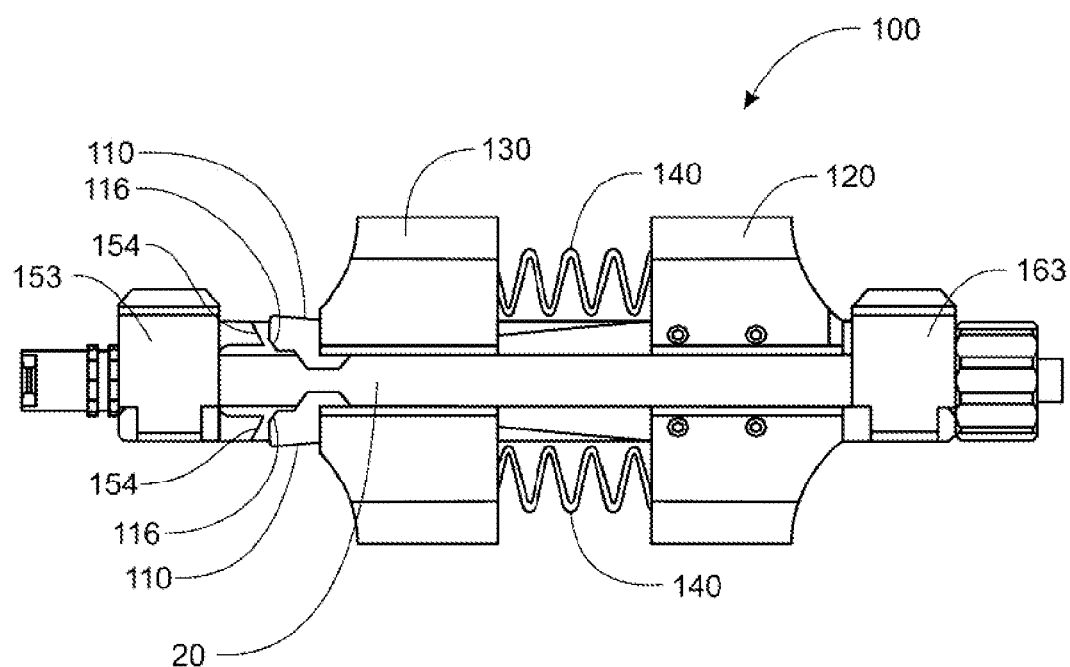
FIG. 4 is a plan view of the embodiment of FIG. 3 in an occluded position with a segment of flexible tube mounted in the device.

Occluding assembly 100 can be triggered to occlude tubing segment 20 when a pre-determined threshold amount of tension is applied to the flexible tubing 20, causing the tubing to stretch slightly (or at least causing a slackened tubing segment to straighten), pull frame 150 slightly away from base unit 120, and disengage the distal ends of occluders 110 from the occluder stops 151. Once the ends of occluders 110 clear contact with occluder stops 151, the actuator spring 140 provides a force against actuator 130 that is sufficient to overcome frictional resistance between actuator segments 130a and 130b and occluders 110, and advance actuator 130 along the outer surfaces of occluders 110, imparting a pincer or clamping force between occluding elements 111. As shown in FIG. 4, a longitudinally directed actuator spring 140 provides a force causing movement of actuator 130 along occluders 110 imparts an orthogonal force against the side walls of tubing 20, occluding or constricting its lumen. The occluding force of the occluders 110 is maintained by the force of the actuator springs 140 acting on actuator 130.

Front 152 and rear 160 tubing grips can comprise channels that can secure tubing segment 20 within occluder assembly 100. In an additional embodiment, a front latch 153 and rear latch 163 are pivotally connected to front 152 and rear 160 tubing grips, respectively, and can swing and snap open and closed over grips 152 and 160, and the enclosed tubing using one finger or a finger and thumb of a single hand. The latches 153 and 163 can have handles that facilitate manipulating the latches with a fingertip. The latches 153 and 163 preferably allow a user to mount a tubing segment onto occluder assembly 100 with one hand while it is resting on the user's body. The surfaces of the channels of grips 152 and 160 can preferably have tube gripping features such as ridges, ribs, cross hatches, scales or other raised surface features (including, for example, transversely aligned sawtooth ridges), or even non-raised adhesive or elastomeric surfaces, or otherwise clinging surfaces that can help to hold tubing 20 in position. These surfaces or features can provide sufficient frictional resistance to the adjacent tubing wall to prevent movement of the tubing with respect to the grips 152 and 160, particularly once the respective sections of the tubing segment 20 are securely enclosed by latches 153 and 163. In one embodiment, the surface features are capable of gripping the bare flexible tubing segments themselves. In another embodiment, the surface features are shaped to capture the profile of the flexible tube overlying the barb 21 and 22 of a coupling to which the tubing segment 20 is attached.

Figure 5:
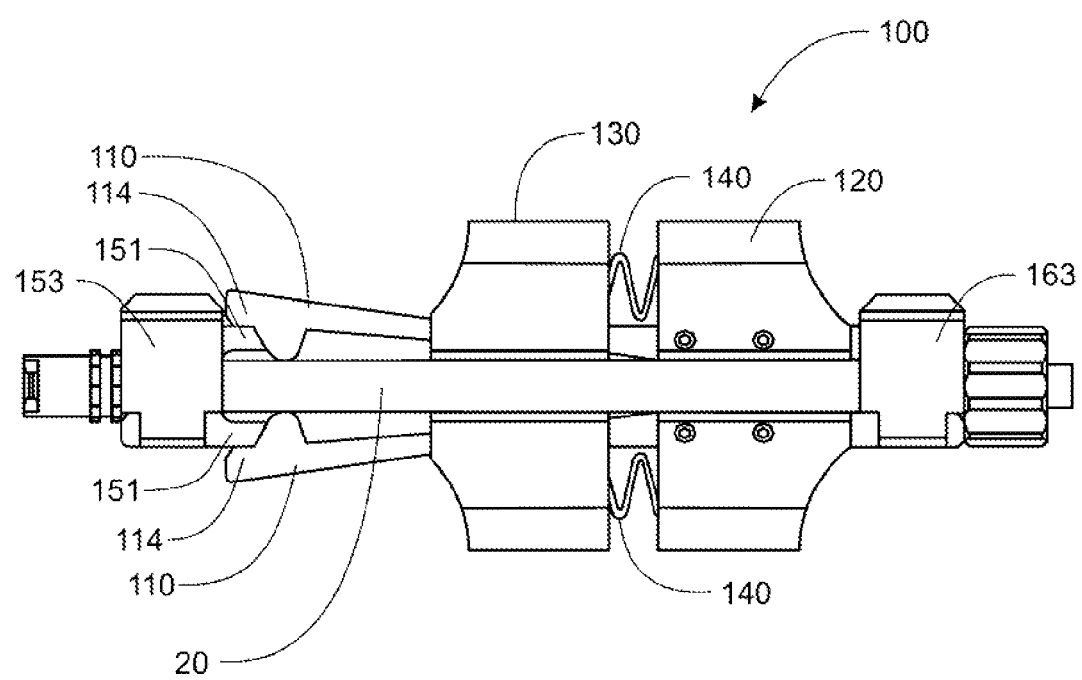
FIG. 5 is a plan view of the embodiment of FIG. 3 in an unoccluded and armed position with a segment of flexible tube mounted in the device.

As shown in FIG. 5, when occluder assembly 100 is in an armed state, occluders 110 are kept apart from each other and tubing segment 20 by occluder stops 151 acting on the ends 114 of occluders 110. The distance between occluders 110 can be sufficient to prevent actuator 130 from moving distally under the force of compressed actuator springs 140. Tension on a segment of tubing 20 outside of the occluder assembly 100 sufficient to overcome the frictional resistance between occluder stops 151 and occluder ends 114 will cause disengagement of occluders 110 from occluder stops 151. The composition, shape and area of the mating surfaces can be varied empirically until the desired triggering tension for the flexible tubing is obtained. The triggering tension of the tubing can be determined by measuring the tubing tension required to dislodge an attached needle that has been properly taped to a person's body, and setting the triggering tension to a value safely below this needle dislodgement tension. For example, the occluder assembly 100 can be constructed to trigger upon application of approximately 0.6-1 lb of tension on a segment of the tubing 20. In some embodiments, the triggering tension may be lower than 0.6 lbs. In most circumstances, it will be prudent for the device 100 to actuate below a tension of about 1 lb., in order to accommodate situations in which an IV catheter has been taped to a person's body in a relatively cursory manner.

Figure 6:
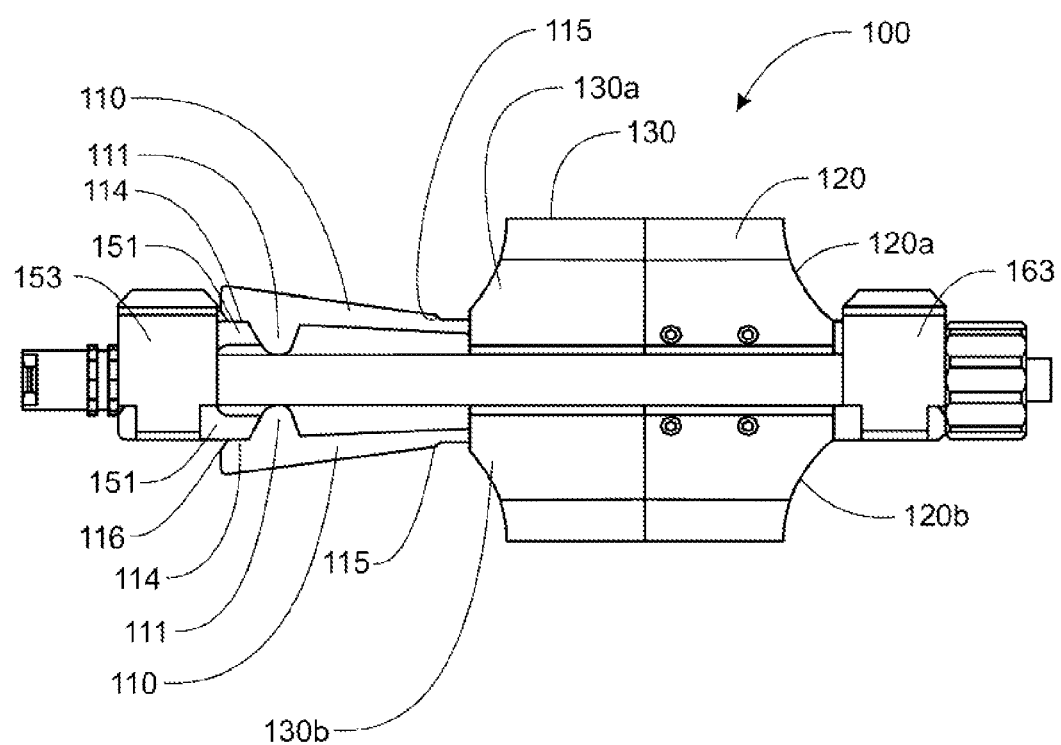
FIG. 6 is a plan view of the embodiment of FIG. 3 in an unoccluded position with the actuator in a fully retracted position with a segment of flexible tube mounted in the device.

Over time and use, and depending on the type of material used for the occluders 110 and frame 150, the frictional resistance between occluder ends 114 and occluder stops 151 may change, leading to a change in the threshold tubing tension force at which the occluder assembly 100 will trigger. In addition or optionally, as shown in FIG. 6, actuator rests 115 may be incorporated on occluders 110 to contact the leading edges of actuator segments 130a and 130b of actuator 130 when in an armed position. The actuator rests 115 in an embodiment comprise jog features on the outer aspect of the occluders 110, forming a mating relationship with the leading edge of the actuators 130, relieving some of the colleting forces acting on the occluders 110. Preferably, the angle of incline of the actuator rests 115 with respect to the surface of occluders 110 is sufficiently close to vertical to direct most of the compressed spring force of actuator springs 140 longitudinally along the length of occluders 110. In this manner, the amount of clamping or colleting force acting on the distal ends 114 of occluders 110 against the occluder stops 151 is decreased, reducing frictional resistance between occluder ends 114 and occluder stops 151 upon actuation of the device 100, and creating a more predictable release force when it is activated. Preferably, actuator rests 115 have an angle of incline several degrees from vertical in order not to inhibit actuator 130 from being released under the force of the compressed actuator springs 140 upon disengagement of occluder ends 114 from occluder stops 151.

Figure 7:
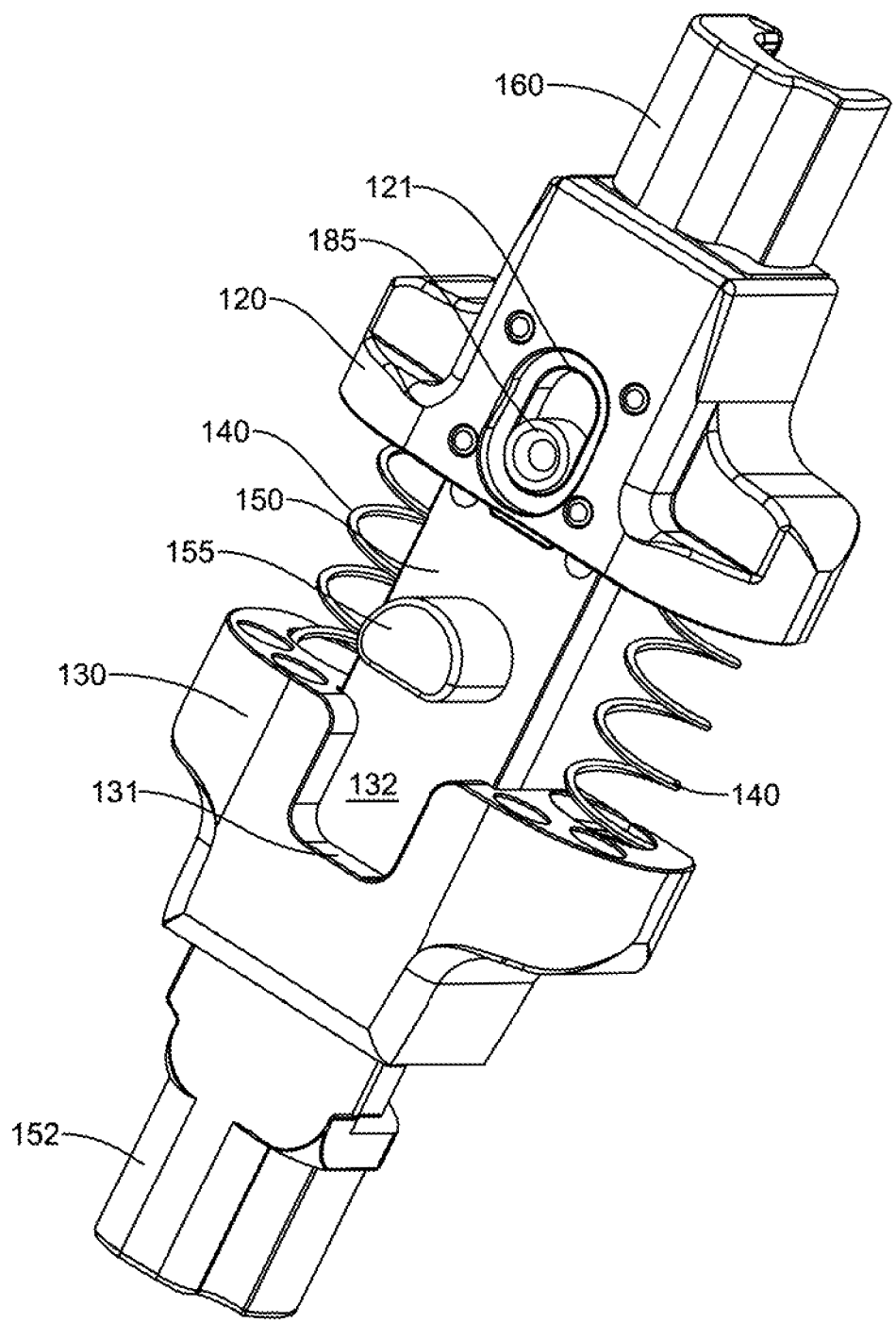
FIG. 7 is a bottom perspective view of the embodiment of FIG. 2 with the actuator fully extended.

Once the tubing segment 20 is no longer under a distracting force, occluding assembly 100 can be re-armed after it has been released by simply grasping actuator 130 and retracting it toward base unit 120, compressing actuator springs 140. As shown in FIG. 6, arming occluding assembly 100 involves having a user grip the leading sides of actuator segments 130a and 130b that preferably are shaped as finger rests, grasping, for example, with the index and middle fingers respectively, and pulling actuator 130 in a rearward direction toward base unit 120, which is being grasped by the thumb. Alternatively, the base unit segments 120a and 120b (shown in FIG. 6) can be grasped by the index and middle fingers, respectively, and the actuator can be grasped by the thumb to effectuate re-arming. By placing the thumb of the user's hand on a trailing side of base unit 120, or on a leading side of actuator 130, it is possible to arm the device using one hand. Upon doing so, as shown in FIG. 7, the trailing edge 131 of the bottom of actuator 130 can engage a frame post 155 formed from or attached to frame 150, and pull frame 150 proximally, forcing occluder stops 151 against the distal ends 114 of occluders 110, spreading occluders 110 apart and seating the distal ends 114 of occluders 110 onto occluder stops 151. In an embodiment, the trailing edge 131 of the bottom of actuator 130 optionally can comprise a slot 132 within which frame post 155 can travel, as shown in FIG. 7. In some embodiments, the slotted trailing edge 131 of the bottom of actuator 130 can help to align actuator occluders 110 with occluder stops 151 during re-arming of the device 100. In other embodiments, actuator slot 132 is long enough to allow a force on the trailing side of frame post 155 to move frame 150 forward relative to base unit 120 to trigger occluder assembly 100. As shown in FIG. 4, the leading edges 116 of occluder ends 114 can be angled to correspond to the angle of the trailing edges 154 of occluder stops 151 in order to facilitate having the occluder stops 151 slide past occluder ends 114. Once occluders 110 have been loaded onto occluder stops 151, release of actuator 130 by the user allows it to move forward under spring 140 force until reaching actuator rests 115 of occluders 110. The combination of contact with actuator rests 115 and occluder end 114 contact with occluder stops 151 places the device 100 in an armed state. Preferably, the spring rates of actuator springs 140 are moderated to allow persons of modest strength or frail constitutions to re-arm the device 100 using one hand. For example, the re-arming force required to compress actuator springs 140 and arm the device 100 can be kept at between about 4.5-5.0 lbs. Preferably, to accommodate users with a wide variety of medical conditions or infirmities, the maximum re-arming force is kept below about 6 lbs. Generally, for most medical intravenous tubing in current use, the spring rates of occluder springs 140 that this guideline permits are still sufficient to fully occlude a flexible tubing containing fluid under at least about 800 mm Hg of intraluminal pressure. In other medical or non-medical applications, the amount of intraluminal pressure under which the occluding device will still operate successfully may be higher. If so, then the occluder springs may need to be replaced by springs having higher spring rates. Furthermore, if the stiffness or resiliency of the flexible tubing being used varies from the tubing covered by the described embodiments of device 100, the occluder springs may need to be replaced by springs having higher or lower spring rates.

The distracting force on tubing segment 20 needed to trigger release of occluders 110 can be adjusted by altering the frictional surface characteristics of occluder ends 114, for example, or by altering the surface area with which they contact occluder stops 151, or of their incline angle with occluder stops 151. In addition, the contacting surfaces between occluder stops 151 and occluder ends 114 can have different mating relationships (e.g., tooth-and-groove profile), depending on the degree of distracting force desired to activate the occluding assembly 100.

Preferably, the tension-activated occluding assembly 100 should trigger within a relatively narrow range of applied tension on the flexible tubing 20 to which it is attached. Furthermore, the triggering characteristics of the occluding assembly 100 should preferably not vary over time and after repeated use. Factors such as variations in manufacturing processes, required tolerances between moving parts, and wear of contacting surfaces from repeated use can be mitigated by additional enhancements of the occluding assembly 100 described above.

Figure 8:
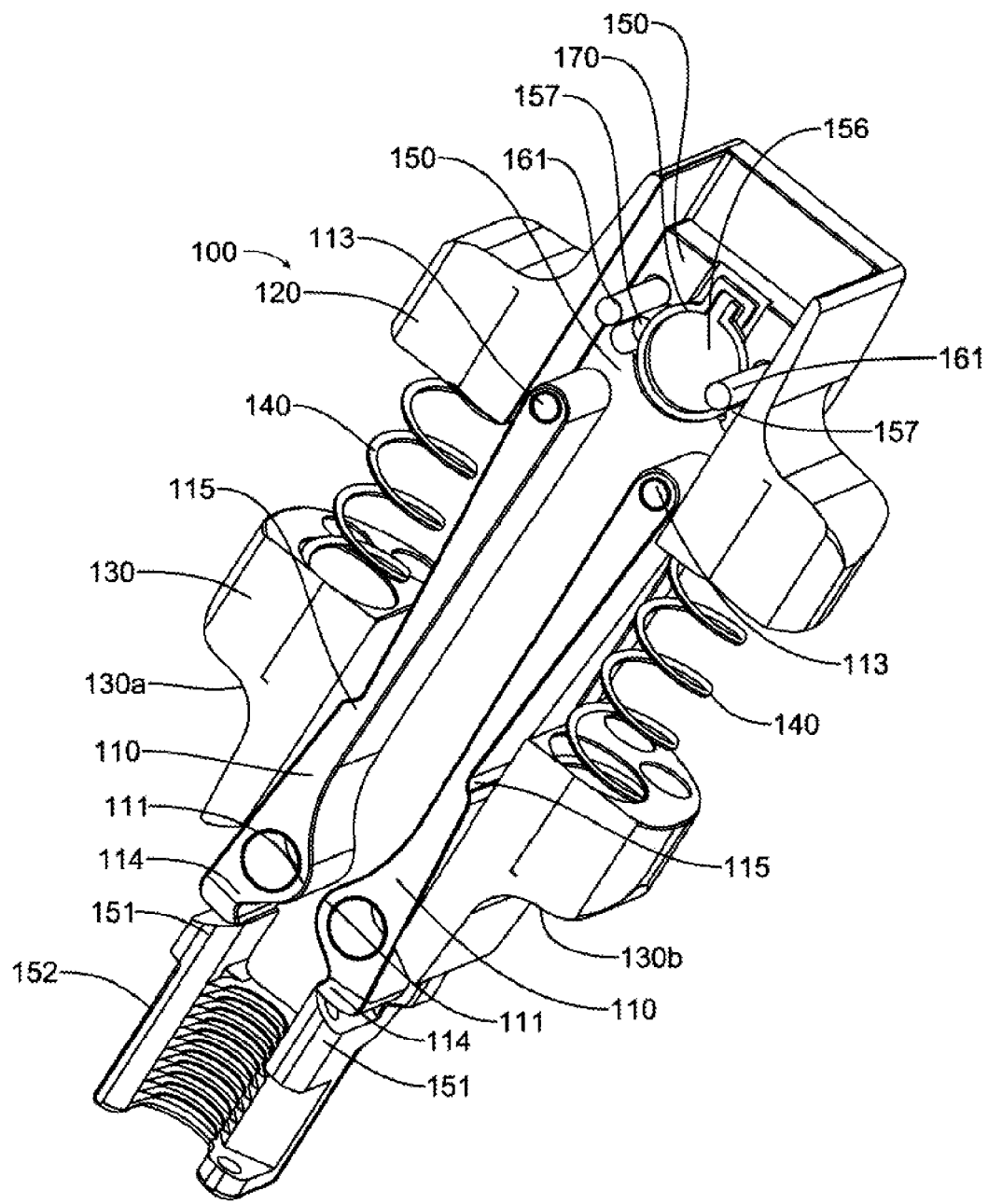
FIG. 8 is a top section perspective view of the embodiment of FIG. 2 showing the occluders in an occluding position.
Figure 10:
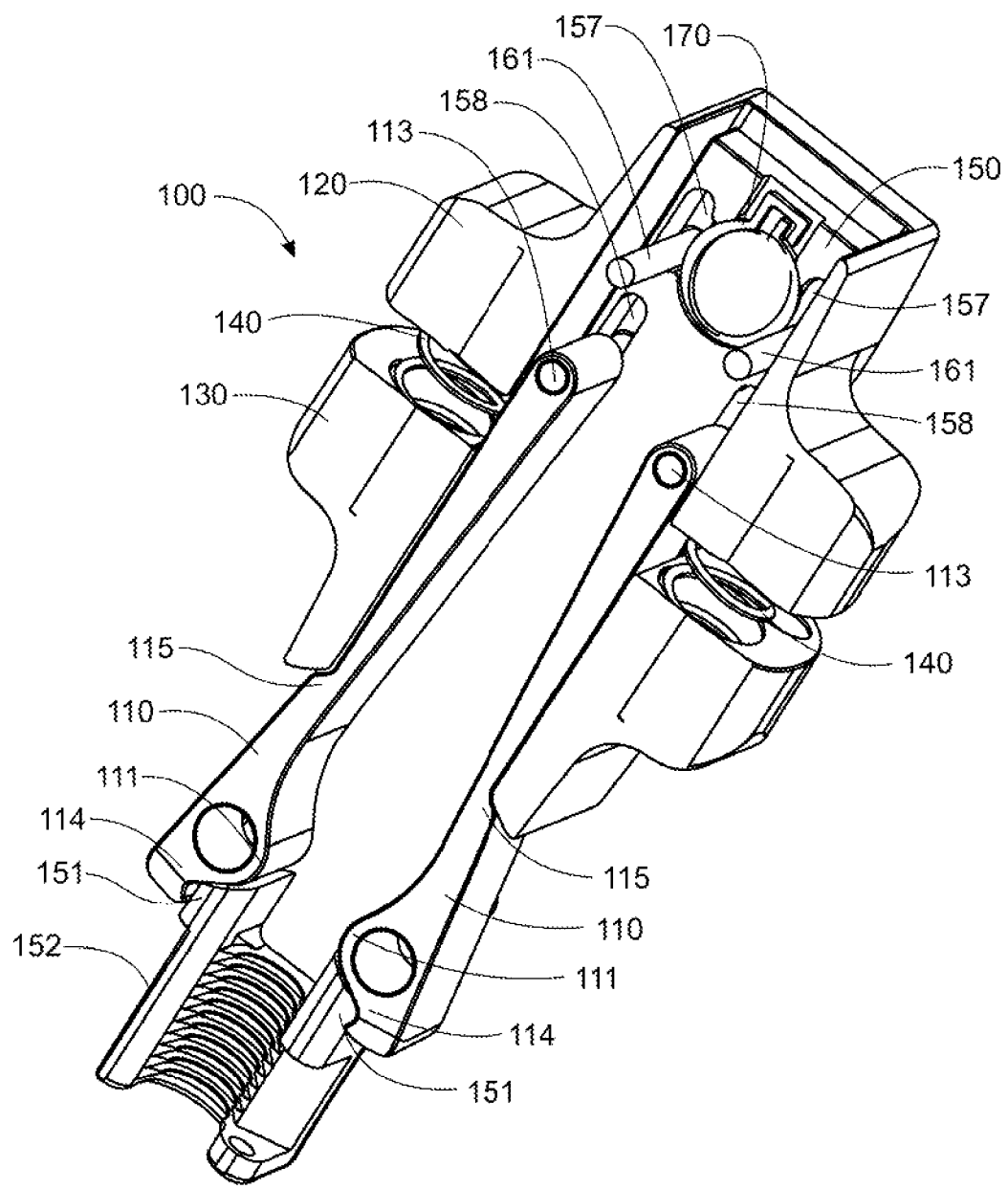
FIG. 10 is a top section perspective view of the embodiment of FIG. 8 showing the occluders in a non-occluding armed position.

FIG. 8 is a cutaway view of another embodiment of occluding assembly 100 incorporating a triggering spring 170 that can assist in keeping occluding assembly 100 in an armed state until a distracting force is applied that is sufficient to slide trigger dowels or spindles 161 across slots 157 and compress triggering spring 170, allowing movement of frame 150 away from base unit 120 (or vice versa) under the force of actuator springs 140. As shown in FIG. 10, note that occluder dowels or spindles 113 are mounted in base unit 120 and can slide along slots 158 of frame 150 along with trigger dowels or spindles 161, allowing for translational or longitudinal movement of occluders 110 (along with base unit 120) relative to frame 150.

Figure 9A:
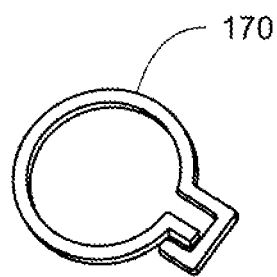
FIGS. 9a and 9b are perspective and plan view, respectively, of a triggering spring used in the embodiment of FIG. 8.
Figure 9B:
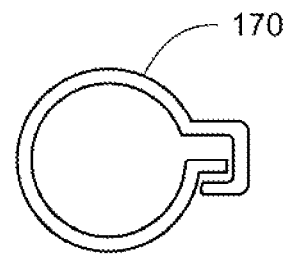
Figure 9C:
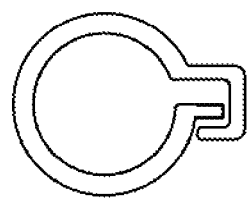
FIGS. 9c and 9d are plan views of triggering springs used in the embodiment of FIG. 8 and having different thicknesses and spring rates.
Figure 9D:
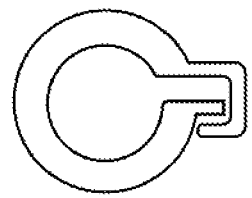

A circular triggering spring 170 is illustrated in this embodiment, but any other type of spring could be used to achieve the same result, i.e., providing a spring-based trigger mechanism that does not depend on friction between moving parts to cause the occluding assembly 100 to release. For example, occluder stops 151 could include spring-loaded protrusions positioned to keep occluders with appropriately shaped ends in an armed position. The spring-loaded protrusions would be compressible by a pre-determined threshold tension force on tubing 20, allowing the occluder ends to slip off the occluder stops and trigger the device. Triggering spring 170 can be placed within its recess 156, and can be held in position by positioning rear tubing grip 160 over the spring 170 and recess 156. With this type of installation, one can readily adjust the triggering force by disassembling the rear tubing grip 160 from the base unit 120, and substituting a triggering spring having a different spring rate. This can be accomplished, for example, by varying the thickness of the ring of triggering spring 170, as shown in FIG. 9. FIGS. 9a and 9b show a triggering spring having the lowest of three exemplary spring rates in perspective and top views, respectively. FIGS. 9c and 9d show triggering springs having progressively increasing spring rates, respectively. In a typical application using current medical-grade tubing, triggering spring 170 should be compressible by trigger dowels or spindles 161 in response to a pulling force on the tubing 20 of about 0.6-1 lb. In some embodiment, the pulling force range that can cause compression of triggering spring 170 can be in the range of about 0.5 to 2 lbs. The triggering force can be adjusted up or down for other medical or non-medical uses by substituting a triggering spring 170 having a different spring rate. The triggering spring characteristics can also be changed if the flexible tubing in use has different elastic or tensile properties from those covered by the embodiments of device 100 described herein.

Figure 11:
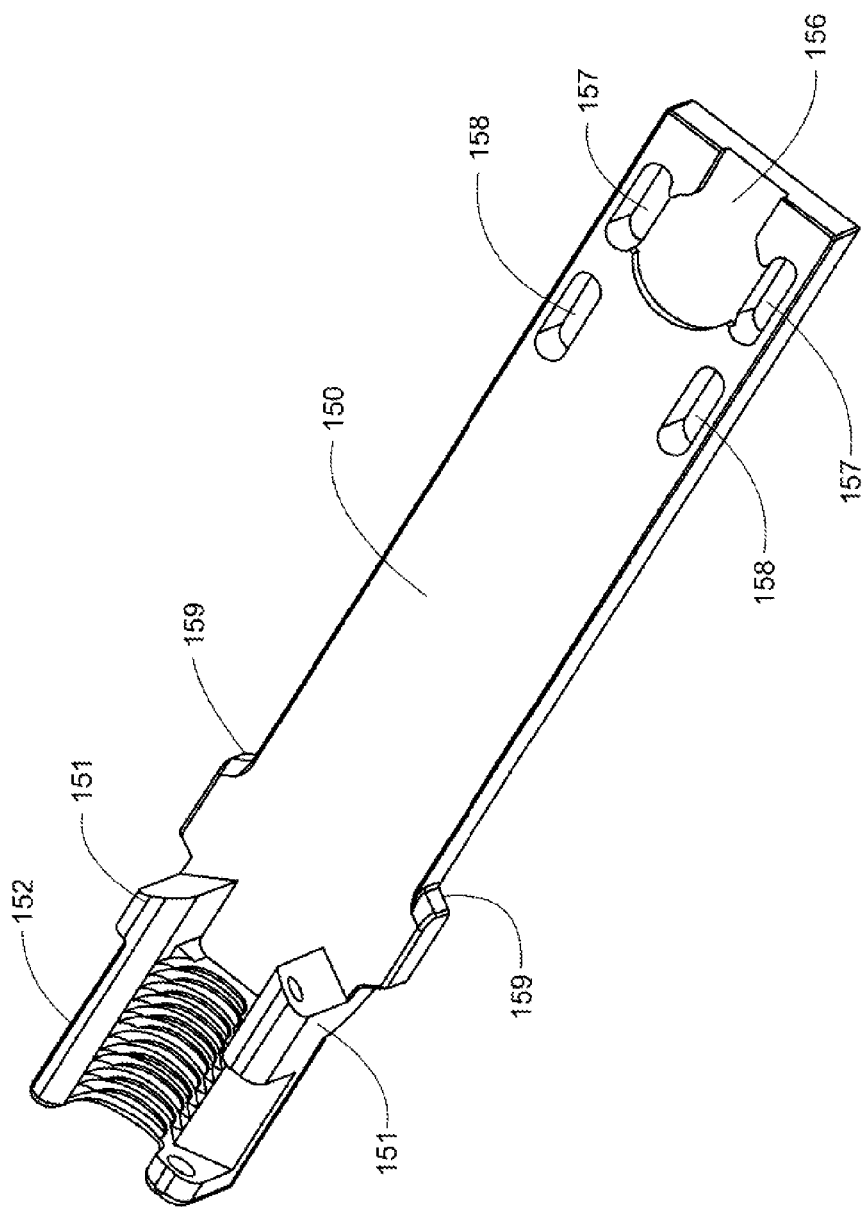
FIG. 11 is a top perspective view of the frame of the embodiment of FIG. 8.

Use of a triggering spring as the principal means of triggering the device reduces reliance on the frictional resistance between occluder stops 151 and occluder ends 114 for an accurate and precise response to a triggering force. By having the triggering force depend mostly on compression of the triggering spring, the device 100 is able to trigger in response to a tension force on tubing 20 in a more reliable or consistent manner over many cycles of device use. In the illustrated example, trigger dowels or spindles 161 compress triggering spring 170 as frame 150 slides back and forth within the track formed by base unit 120. FIG. 8 shows the positions of trigger dowels or spindles 161 relative to triggering spring 170 and frame 150 when occluders are in a released or occluding position. FIG. 10 shows the positions of trigger dowels or spindles 161 relative to triggering spring 170 and frame 150 when occluders 110 are in an armed position. Movement from an armed position to a released (occluding) position requires trigger dowels or spindles 161 to move along slots 157, transiently compressing triggering spring 170 in the process. In an embodiment, trigger dowels or spindles 161 may also serve to attach rear tubing grip 160 to base unit 120, as shown, for example, in FIG. 3 and FIG. 12. In different embodiments, the rear tubing grip 160 can be a detachable or permanently affixed component of the occluder assembly 100. The rear tubing grip 160 can include a channel in which a segment of tubing 20 is placed and secured. As with front tubing grip 152, the channel of rear tubing grip 160 can have surface features that promote gripping of the enclosed segment of tubing 20, particularly when latch 163 has been secured over the channel of tubing grip 160. In this embodiment, frame 150 includes a triggering spring recess 156 to accommodate secure placement and proper function of triggering spring 170. Frame 150 also has slots 157 to accommodate movement of frame 150 relative to base unit 120. These features are more clearly shown in FIG. 11, which shows the top side of frame 150 in isolation. Slots 157 allow frame 150 to move relative to trigger dowels or spindles 161 mounted in base unit 120, while slots 158 allow frame 150 to move relative to occluder dowels or spindles 113 mounted in base unit 120. Also shown in this embodiment are actuator stops 159, which prevent actuator 130 from overshooting its fully triggered position.

Figure 13:
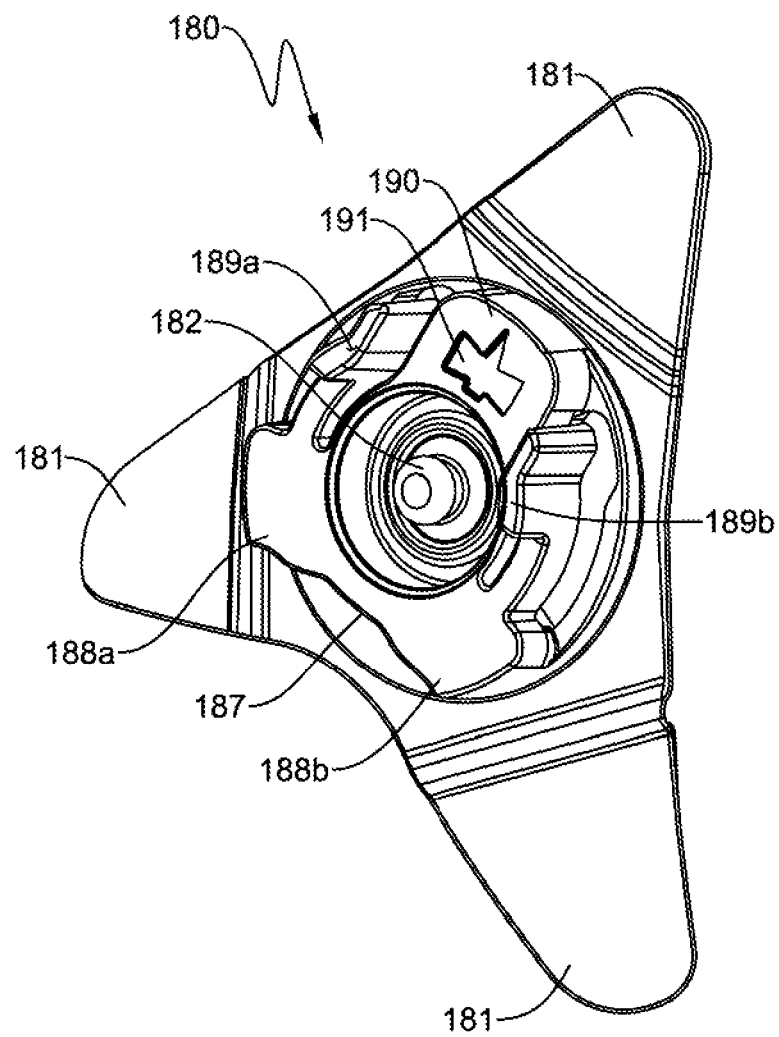
FIG. 13 is a perspective view of the mounting pad shown in FIG. 12.

In another embodiment, occluder assembly 100 can be mounted onto a mounting pad 180, which in turn can be affixed to any surface, including a patient's arm or other body part. Preferably, mounting pad 180 is shaped so that portions of it can be readily taped onto a person's arm, for example, using only one hand. FIG. 13 shows one such example, in which mounting pad 180 includes one or more extensions or wings 181 across which strips of tape may be placed when affixing mounting pad 180 onto a person's arm. In this case, one need only apply a strip of tape onto one of the extensions 181, lift the mounting pad 180 by the tape-extension combination, and place it on a suitable surface, pressing the two ends of the strip of tape onto the receiving surface. Following this, additional strips of tape can be placed on the remaining extensions or wings 181 to secure mounting pad 180 to the recipient surface. The mounting pad may also be a disposable pad with pre-applied adhesive or VELCRO material covering the undersurface of the mounting pad, which allows the mounting pad to be securely mounted to the user's skin. In other embodiments, the structural components of the mounting pad that interact with the occluder assembly 100 may be connected or attached to a strap that can be worn around a user's arm or wrist.

Figure 14:
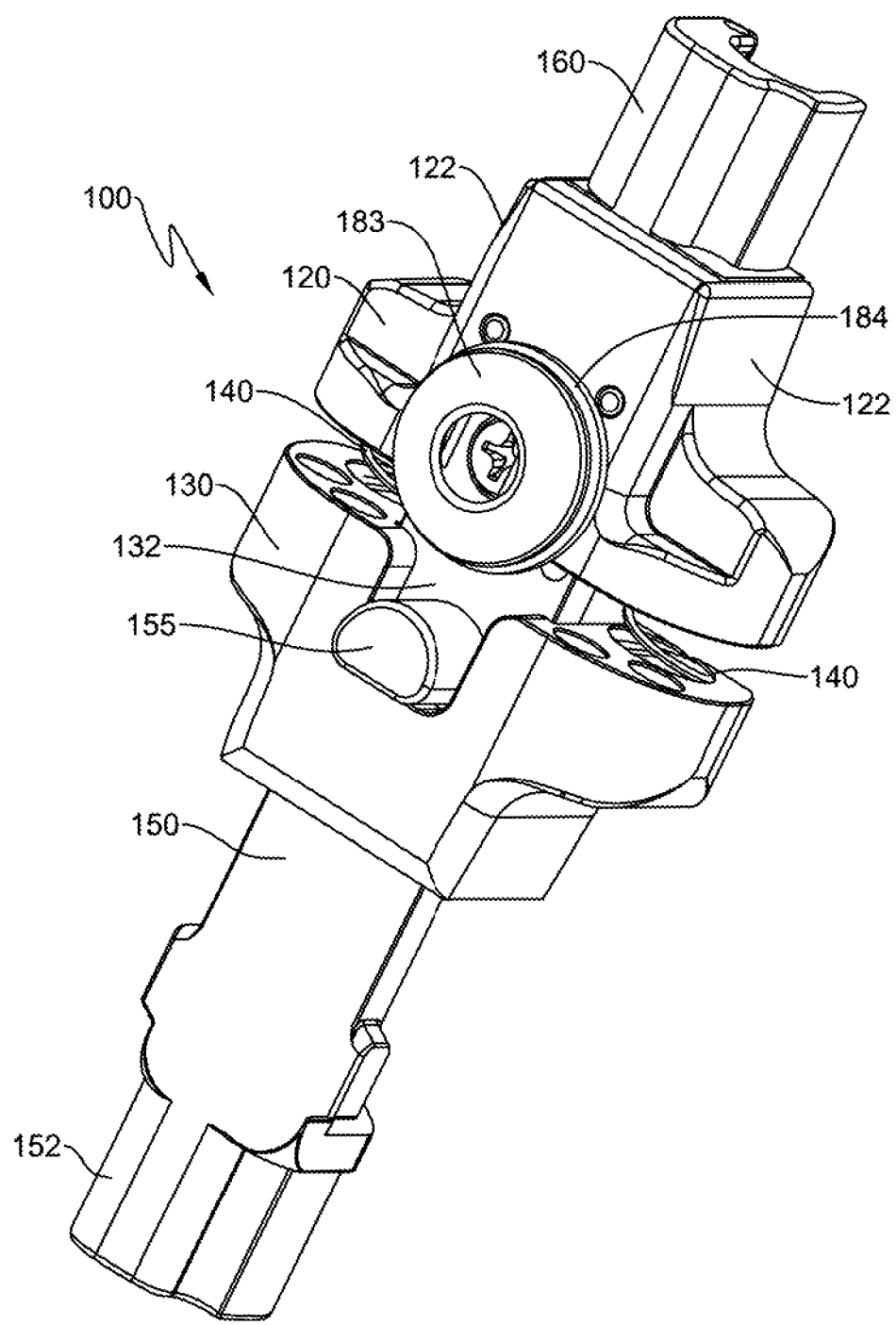
FIG. 14 is a bottom perspective view of the embodiment of FIG. 2 showing the female component of a snap fastener by which the device attaches to the mounting pad.

In an embodiment, mounting pad 180 attaches to the bottom of occluder assembly 100 by means of a snap fastener, the male component 182 of which is seen in FIG. 13. The snap fastener comprises a male component and female component, either of which can be attached to the center of mounting pad 180. In this example, the male component 182 is attached to mounting pad 180. Using a snap fastener allows the attached occluder assembly 100 to rotate about an axis formed by the male component 182 (or alternatively a snap fastener female component). The occluder assembly 100 advantageously can also be attached to and removed from mounting pad 180 using one hand. The female component 183 of the snap fastener is shown in FIG. 14. In this example, it is screwed to the bottom of occluder assembly 100 adjacent the bottom side of base unit 120. A Teflon washer 184 or other relatively frictionless spacer can be inserted between female component 183 and the adjacent surface of base unit 120. In an embodiment, the female component 183 is connected rigidly to base unit 120. Thus, any pulling force on tubing 20 on the front end of occluder assembly 100 (i.e. next to front tubing grip 152) will be resisted through the base unit by both the portion of the tubing 20 that is taped onto the user's body, and by the mounting pad 180, which is also secured to the user's body.

Figure 15:
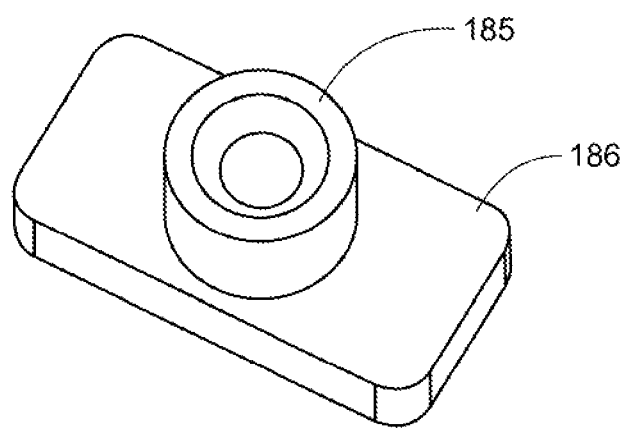
FIG. 15 is a perspective view of the snap fastener mount by which the female component of the snap fastener is mounted to the device.
Figure 16:
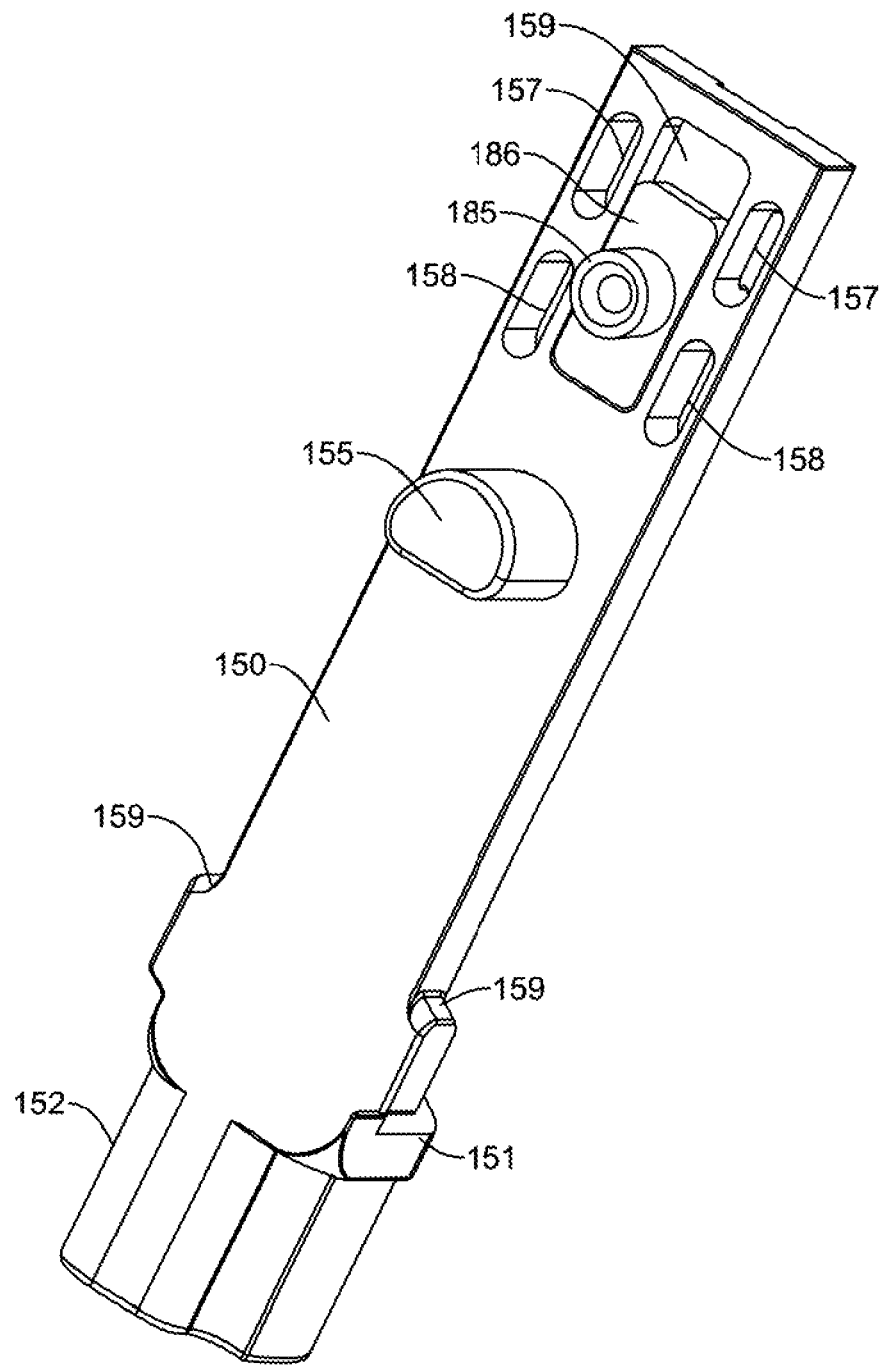
FIG. 16 is a bottom perspective view of the frame of the embodiment of FIG. 7 showing the positioning of the snap fastener mount.
Figure 17:
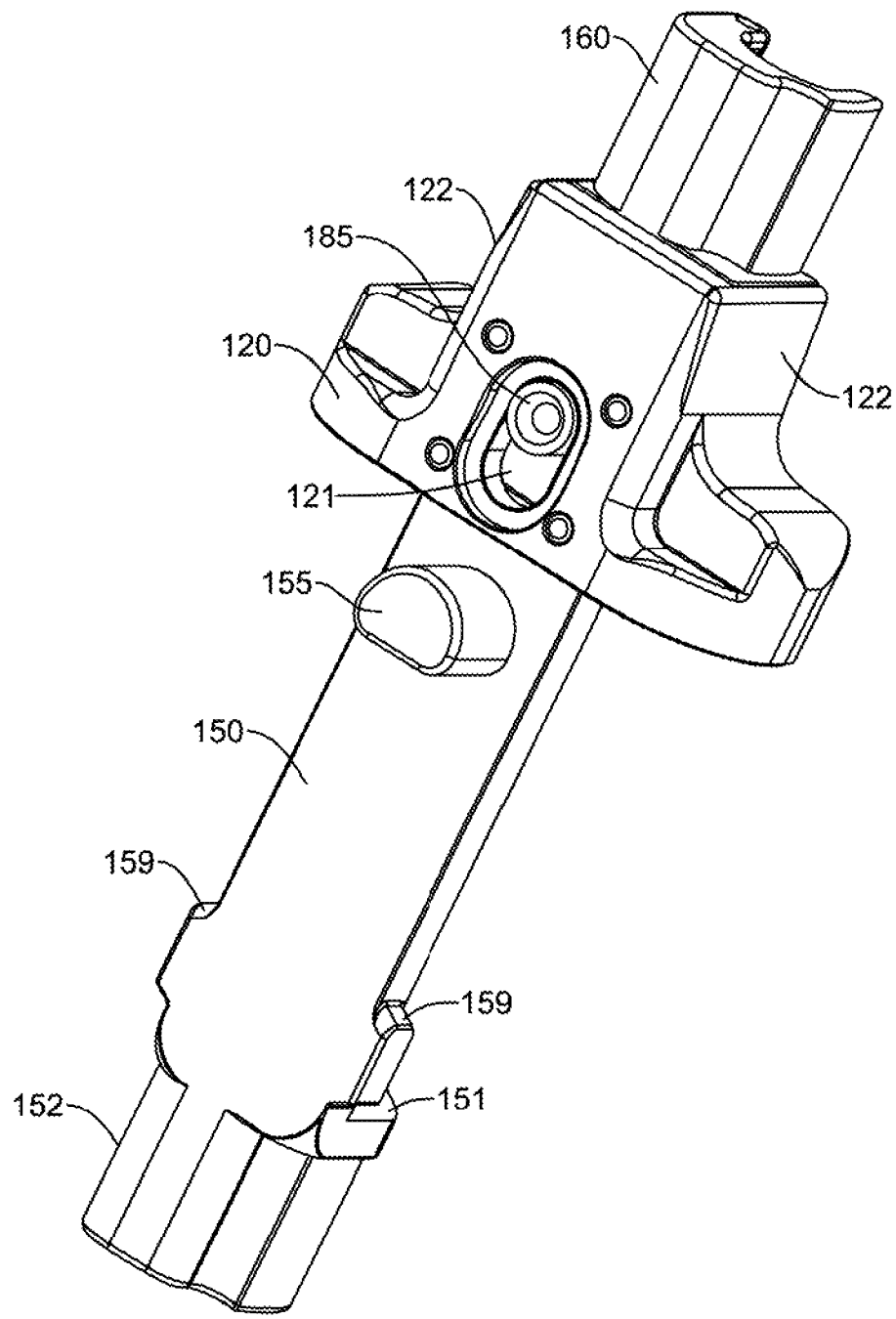
FIG. 17 is a bottom perspective view of the base unit mounted on the frame of the embodiment of FIG. 7 showing the snap fastener mount protruding through the base unit slot.

In another embodiment, the mounting pad 180 is loosely connected to occluder assembly 100 via a mounting body that can move back and forth a short distance in a slot within base unit 120. If the mounting body is made to contact a trailing edge of frame 150 before contacting the front edge of the base unit 120 slot, then occluder assembly 100 can be made to trigger with a pulling force being applied to tubing 20 at the back end of occluder assembly 100 (i.e. next to rear tubing grip 160), in addition to the front end of occluder assembly 100. Rather than attaching directly to base unit 120, for example, female component 183 can be connected to a snap fastener mount 185, shown in FIG. 7. Snap fastener mount 185 protrudes through, and can move back and forth within base unit slot 121. Snap fastener mount 185 is shown in isolation in FIG. 15. The base 186 of snap fastener mount 185 is sized to fit loosely within frame slot 159 on the bottom side of frame 150, as shown in FIG. 16. Snap fastener mount 185 can thus move back and forth within slot 159. Snap fastener mount 185 is held within occluder assembly 100 by base unit 120, as shown in FIG. 17. The mounting feature of snap fastener mount 185 protrudes through base unit slot 121. Thus, snap fastener mount 185 (and therefore its subsequently attached mounting pad 180) can move relative to both frame 150 and base unit 120. Once snap fastener mount 185 has reached the end of aft travel (i.e. toward rear tubing grip 160) with respect to base unit slot 121 (as shown in FIG. 17), it can travel further aft with respect frame slot 159, taking base unit 120 along with it. This extra travel can occur when a pulling force is applied to tubing 20 near the front tubing grip 152. The extra aft travel allowed by frame slot 159 is enough for trigger dowels or spindles 161 to travel in slots 157. If the tension force on tubing 20 has reached the threshold level specified to deploy occluders 110, trigger dowels or spindles will be able to compress triggering spring 170, and the device 100 will trigger.

Figure 18:
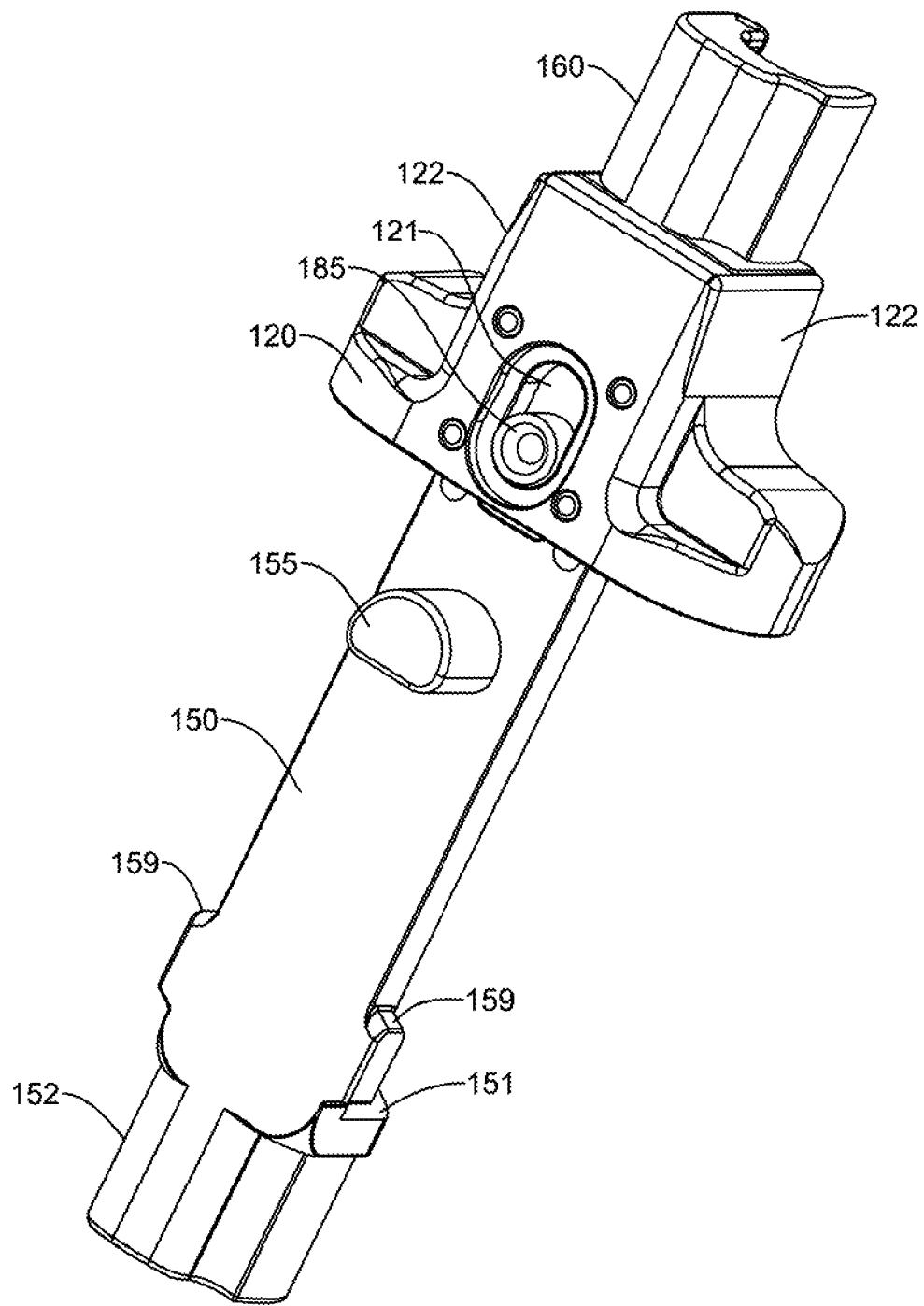
FIG. 18 is a bottom perspective view of the base unit mounted on the frame of the embodiment of FIG. 7 showing the snap fastener mount in a forward position in the base unit slot, and disposed to trigger the device upon application of a pulling force on the rear tubing grip.

Furthermore, the device 100 can trigger if a pulling force is applied to tubing 20 next to rear tubing grip 160. In this case, aft tension on tubing grip 160 (i.e. between needle 21 and tubing grip 160) and attached base unit 120 with respect to snap fastener mount 185 (which is immobilized when attached to mounting pad 180) causes the leading edge of snap fastener mount base 186 to contact the trailing edge of frame slot 159. This position is shown relative to frame slot 159 in FIG. 16, and with respect to base unit slot 121 in FIG. 18. If the tubing tension reaches the threshold force specified to trigger occluder assembly 100, then snap fastener mount 185 can push frame 150 forward, with the trigger dowels or spindles 161 overcoming and compressing triggering spring 170 to trigger occluder assembly 100. Thus in this embodiment, occluder assembly 100, appropriately immobilized on a user's body, can be triggered by a pulling force acting either on front tubing grip 152 or rear tubing grip 160.

In another embodiment, the occluder assembly 100 can trigger if an off-axis pulling force is applied to tubing 20, causing occluder assembly 100 to tend to rotate on its mounting pad 180. An off-axis pulling force can occur, for example, if the segment of tubing 20 external to occluder assembly 100 is pulled at an angle with respect to the segment of tubing 20 that is secured within occluder assembly 100. Frame post 155 (seen, e.g. in FIG. 14) can be made tall enough to extend beyond the bottom surface of actuator 130 and the female component 183 of the snap fastener. In an embodiment, the length of actuator slot 132 allows for enough forward travel of frame 150 to advance trigger dowels or spindles 161 against triggering spring 170 (as shown in FIG. 10) and trigger occluder assembly 100. Referring to FIG. 13, when frame post 155 is positioned in a trough 187 of mounting pad 180, the occluder assembly 100 can rotate clockwise or counterclockwise until frame post makes contact with cam elements 188a or 188b. An off-axis tension on tubing 20 causing occluder assembly 100 to rotate about the axis of its mounting pad attachment point (which, for example, can be a snap fastener assembly previously described) will trigger occluder assembly 100 as soon as sufficient force is applied by frame post 155 against cam elements 188a or 188b, causing frame post 155 to move forward in actuator slot 132.

Figure 12:
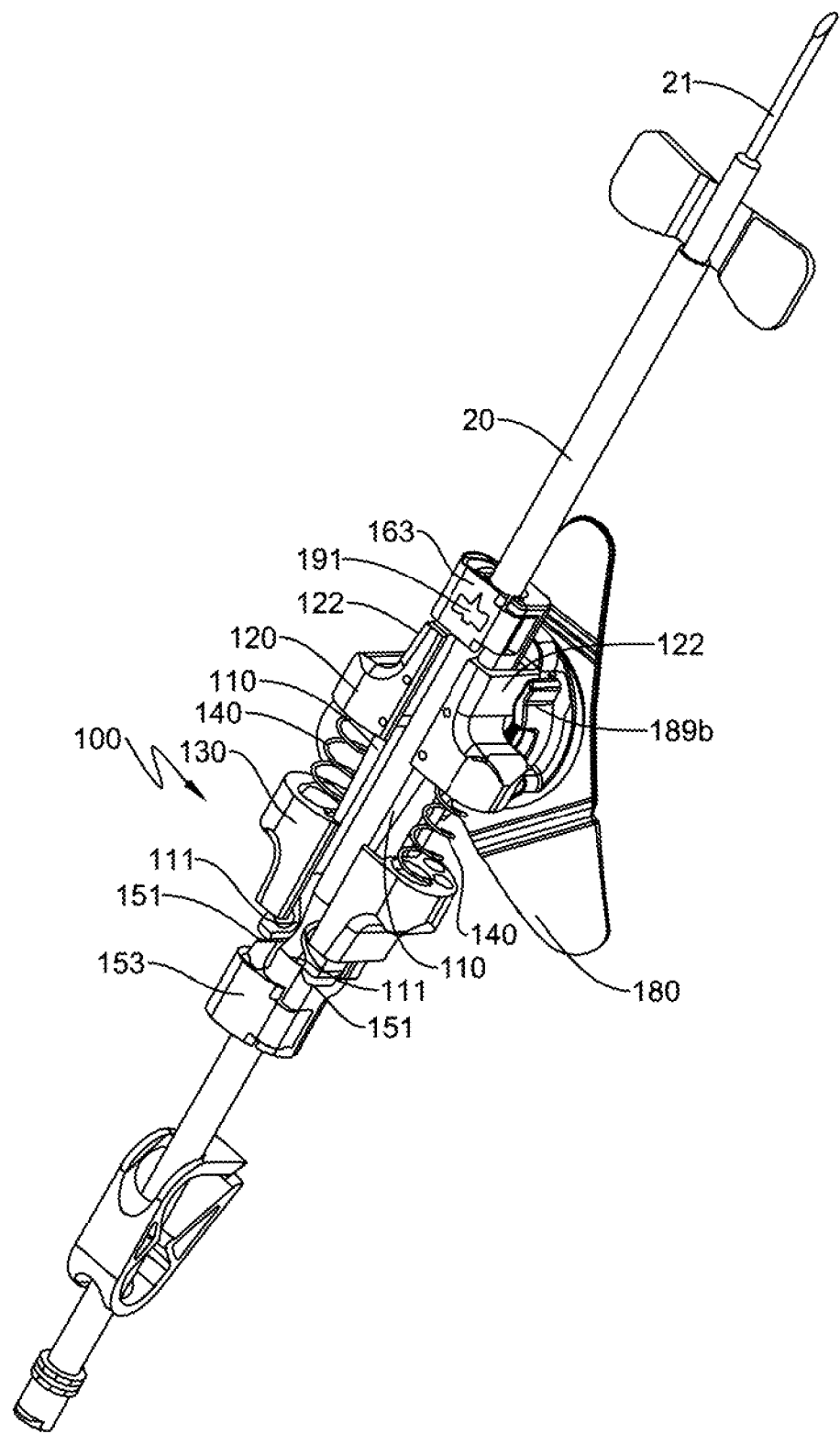
FIG. 12 is a perspective view of the embodiment of FIG. 2 shown attached to a mounting pad.

In a further embodiment, the threshold off-axis tension force on tubing 20 required to trigger occluder assembly 100 can be adjusted to approximately match the on-axis threshold tension force (i.e. when the segment of tubing 20 external to occluder assembly 100 is in line with the segment situated within occluder assembly 100). In this case, spring arms 189a and 189b on mounting pad 180 (shown in FIG. 13) are positioned to enclose the proximal narrower portion 122 of base unit 120, as shown in FIG. 12. The spring arms 189a and 189b can be constructed to have spring rates that will restrain rotation of occluder assembly 100 until an off-axis tension force on tubing 20 reaches a level equivalent to the on-axis tension force at which a triggering event is desired. Thus, it is possible to prevent premature triggering of occluder assembly 100 through contact of frame post 155 with cam elements 188a or 188b upon application of an off-axis tension on tubing 20.

Spring arms 189a and 189b can be constructed of a number of materials, including metals or plastics with tensile properties. In an embodiment, both the mounting pad 180 and spring arms 189a and 189b can be constructed from popypropylene, such as, for example, EXXON ESCORENE™ 9074). The materials from which the frame 150, actuator 130, base unit 120, occluders 110, grips 152 and 160, and latches 153 and 163 preferably may be constructed include any suitable metals or plastics with the requisite hardness to resist wearing due to contact among moving parts. In an embodiment, these components can be constructed from 6061-T6 Aluminum which has been hard-coat anodized. Preferably, actuator springs 140, triggering spring 170 and trigger dowels or spindles 161 are constructed from stainless steel or other similarly hardened material in order to resist wear and to maintain consistent functional relationships. To assist the user in mounting occluder assembly 100 onto mounting pad 180 in the proper orientation with respect to mounting pad 180, an icon 191 can be painted or inscribed onto any suitable surfaces of corresponding ends of both occluder assembly 100 and mounting pad 180. In an embodiment, a matching icon 191 is inscribed on the top surface of rear latch 163 and the rear support surface 190 of mounting pad 180.

Figure 19:
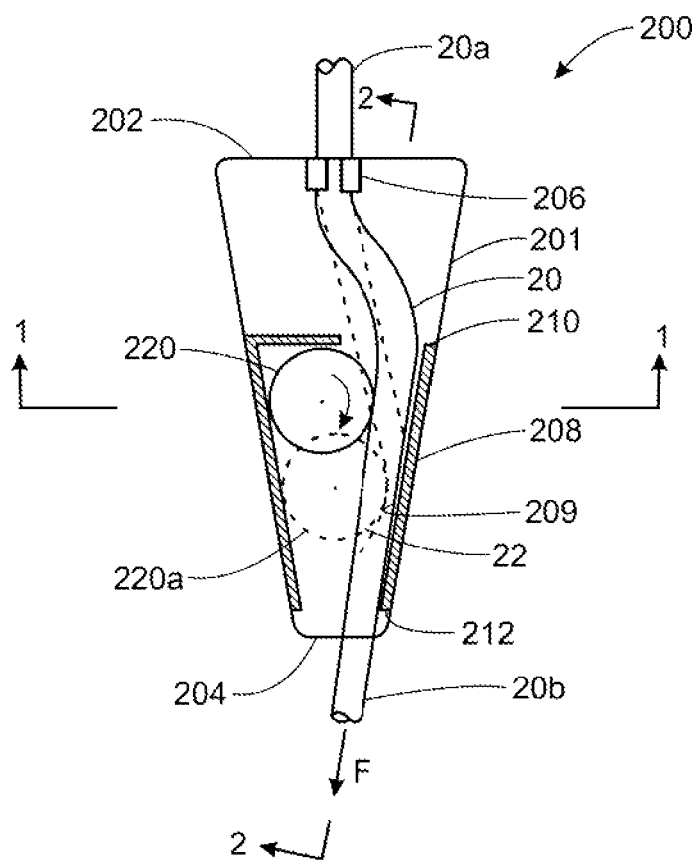
FIG. 19 is a top view of another embodiment of the invention with a flexible tube attached.

As shown in FIG. 19, another embodiment 200 of a device for occluding a flexible tube generally comprises a tapered planar body 201 having a first peripheral edge 202 and second peripheral edge 204 where the first peripheral edge is generally longer than the second peripheral edge 204. A housing 208 is attached to a top surface of the body 201. A cover to the housing is removed for clarity. The general plan dimensions of the housing 208 follow the general shape of the body 201. A first opening 210 and a second opening 212 in the housing are sized to accept the tube 20. The tube 20 having a first end 20a and a second end 20b is temporarily attached to the body 201 at a clip 206 located near the first peripheral edge 202 of the body. A cylinder or cylindroid body 220 is slideably contained within the housing and is adjacent to the tube 20 which extends from the first opening 210 to the second opening 212. Operationally, this embodiment of the device can occlude a flexible tube in response to a threshold force F acting on the tube. The threshold force F acts on the second end of the tube, thus moving the tube outwardly and away from the second opening 212. The resulting movement of the tube 20 within the housing 208 rotates the cylinder 220 to a second position 220a, thus deforming the tube 20 into an occluded position 22 against an interior wall 209 of the housing.

Figure 19A:
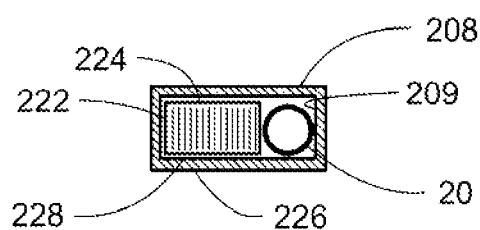
FIG. 19a is a cross-sectional view of the embodiment shown in FIG. 19 taken through FIG. 19 along the line 1-1.

FIG. 19a is a cross-sectional view of the embodiment shown in FIG. 19 taken through FIG. 19 along the line 1-1. The cylinder 220 and tube 20 are contained within the housing 208. The cylinder 220 includes a first surface 224, a second surface 226, and a peripheral edge 222. A plurality of ridges 228 can be located along the peripheral edge 222 and may be oriented generally perpendicularly to the first 224 and second 226 surfaces. Ridges 228 become adjacent to tube 20 and engage tube 20 within the housing 208, whereby longitudinal movement of tube 20 within housing 208 translates into rotational movement of cylinder 220. The interior surfaces of housing 208 can be generally smooth to allow tube 20 to slideably move within housing 208. Additionally, the first surface 224 and second surface 226 can be generally smooth to allow cylinder 220 to move slideably and/or rotationally in housing 208.

Figure 19B:
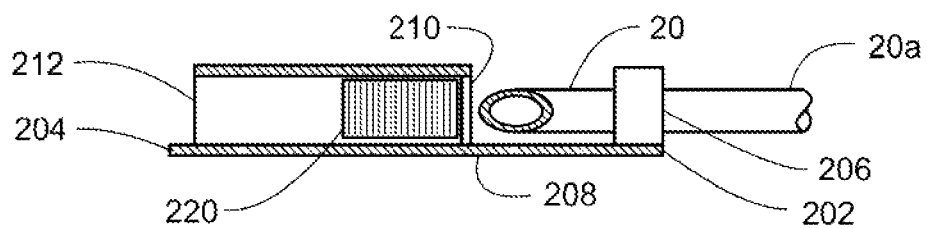
FIG. 19b is a cross-sectional view of the embodiment shown in FIG. 19 taken through FIG. 19 along the line 2-2.

FIG. 19b is a cross-sectional view of the embodiment shown in FIG. 19 taken through FIG. 19 along the line 2-2. Tube 20 is secured to body 201 by means of clip 206. Other means may be used to restrain the tube to body 201 as long as enough pulling force can be applied to the second end 20b of tube 20 to cause cylinder 220 to rotate and to compress the wall of tube 20. Additional mounting means of the tube to the body 201 may include a permanent connection between tube 20 and body 201, or a disengageable connection, allowing for reuse of the occluding device.

Figure 20:
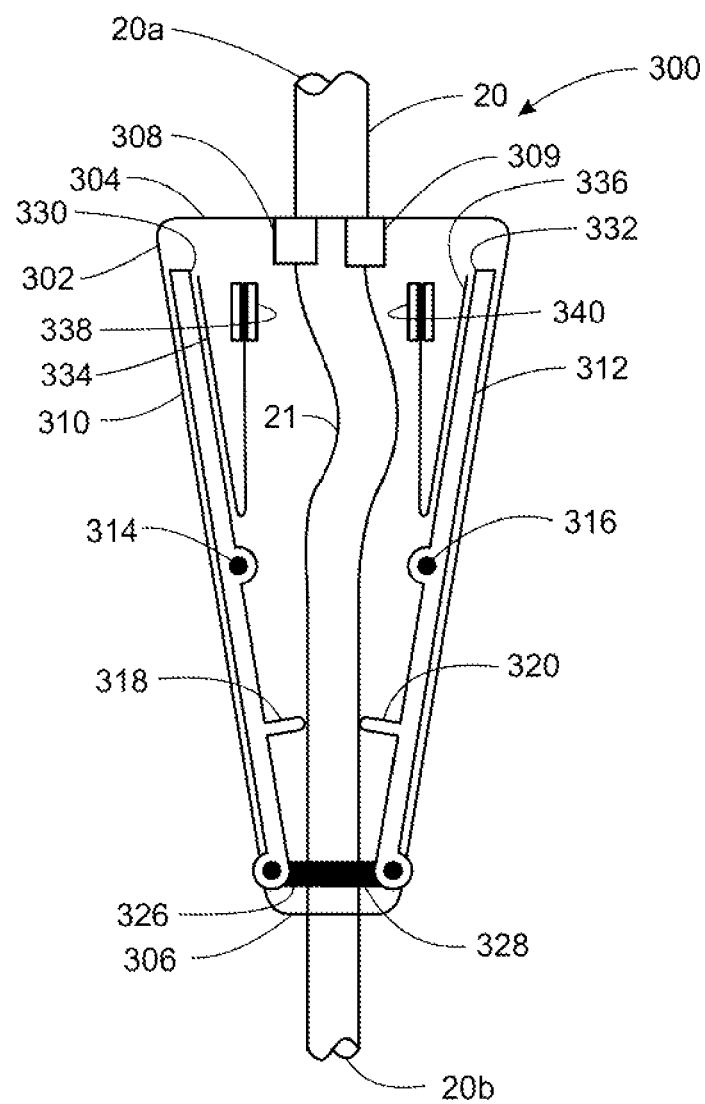
FIG. 20 is a top view of an embodiment of the invention with a flexible tube attached and a cover removed for clarity.

As shown in FIG. 20, another embodiment 300 of a device for occluding a flexible tube generally comprises a first support arm 310 and a second support arm 312. The arms being disposed between a first planar body 302 and a second planar body (the second planar body is essentially a cover; not shown for clarity). The planar bodies are generally parallel to each other. A tube 20 is positioned between the planar bodies and the support arms 310 and 312. The first planar body 302 has a first peripheral edge 304 and second peripheral edge 306.

Clips 308, 309 are located on the first planar body 302 near the first peripheral edge 304 to hold tube 20 in place. The second planar body (not shown) does not extend over the tube clips in order to assist in removing the tube from the first planar body. The support arms 310 and 312 are pivotably connected to the planar bodies by means of hinges or pivot points 314 and 316 respectively. In an embodiment, the hinges can generally be located near the midpoints of the support arms. Occluding member 318 and 320 are attached to support arms 310 and 312 respectively. The occluding members 318 and 320 extend towards each other and engage the outer surface of tube 20. Trigger arms 326 and 328 are pivotally mounted on the distal ends of support arms 310 and 312 respectively. Each trigger arm 326 and 328 can be semicircular or c-shaped, and in an opposed configuration can surround the adjacent section of tubing 20, the inside edges of the arms lightly in contact with the sides of the tubing. The opposing legs of the trigger arms 326 and 328 are in contact when they are generally perpendicular to the longitudinal axis of the tubing 20. When the distal ends of the trigger arms engage each other and tube 20, occluding arms 318 and 320 do not occlude the tube 20. In a first position 21, the tube 20 is provided with an amount of slack for strain relief between clips 308/309 and occluding members 318/320. While tube 20 is in the first position 21, the trigger arms 326 and 328 are generally perpendicular to the longitudinal axis of the tube 20 and the tube 20 remains unoccluded.

As shown in FIG. 20, a first spring 334 provides a compressive force against a first contact surface 330 of the first support arm 310. Similarly, a second spring 336 provides a similar force against a second contact surface 332 of the second support arm 312. The springs 334 and 336 are attached to the first planar body by spring clips 338 and 340 respectively. The springs are generally the same size and provide the same amount of force to each arm. The springs are shown as leaf springs, but may be any type of elastic element (such as, e.g., coil springs) capable of providing the force necessary to occlude tube 20. While trigger arms 326 and 328 are generally perpendicular to the axis of tube 20 and in contact with one another, springs 334 and 336, are prevented from occluding the tube. However, when the trigger arms are rotated to a second position (as shown in FIG. 21) the springs 334 and 336 provide the force necessary to occlude the tube 20 by pinching the tube between the pair of occluding members 318 and 320.

Figure 21:
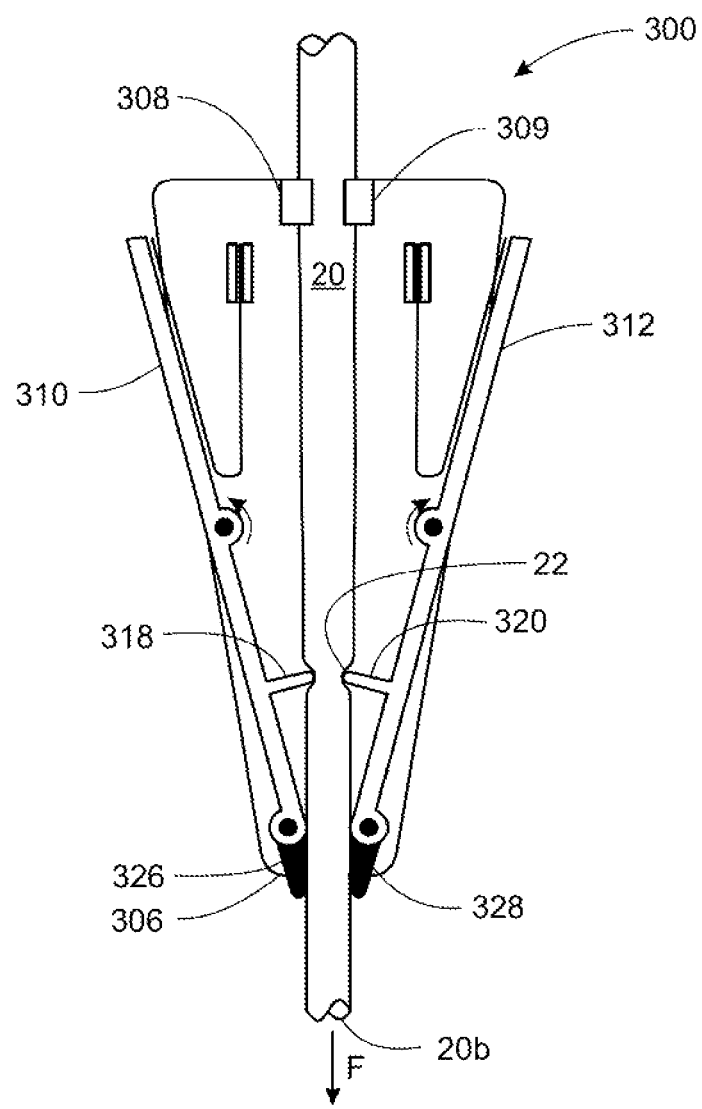
FIG. 21 is a top view of the embodiment shown in FIG. 20 with a flexible tube attached and shown in an occluded position.

As shown in FIG. 21, the embodiment 300 is shown in an occluded position. When a predetermined threshold force F acts on the second end 20b, the slack 21 in tube 20 is removed and the tube generally moves towards the second peripheral edge 306. Since triggering arms 326 and 328 engage the tube, a longitudinal movement of tube 20 acts to rotate arms 326 and 328. The rotation of the triggering arms leads to the rotation of the support arms 310 and 312; and under the force of springs 324 and 326, occluding members 318 and 320 apply an occlusive force against the sides of tube 20.

Figure 22:
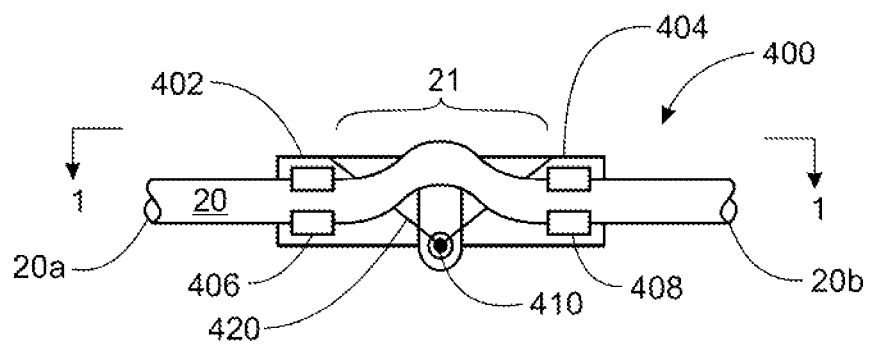
FIG. 22 is a top view of an embodiment of the invention with a flexible tube attached.
Figure 23:
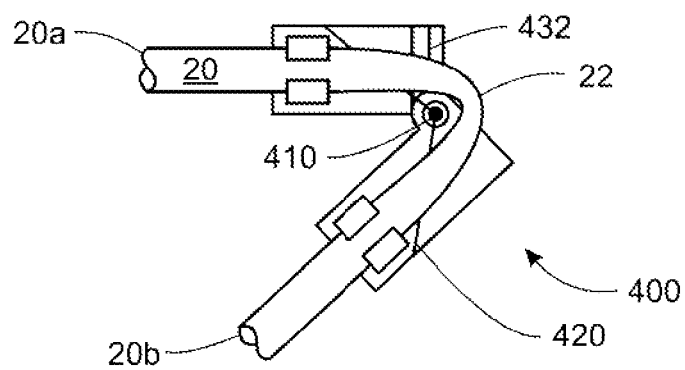
FIG. 23 is a top view of the embodiment shown in FIG. 22 with a flexible tube attached and shown in an occluded position.
Figure 24:
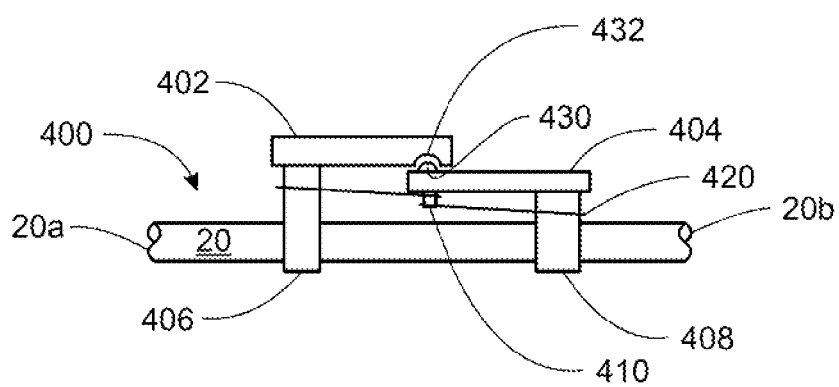
FIG. 24 is side view of the embodiment shown in FIG. 22 taken along line 1-1 of FIG. 22.

As shown in FIG. 22, another embodiment 400 of a device for occluding a flexible tube generally comprises two bodies 402 and 404 pivotally connected by a central hinge 410. A first clip 406 is mounted to body 402 and second clip 408 is mounted to body 404 to hold the tube 20 in a first position 21 between the clips. Strain relief is provided when the tube 20 is in the first position 21 in order for the tube to properly occlude as shown in FIG. 23. A spring 420 is rotatably connected to the hinge 410 where it is compressed between the clips 406 and 408 and held in compression by a tongue 430 and groove 432 shown in FIG. 24. The bodies are held in the first position by the tongue and groove connection as shown in FIGS. 22 and 24 until a predetermined force F is applied to a first end 20a and a second end 20b of the tube. The force F results in a rotational force about the hinge 410. When the rotational force overcomes the resistance of the tongue 430 and groove 432 connection, the spring decompresses and moves the tube into a second position 22 as shown in FIG. 23.

Figure 25:
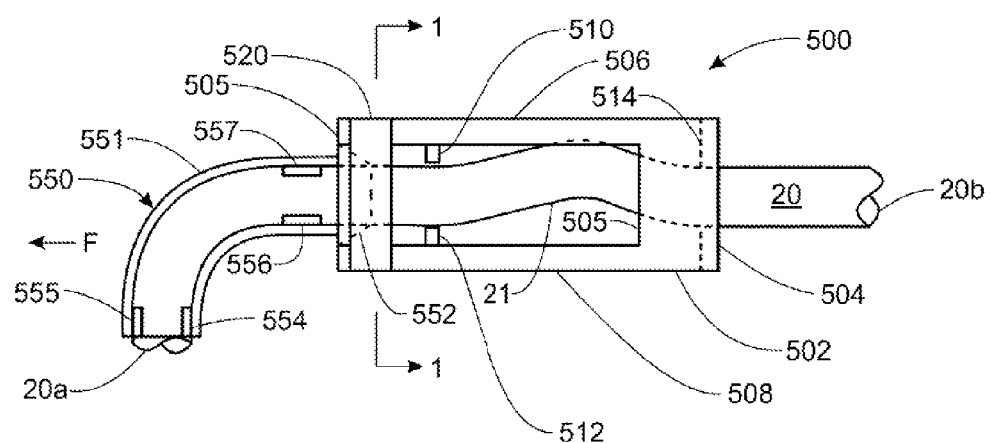
FIG. 25 is a top view of an embodiment of the invention with a flexible tube attached.

As shown in FIG. 25, another embodiment 500 of a device for occluding a flexible tube generally comprises a hollow cylindrical body 502 having a first circular edge 504 and a second circular edge 505 located at opposite ends of the body. Semicircular arms 506 and 508 are connected to and extend away from the second peripheral edge 505. An elastic actuating member 520 is located at the distal ends of the arms 506 and 508 and is capable of deflecting the distal ends of the arms toward each other. Actuating member 520 may alternatively be any element that exerts a spring-like force to compress the distal ends of arms 506 and 508 toward each other, such as, for example, a metallic spring clip. The arms 506 and 508 are capable of bending towards each other resulting in the occlusion of the tube 20 and then returning to their original position. A first occluding member 510 and a second occluding member 512 are attached to the first arm 506 and the second arm 508 respectively. The occluding members 510 and 512 are rigid and capable of occluding the tube 20 when the elastic actuating member 520 deflects the arms 506 and 508 towards each other. Tube 20 can be secured to the cylindrical body near the first circular edge 504 by a clamp 514 disposed within the cylindrical body 502. Clamp 514 holds the tube 20 securely to the body. Preferably, tube 20 is generally centered along the longitudinal axis of the embodiment 500. A curved bracket 550 can be secured to tube 20 near the distal ends of arms 506 and 508. A tapered head 552 of curved bracket 550 can slideably engage the inside surface of first arm 506 and second arm 508 so as to resist the elastic actuating member 520 from occluding the tube 20. In an unoccluded position 21, the tube is provided with a predetermined amount of strain relief while the tapered head 552 is positioned between the distal ends of first arm 506 and second arm 508.

Figure 27:
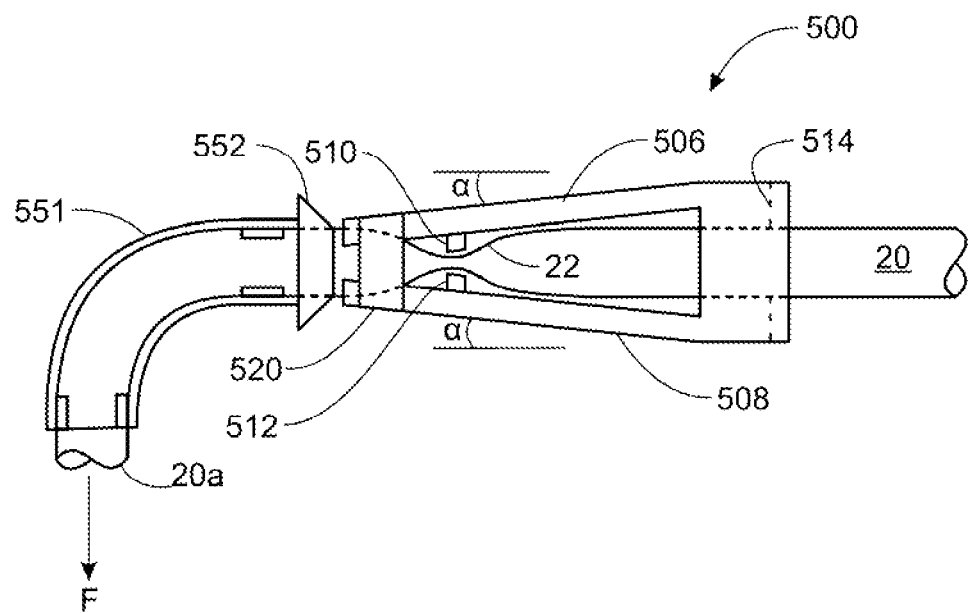
FIG. 27 is a top view of the embodiment shown in FIG. 25 with a flexible tube attached and shown in an occluded position.

As shown in FIG. 27, once a threshold force F is applied to a first end 20a of tube 20, the tapered head 552 is urged outwardly and away from the distal ends of the first arm 506 and second arm 508 by the elastic actuating member 520, resulting in the occluding members 510 and 512 deforming the tube into a second position 22 where flow is obstructed. At that time, the strain relief provided in the unoccluded position 21 is generally removed from the tube and the arms 506 and 508 deflect an angle α whereby the tube 20 is deformed into a second position 22.

Figure 25A:
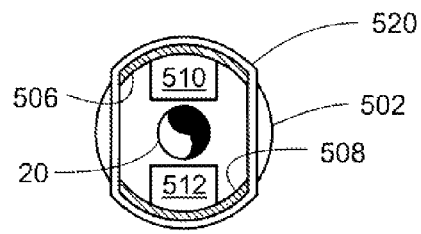
FIG. 25a is a cross-sectional view of the embodiment taken along the line 1-1 of FIG. 25.

FIG. 25a shows a cross-sectional view of the embodiment taken along the line 1-1 of FIG. 25. The first occluding member 510 and second occluding member 512 are adjacent to opposite sides of the tube shown in the unoccluded state. The elastic actuating element 520 provides a compressive force to the first arm 506 and second arm 508.

Figure 26:
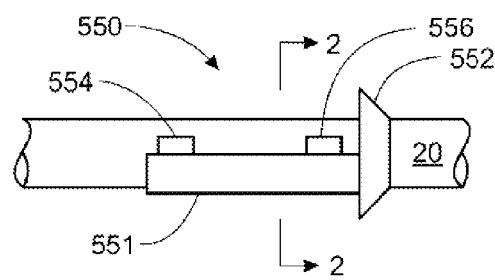
FIG. 26 is a side view of a trigger of the embodiment shown in FIG. 25 with a flexible tube attached.
Figure 26A:
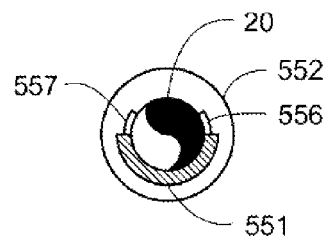
FIG. 26a is a cross-sectional view of the trigger taken through FIG. 26 along the line 2-2.

FIG. 26 shows a side view of a trigger of the embodiment shown in FIG. 25 with a flexible tube attached therein. The bracket 550 is comprised of a curved support section 551 attached to a tapered cylindrical head 552. Curved tabs 554-557, extend outwardly from the support section 551 and are configured to keep the tube in contact with the support section. The inside perimeter of the tapered head 552 is generally in full contact with the outside perimeter of the tube. The head 552 tapers away from the curved support section 551 so that it is urged away from the first arm 506 and second arm 508 when a threshold force F is applied to the first end 20a of the tube in the direction indicated. Additionally, FIG. 26a is a cross-sectional view of the trigger taken through the line 2-2 of FIG. 26.

Figure 28:
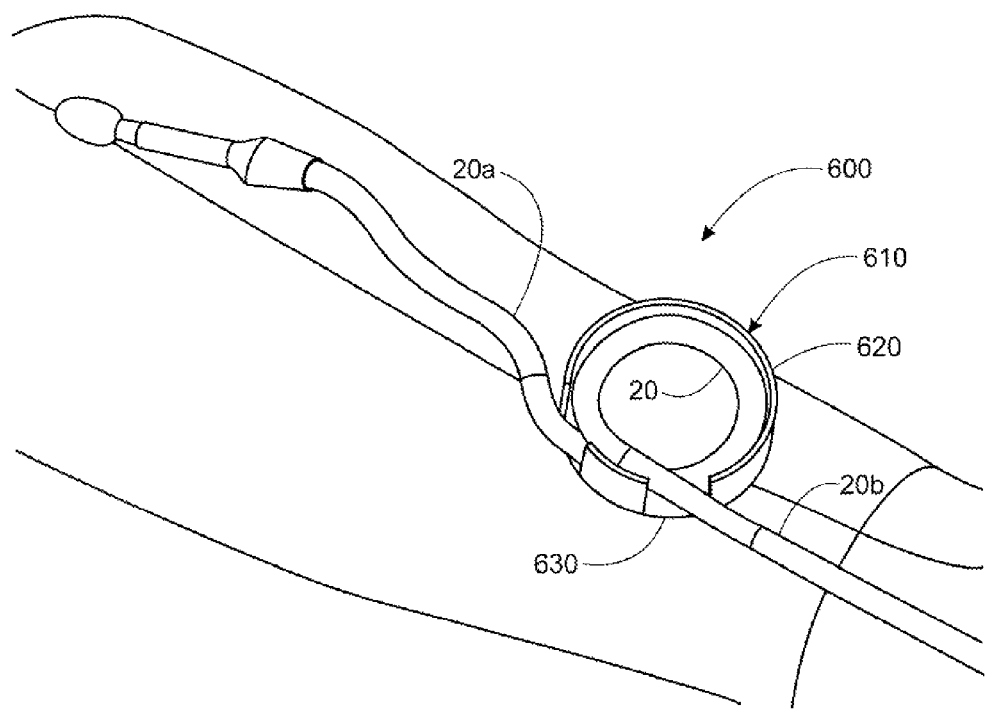
FIG. 28 is a perspective view of an embodiment of the invention with a flexible tube attached and a top surface of the embodiment not shown for clarity.

As shown in FIG. 28, another embodiment 600 of a device for occluding a flexible tube generally comprises a cylindrical housing 610 having a top surface (not shown for clarity), bottom surface 630, and a curved peripheral edge 620. A single loop of tube 20 having a first end 20a and second end 20b is fully enclosed within the housing 610.

Figure 29:
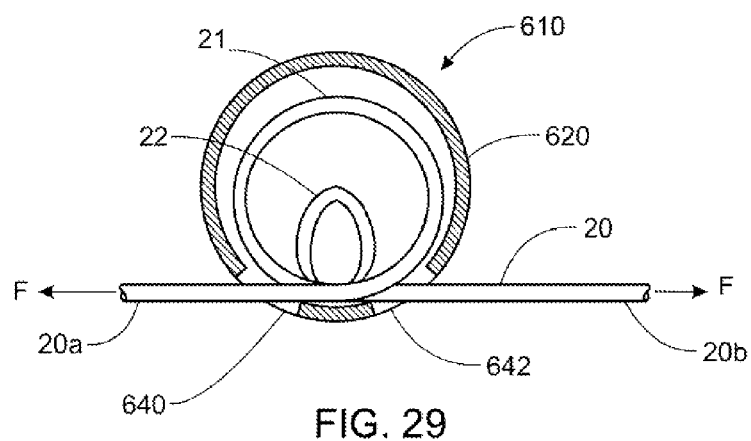
FIG. 29 is a plan view of the embodiment shown in FIG. 28 with a flexible tube shown in both an occluded and unoccluded position.

FIG. 29 shows the tube in a first position 21 and second position 22. The tube enters the housing 610 through a first opening 640 along the curved peripheral edge 620 and exits in a similar manner through a second opening 642. While in the first position 21, the tube is unoccluded and flow within the tube is unobstructed. However when a threshold force, F, is applied to either the first end 20a or second end 20b of the tube, the tube is deformed, or kinks, within the housing to a second position 22, and fluid flow within the tube is restricted.

Figure 30:
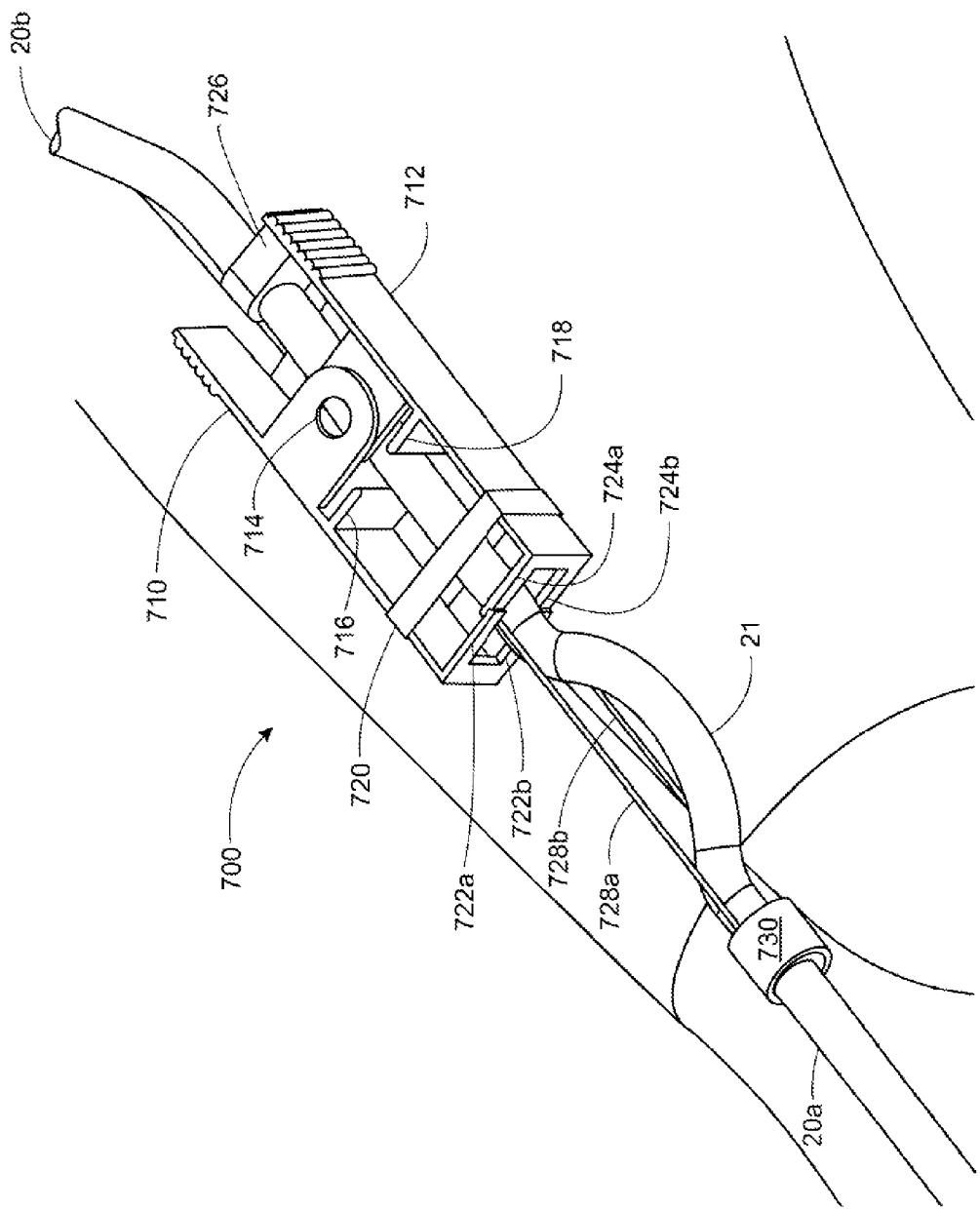
FIG. 30 is a perspective view of an embodiment of the invention with a flexible tube attached.

As shown in FIG. 30, and in top view in FIG. 31, another embodiment 700 of a device for occluding a flexible tube generally comprises a first arm 710 and second arm 712 pivotally connected by a hinge 714. A flexible tube 20 is secured to the second arm 712 by a clip 726 and is disposed between the length of the two arms. A first pair of trigger arms 722a and 722b is located on the first arm 710 on opposite sides of the tube 20. Similarly, a second pair of trigger arms 724a and 724b is located on the second arm 712. The distal end of the first trigger arm 722a and 722b engage a notch on the distal end of the second trigger arm 724a and 724b. The notch resists the compressive force of an elastic actuating element 720 located around the arms 710 and 712. A pair of rods 728a and 728b extend outwardly and away from trigger arms 722a and 722b respectively. The distal ends of the rods are each connected to a tube clamp 730. The tube clamp 730 is securely fastened to the flexible tube 20 near the first end 20a of the tube to minimize any slippage between the tube 20 and the clamp 730. Strain relief 21 is provided between the tube clamp 730 and clip 726. Such relief allows axial movement of tube 20 between clamp 730 and clip 726 without pulling on the clip 726.

As shown in FIG. 32, movement of the clamp 730 away from the trigger arms is translated along the rods 728a and 728b resulting in deflection of the first trigger arms 722a and 722b away from the second trigger arms 724a and 724b. Once the distal ends of the first trigger arms 722a and 722b move beyond the notch on the second trigger arms 724a and 724b, the elastic actuating element 720 rotates the first arm 710 about the hinge 714 an angle α. This rotation brings the occluding members 716 and 718 closer together thus pinching a section 22 of tube as shown in FIG. 32.

Figure 33:
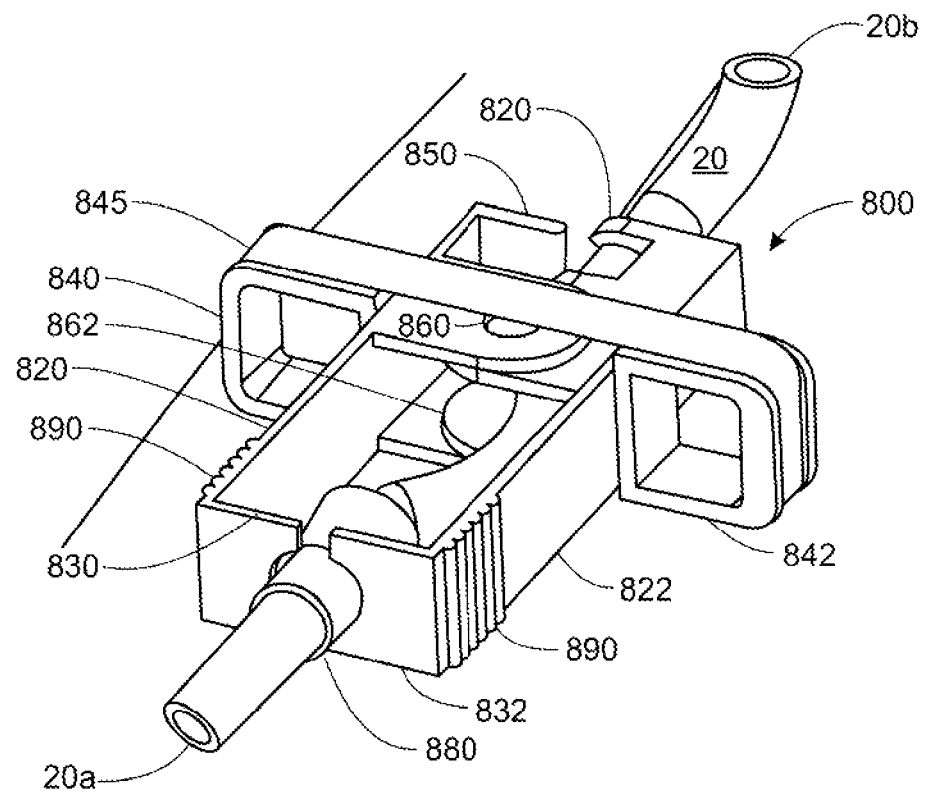
FIG. 33 is a perspective view of an embodiment of the invention with a flexible tube attached.
Figure 35:
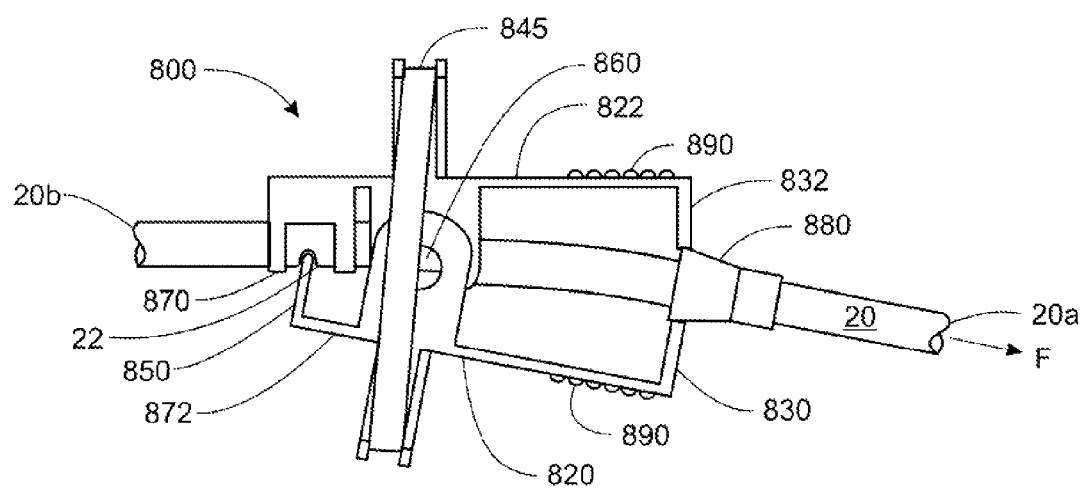
FIG. 35 is a top view of the embodiment shown in FIG. 33 with a flexible tube in an occluded position.

As shown in FIG. 33, another embodiment 800 of a device for occluding a flexible tube 20 generally comprises a first arm 820 and second arm 822 pivotally connected by hinges 860 and 862. A tube 20 having a first end 20a and second end 20b is releasably attached to clips 870 and 872. The tube 20 is disposed between the first and second arms and between the first hinge 860 and second hinge 862. An elastic force actuator 845 is stretched over a first support member 840 and second support member 842, the support members 840 and 842 are attached to the first arm 820 and second arm 822 respectively. The support members keep the elastic actuator 845 from slipping when the arms 820 and 822 are pivoted about the hinges 860 and 862 as shown in FIG. 35. A plurality of ribs 890 can be positioned along the outer surface of the arms 820 and 822 as gripping surfaces in order to assist in rotating the arms about hinges 860 when the device is returned to an unoccluded position.

Figure 34:
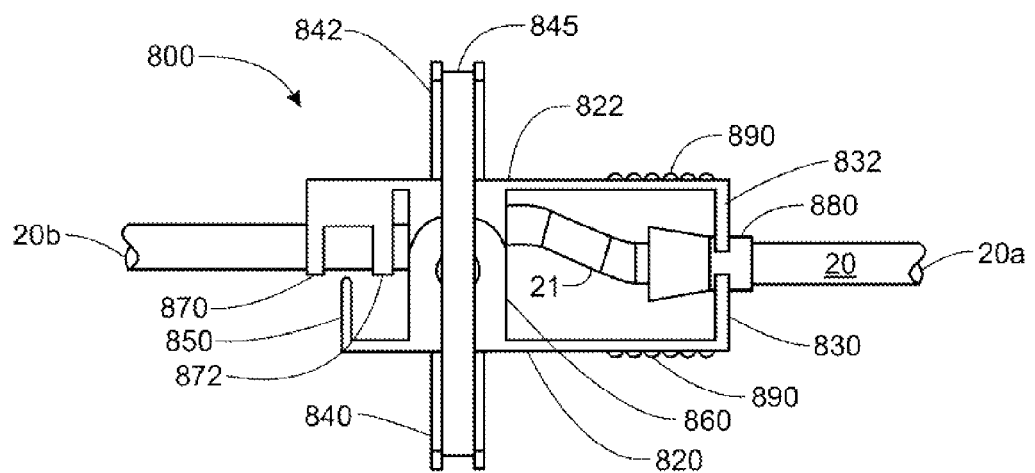
FIG. 34 is a top view of the embodiment shown in FIG. 33 with a flexible tube in an unoccluded position.

As shown in FIG. 34, while in a first position 21, the arms 820 and 822 are generally parallel to each other and the elastic actuator 845 generates approximately zero moment about the hinges. However, when the arms 820 and 822 are rotated towards each other, the elastic actuator 845 generates a moment about the hinges. An occluding member 850 is located at the distal end of the first arm 820 located opposite the trigger arm 830. The occluding member 850 is generally perpendicular to the tube 20 so as to occlude the tube 20 when a threshold force F is applied to the first end 20a as shown in FIG. 35. Supporting the tube 20 near the occluding edge is a pair of clips 870 and 872. The clips allow the tube 20 to be releasably attached to the second arm 822. A tapered head 880 is attached to the tube near the first end 20a. The tapered head 880 is generally cylindrical in shape and slideably engaged to the distal ends of the trigger arms 830 and 832. While in the first position 21, the narrowest part of the tapered head 880 is located between the trigger arms 830 and 832.

As shown in FIG. 35, when a threshold force F is applied to the first end 20a, the tapered head 880 moves outwardly and away from the trigger arms 830 and 832 resulting in the arms being urged open. As the trigger arms 830 and 832 separate, the occluding edge 850 occludes the tube 20 near the second end 20b. After the embodiment of the device has been triggered and the tube 20 is in the second position 22, and may be returned to the first position 21 by sliding the tapered head 880 so that the narrowest portion of the tapered head 880 is positioned between the trigger arms 830 and 832. By sliding the tapered head 880 towards the trigger arms a predetermined amount of strain relief 21 will be created in the tube 20 between the tapered head 880 and the pair of clips 870 and 872. The strain relief is required so that a force F can slide the tapered head 880 a certain distance without excessive straining on the tube 20.

Figure 36:
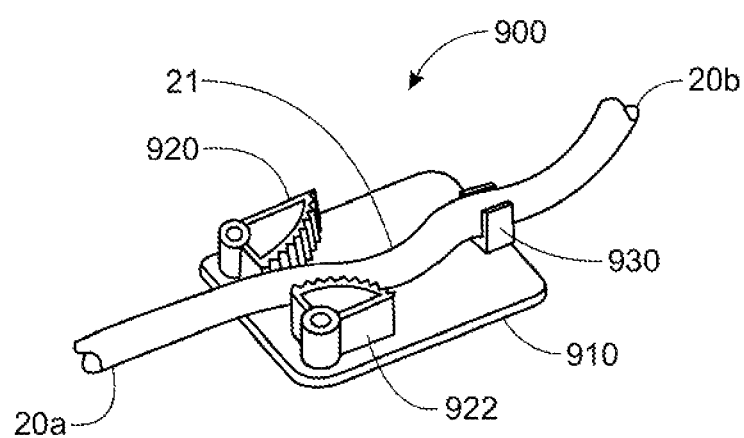
FIG. 36 is a perspective view of an embodiment of the invention with a flexible tube attached.
Figure 37:
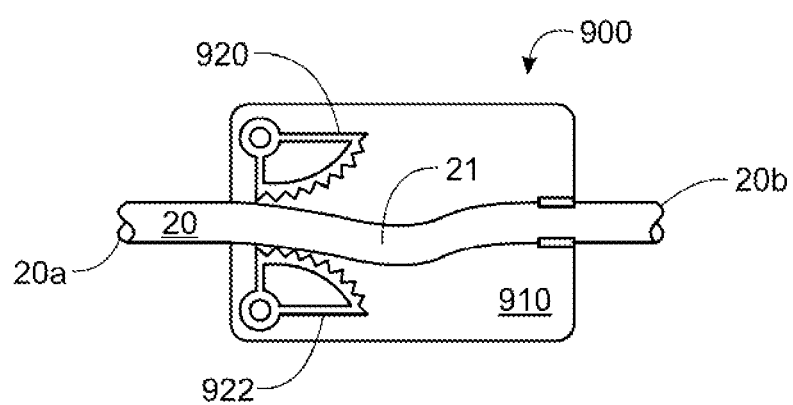
FIG. 37 is a top view of the embodiment shown in FIG. 36 with a flexible tube in an unoccluded position.

As shown in FIG. 36, another embodiment 900 of a device for occluding a flexible tube 20 generally comprises a base 910 having a pair of eccentric or cam-shaped bodies 920 and 922 rotatably mounted on one side of the base 910. In the exemplary embodiment, the bodies 920, 922 have an eccentric peripheral edge with a gripping means capable of frictionally engaging an adjacent tube 20. The gripping means may be a plurality of ridges and grooves oriented perpendicular to planar surface of the base. The flexible tube 20 is disposed between the bodies 920 and 922 and releasably attached to the opposite side of the base with a clip 930. The tube 20 may be releasably attached by any means so long as it resists the tube 20 from sliding in the clip and does not occlude the tube while restrained. The bodies 920, 922 are shaped so that the gripping means engages the adjacent tube 20 but does not create an occlusion condition while the tube 20 in is a first position 21 as shown in FIGS. 36 and 37.

Figure 38:
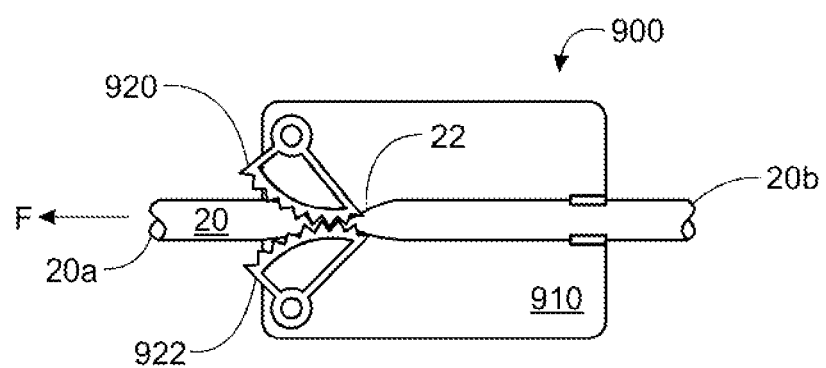
FIG. 38 is a top view of the embodiment shown in FIG. 36 with a flexible tube in an occluded position.

As shown in FIG. 38, when a force F is applied to a first end 20a the tube 20 moves outwardly and away from the base 910 but is restrained by the clip 930. While moving, the tube 20 then engages the gripping means and rotates the eccentric bodies towards each other. The eccentric members rotate in a cam fashion, thereby deforming the tube 20 into a second occluded position 22. The tube 20 may be returned into the unoccluded first position 21 if first end 20a is moved towards clip 930 so that bodies 920 and 922 rotate away from each other to a predetermined position which allows the flow in the tube 20 to be unrestricted.

Figure 39:
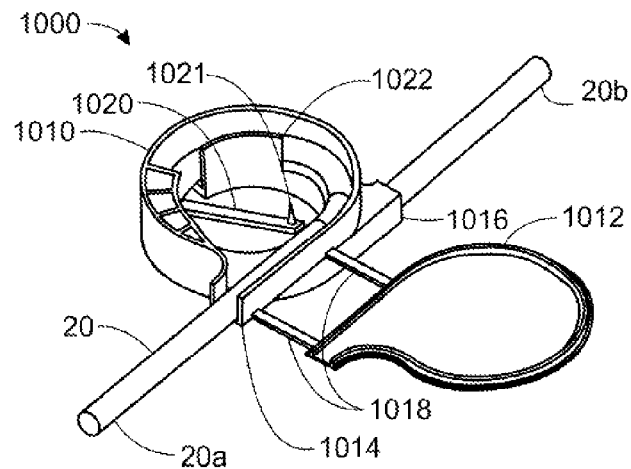
FIG. 39 is a perspective view of an embodiment of the invention with a flexible tube attached.
Figure 40:
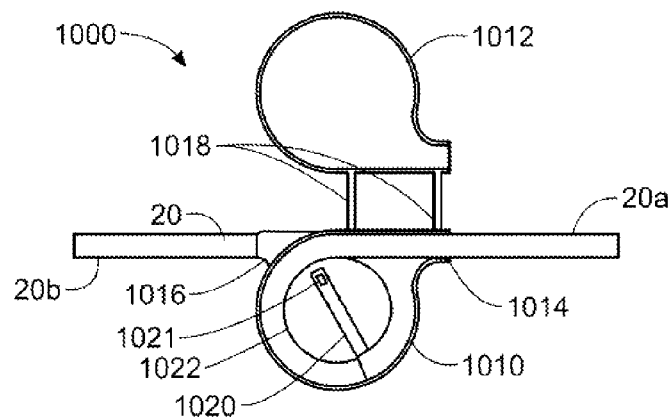
FIG. 40 is a top view of the embodiment shown in FIG. 39 with a flexible tube attached in an unoccluded position.
Figure 41:
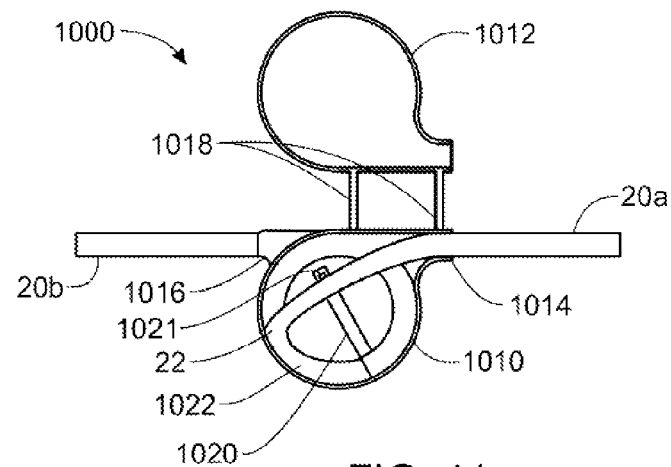
FIG. 41 is a top view of the embodiment shown in FIG. 39 with a flexible tube attached in an occluded position.

As shown in FIGS. 39, 40 and 41, another embodiment 1000 of a device for occluding a flexible tube 20 generally comprises a cylindrical housing 1010 having a sloped internal surface for supporting a single loop of a tube 20 (this embodiment is essentially a refinement of embodiment 600 found in FIG. 28). The single loop of tube is fully enclosed within the housing 1010. The tube 20 enters the housing 1010 at a first opening 1014, forms a single unoccluded loop along the sloped internal surface and exits the housing 1010 at a second opening 1016. A cover 1012 is attached to the housing 1010 by means of two flexible tabs 1018. An occluding edge 1022 extends from the sloped internal surface to the cover 1012. A flexible arm 1020 having a pointed tab 1021 extends from the sloped surface to a predetermined position below the cover 1012. The tab 1021 does not engage the tube 20 while the tube 20 is in an unoccluded position as shown in FIGS. 39 and 40.

As shown in FIG. 41, when a threshold force F is applied to the first end 20a of the tube, a portion of the tube moves outwardly and away from the first opening 1014. The arm 1020 is configured to deflect away from the tube 20 so that the tab 1021 may engage and hold the tube 20 in an occluded position 22. The tube 20 is bent around the occluding edge 1022 and held in position 22 until the arm 1020 is deflected so the tube 20 may return to its unoccluded position as shown in FIGS. 39 and 40. The sloped surface provides a means for supporting and shaping the tube 20 so that when a force F is applied, the tube 20 is able to deflect about the occluding edge without moving relative to the second opening 1016.

Figure 42:
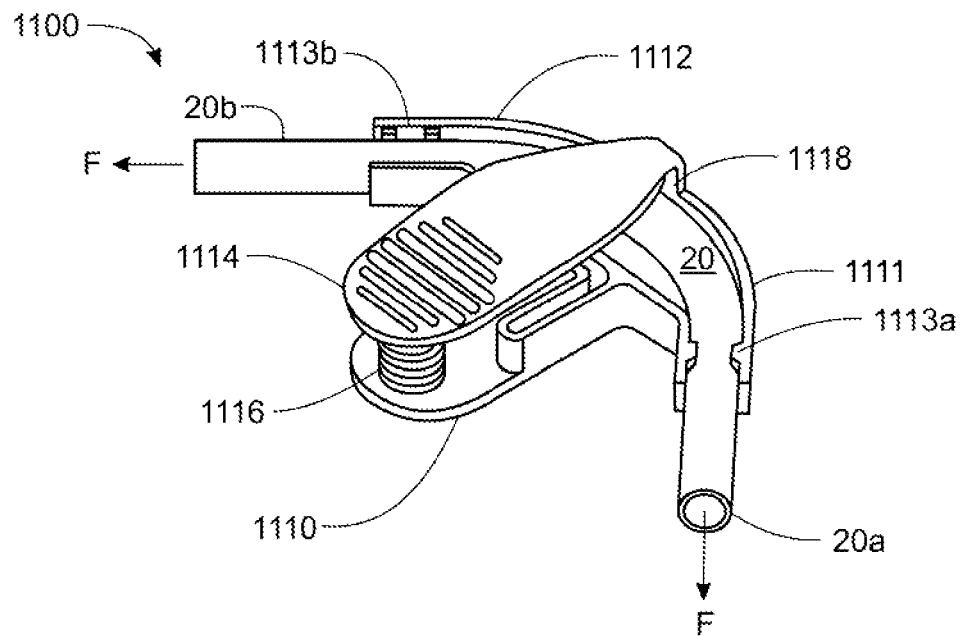
FIG. 42 is a perspective view of an embodiment of the invention with a flexible tube attached.
Figure 44:
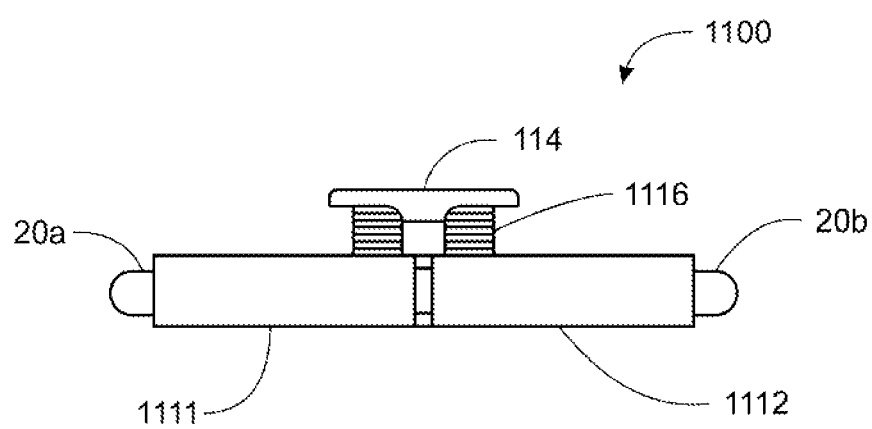
FIG. 44 is a front view of the embodiment shown in FIG. 42 with a flexible tube attached in an unoccluded position.

As shown in FIG. 42, another embodiment 1100 of a device for occluding a flexible tube 20 generally comprises a base 1110 pivotally connected to an occluding member 1114 having an edge 1118 for occluding a tube 20. A spring 1116 is compressed between the base 1110 and occluding member 1114, whereby the occluding member 1114 is urged to rotate about a central hinge 1120. The tube 20 having a first end 20a and second end 20b is secured to a first arm 1111 by a clip 1113a and a second arm 1112 also by a clip 1113b. The arms 1111 and 1112 are generally symmetrical to each other and are able to rotate away from the base 1110. In an unoccluded position, as shown in FIGS. 42 and 44, the front edge of the occluding member 1114 is supported by the top surfaces of members 1112 and 1111 while they are positioned relatively close together with just a small gap between them.

Figure 43:
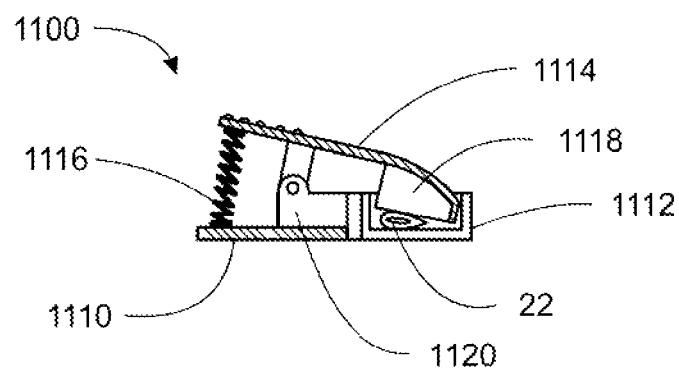
FIG. 43 is a cross-sectional view of the embodiment shown in FIG. 42 with a flexible tube attached in an occluded position.

As shown in FIG. 43, when a threshold force F pulls on the first and second ends of the tube the arms 1111 and 1112 rotate apart from each other and away from the base 1110. Once the arms rotate away from each other, the gap between them increases and the occluding member 1114 no longer rests on the arms, and is urged by the spring 1116 to occlude the tube 20. By compressing the spring 1116 and resting the occluding member 1114 on the arms 1111 and 1112 in their original positions, the tube 20 will return to its unoccluded position.

Figure 45:
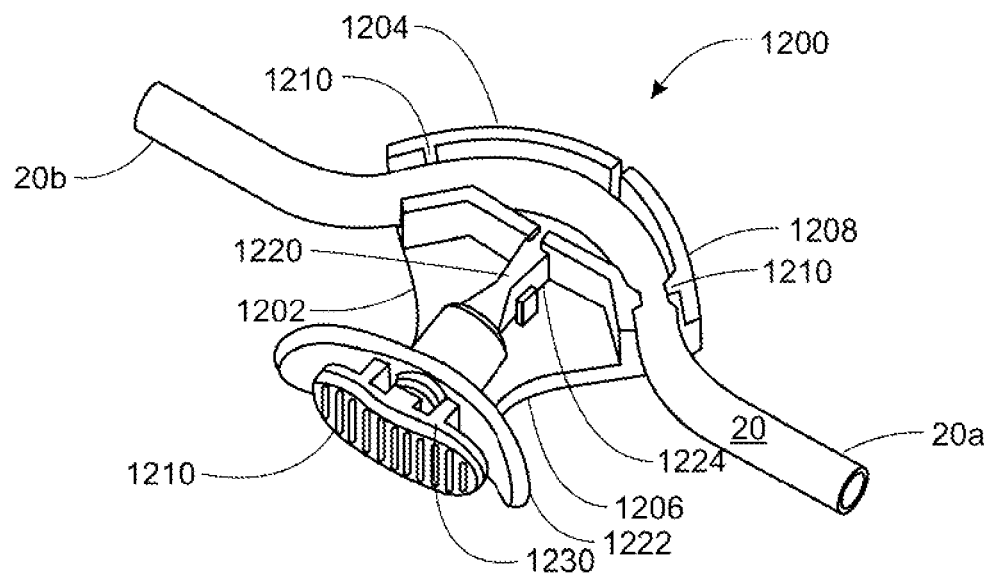
FIG. 45 is a perspective view of an embodiment of the invention with a flexible tube attached.
Figure 46:
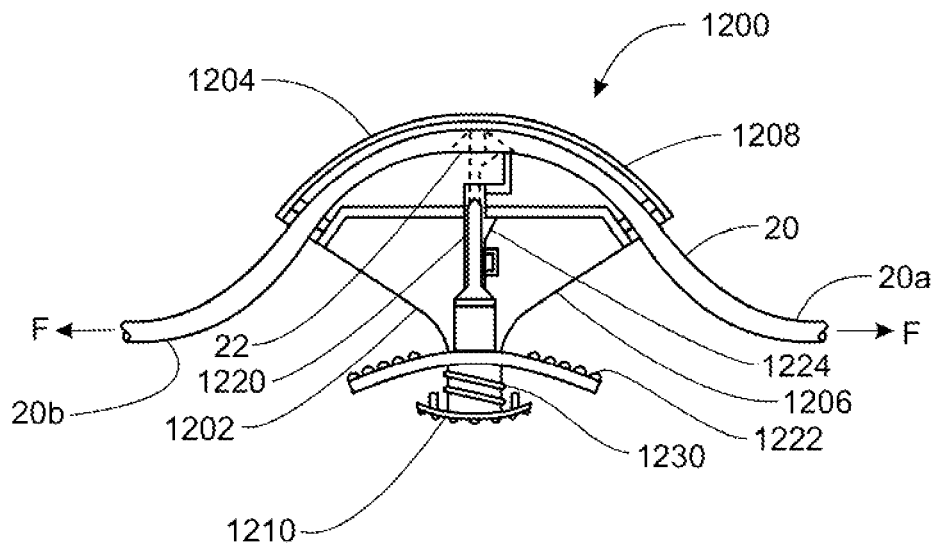
FIG. 46 is a cross-sectional view of the embodiment shown in FIG. 45 with a flexible tube attached in both an unoccluded position and occluded position.

As shown in FIGS. 45 and 46, another embodiment 1200 of a device for occluding a flexible tube generally comprises a first body 1202 having a generally planar surface; a second body 1206 pivotably attached to the first body 1202; a plunger 1220 slideably attached to the first body 1202; and compression spring 1230 positioned between the plunger and the first body. A first channel 1204 having two curved sidewalls for positioning a tube 20 therebetween is located at one end of the first body 1202, while a curved member 1210 is attached to the opposite end of the first body 1202. Additionally, a plunger 1220 is slideably mounted on the first body 1202 where the compression spring 1230 provides the force necessary to move the plunger 1220 into the first channel 1204 and occlude the tube located therein.

As shown in FIGS. 45 and 46, in a first position, the spring 1230 is compressed against the curved member 1210 and the plunger 1220. It is restrained by a tab 1224 extending from the plunger 1220 where it engages the sidewall of a second channel 1208. A threshold force F acting on a first end 20a and second end 20b of the tube 20 urges a second channel 1208 to rotate away from a first channel 1204. The plunger 1220 is held in place by the tab 1224 until a second member 1206 moves away from a first member 1202 thus releasing the plunger 1220 by means of the compression spring 1230 into the first channel 1204 and deforming the tube 20 into a second position 22 as shown in FIG. 46. The tube 20 is releasably attached within the first and second channels 1204, 1208 by means of clips 1210 located near the entrance of each channel. The tube 20 is slightly bent curved within the channels to allow free movement of the tube 20 between the clips when the force F acts on the first and second ends 20a, 20b of the tube 20. The tube 20 may be unoccluded by compressing the spring 1230 and engaging the tab 1224 with the second member in order to hold the spring in compression.

Figure 47:
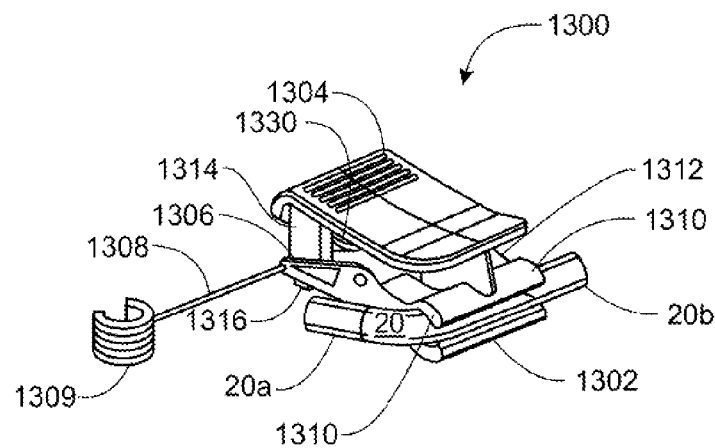
FIG. 47 is a perspective view of an embodiment of the invention with a flexible tube attached.
Figure 52:
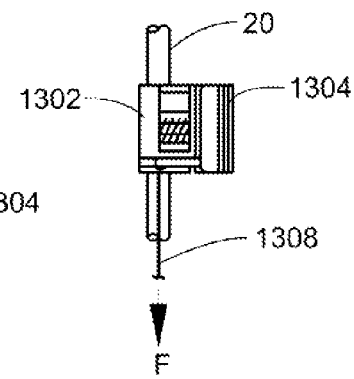
FIG. 52 is a side view of the embodiment along line 3-3 of FIG. 48 with a flexible tube attached shown in an occluded position.

As shown in FIG. 47, another embodiment 1300 of a device for occluding a flexible tube 20 generally comprises a first body 1302 having an arm 1306 extending rearward from the first body; a second body 1304 pivotably attached the first body by means of a hinge (not shown), the second body having an occluding edge 1312; a rod 1308 is attached to the distal end of the arm 1306 and extends outwardly and away from the arm; a clamp 1309 is affixed to the distal end of the arm configured to be releasably connected to a first end 20a of a tube 20. A pair of clips 1310 extend from the first body 1302 and securely hold the tube 20 against the first body 1302. The clips 1310 are separated by a predetermined distance to allow the occluding edge 1312 to pass between them without touching the clips 1310. An extension 1314 projects outwardly and away from the second body 1304. It is received between the first body 1302 and arm 1306 so that a tab 1316 engages the arm and holds the spring 1330 in compression. While the spring 1330 is in compression, the occluding edge does not occlude the tube 20. However, when a threshold force F is applied to the first end 20a of the tube 20 it moves the clamp 1309, the rod 1308 and the arm 1306 away from the first body 1302. The outward movement of the arm 1306 triggers the spring to decompress since the tab 1316 no longer engages the arm 1306 as shown in FIG. 52. The expansion of the spring 1330 moves the occluding edge into the tube 20, thus occluding the tube 20.

Figure 48:
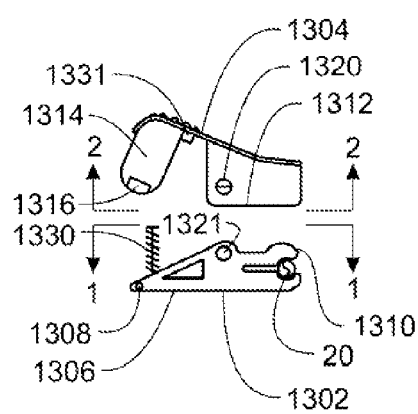
FIG. 48 is an exploded side view of the embodiment shown in FIG. 47 with a flexible tube attached.

FIG. 48 is a side view of the embodiment 1300 with the first body 1302 and second body 1304 separated for clarity. Pins 1320 are located on each side of the occluding edge 1312 and are received by the hinges 1321 located on the first body. Spring 1330 is located between the two bodies and held in position by a pair of spring receivers 1331 shown in FIGS. 49 and 50.

Figure 49:
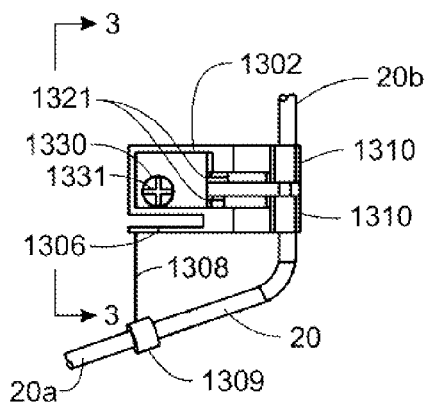
FIG. 49 is a top view of the first body of the embodiment shown in FIG. 47 as taken along line 1-1 of FIG. 48.
Figure 51:
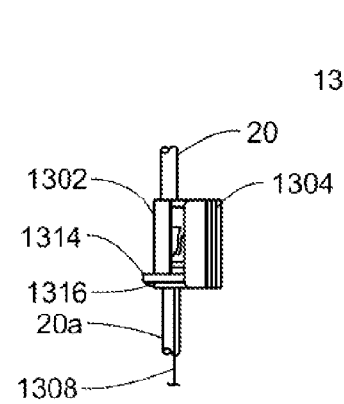
FIG. 51 is a side view of the embodiment along the line 3-3 of FIG. 48 with a flexible tube attached shown in an unoccluded position.
Figure 50:
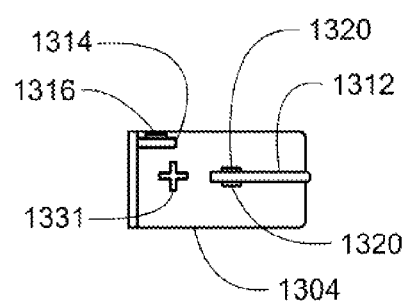
FIG. 50 is a bottom view of the second body of the embodiment shown in FIG. 47 as taken along line 2-2 of FIG. 48.

FIG. 49 is a top view of the first body 1302 with tube 20 taken along line 1-1 of FIG. 48. The clips 1310 hold the tube 20 in place while a force F (not shown) acts on the first end 20a of the tube 20. FIG. 50 is a section view of the underside of the second body 1304 taken along line 2-2 of FIG. 48. FIG. 51 is a side view of the embodiment 1300 taken along line 3-3 of FIG. 49 in an unoccluded state showing the spring 1330 in a fully compressed position. The tab 1316 holds the spring 1330 in compression until a force F acts upon the rod 1308 and then the tab 1316 releases the second body 1304 thus rotating the occluding edge 1312 into the tube 20. FIG. 52 is a section view of the embodiment 1300 taken along line 3-3 of FIG. 49 in an occluded state showing a force F acting on the rod 1308. The embodiment 1300 may be returned to the unoccluded state by removing the force F and reengaging the tab 1316 and the arm 1306.

Figure 54:
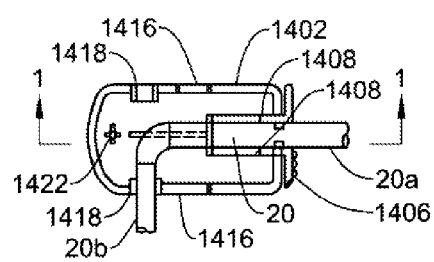
FIG. 54 is a top view of a base and trigger of the embodiment shown in FIG. 53 with a flexible tube attached.
Figure 53:
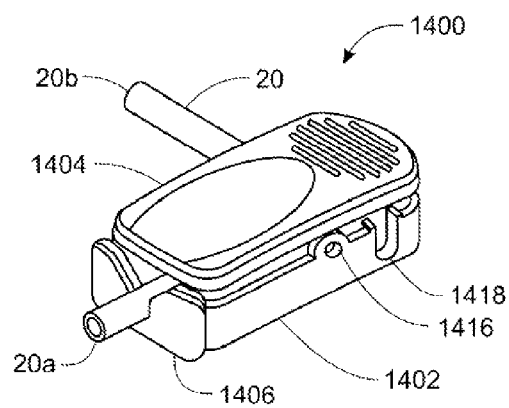
FIG. 53 is a perspective view of an embodiment of the invention with a flexible tube attached.

As shown in FIGS. 53 and 54, another embodiment 1400 of a device for occluding a flexible tube 20 generally comprises a base 1402 having a trigger 1406 slideably mounted along the longitudinal axis of the base 1402. A tube 20 is releasably coupled to the trigger 1406 along the longitudinal axis of the base 1402. The tube 20 is additionally coupled to the base 1402 at one of a pair of clips 1418 positioned on opposite sides of the base 1402. The clips secure the tube 20 to the base 1402 so that it does not move when the trigger is activated. A cover 1404 is pivotably attached to the base 1402 by means of a pair of hinges 1416 centrally located on opposite sides of the base 1402.

Figure 55:
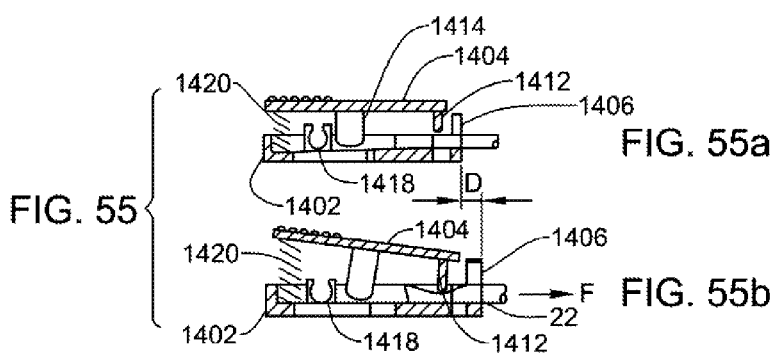
FIG. 55 is a cross-sectional view of the embodiment shown in FIG. 53 in the unoccluded position (FIG. 55a, top figure) and occluded position (FIG. 55b, bottom figure) taken along the line 1-1 of FIG. 54.

As shown in FIG. 55, an occluding edge 1412 rests upon the trigger 1406 when the trigger 1406 is fully inserted into the base 1402. However, when the trigger 1406 is moved outwardly and away from the base 1402 a distance D due to a threshold force F acting on a first end 20*a* of the tube, the occluding edge is urged onto the tube 20 by a spring 1420 with a compressive force sufficient to fully occlude the tube 20.

Figure 56:
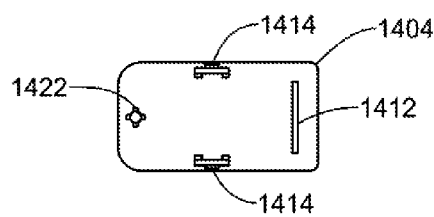
FIG. 56 is a bottom view of the cover of the embodiment shown in FIG. 53.

As shown in FIG. 56, the underside of the cover 1404 comprises an occluding edge 1412, a pair of tabs 1414 and a spring retainer 1422. The occluding edge 1412 is perpendicular to the longitudinal axis of the base 1402. The pair of tabs extends from the base and rotatably engage the pair of hinges 1416 on the base. The spring retainer 1422 is positioned on the opposite side of the tabs as the occluding edge and is configured to accept the spring 1420.

Figure 57:
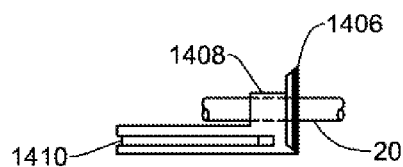
FIG. 57 is a side view of the trigger of the embodiment shown in FIG. 53.

As shown in FIG. 57, the trigger 1406 includes a channel 1410 which is slideably received by a pair of ridges on the base (not shown). Additionally, the top edge 1408 of the trigger is positioned so that the occluding member 1412 is not in contact with the tube 20 while the tube 20 is fully inserted into the base 1402.

Figure 58:
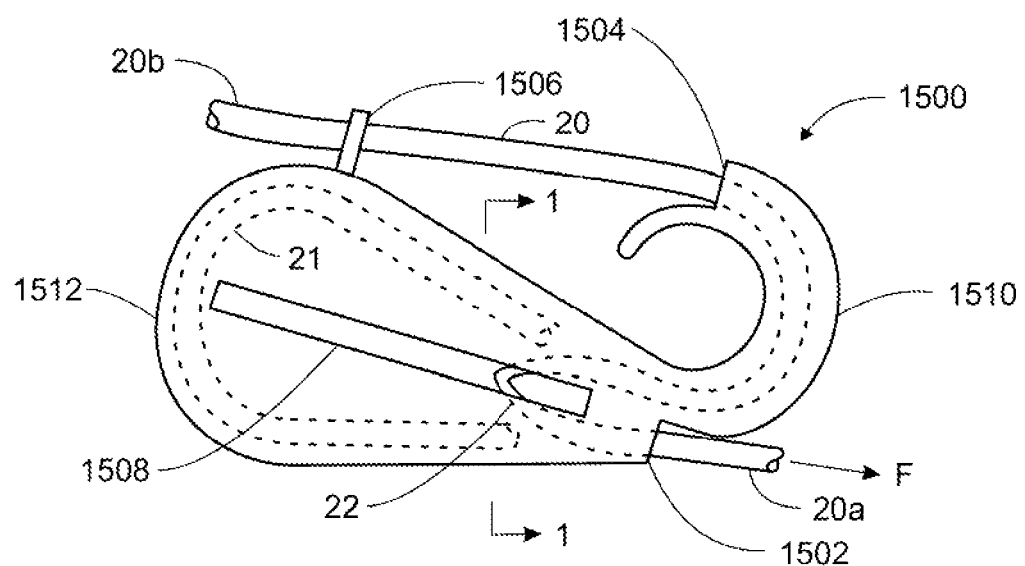
FIG. 58 is a top view of an embodiment of the invention with a flexible tube attached and shown in an unoccluded and occluded position.

As shown in FIG. 58, another embodiment 1500 of a device for occluding a flexible tube 20 generally comprises a curved hollow body having a first entrance 1502 and a second entrance 1504. The body has a first curved end 1510 and a second curved end 1512 which define the shape of the tube within the housing. A first section of tube 21 may freely move towards the first entrance 1502 when a first end 20*a* of the tube is moved outwardly and away from the first entrance 1502. When a threshold force F acts on the first end 20*a* and the tube 20 is deformed into a second position 22, whereby the tube 20 is fully occluded. A second end 20*b* is positioned by means of a clip 1506 extending outwardly and away from the second curved end 1512. Additionally, the tube 20 is frictionally held in place by the first curved end 1510 so that any force which acts on the second end 20*b* is resisted by the clip 1506 and the friction generated between the tube 20 and the first curved end 1510.

Figure 59:
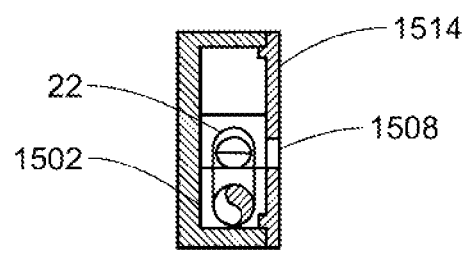
FIG. 59 is a cross-sectional view of the embodiment shown in FIG. 58 taken along the line 1-1 of FIG. 58 with a flexible tube in the occluded position.

FIG. 59 is a cross-sectional view of the embodiment 1500 taken along section line 1-1 of FIG. 58. A removable cover 1514 having a slot 1508 comprises one side of the embodiment for ease of access to the tube 20.

Figure 60:
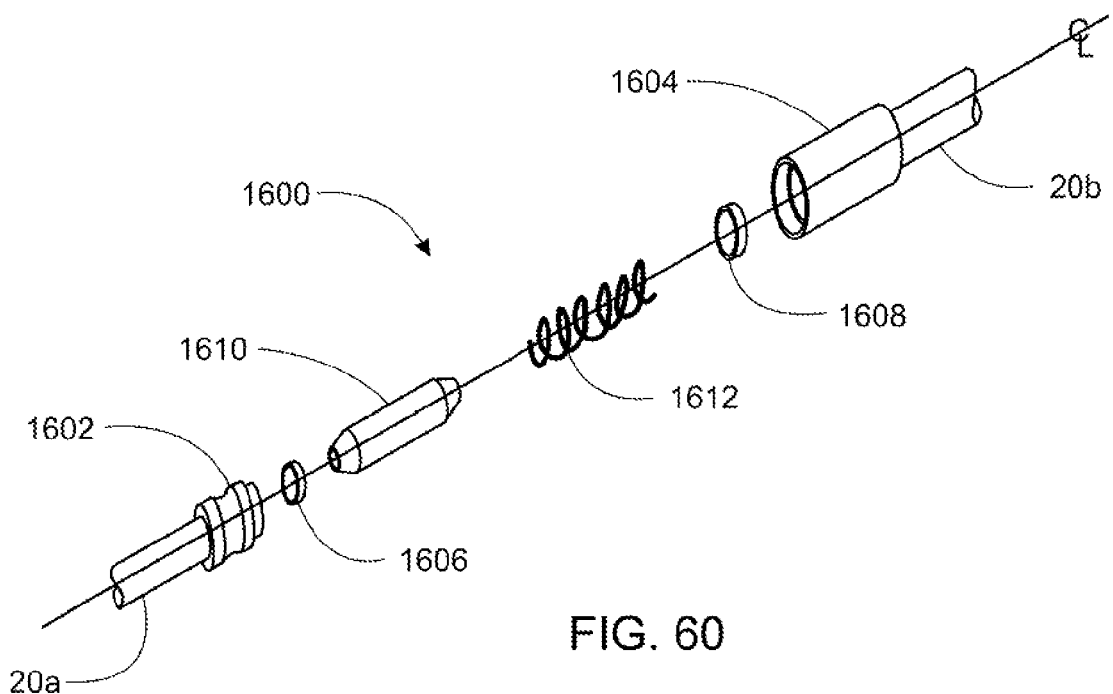
FIG. 60 is an exploded perspective view of an embodiment of the invention with a flexible tube attached.
Figure 61:
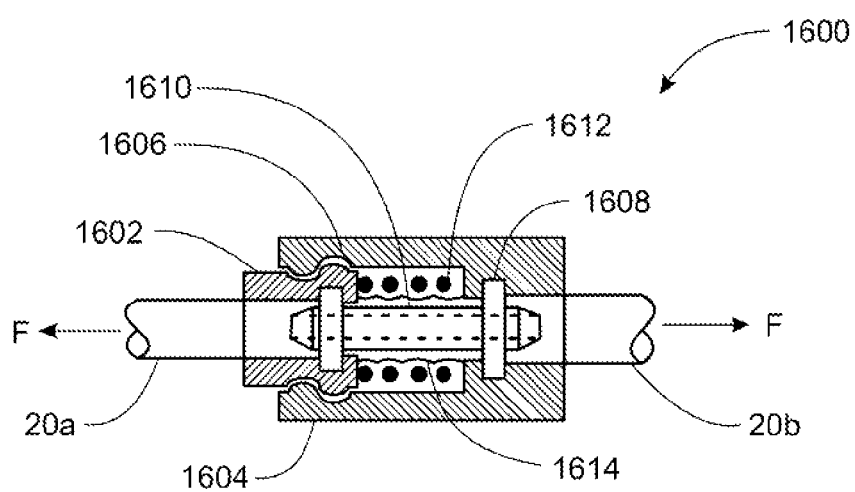
FIG. 61 is a cross-sectional view of the embodiment shown in FIG. 60 taken along the centerline with a flexible tube attached.

As shown in FIG. 60, another embodiment 1600 of a device for occluding a flexible tube 20 generally comprises a male coupling 1602 and a female coupling 1604. A first tube 20*a* may be secured to the male coupling 1602, while a second tube 20*b* may be secured to the female coupling 1604. A first valve 1606 having a watertight slit extending completely through is normally closed and positioned within the distal end of the male coupling 1602. A second valve 1608, also having a watertight slit, is normally closed and positioned inside the distal end of the female coupling 1604. The slits are configured to accept a hollow cylinder 1610, whereby a watertight seal is created between the exterior of the hollow cylinder 1610 and the interior of the slits when the cylinder 1610 is fully inserted into the slit. The male coupling 1602 is configured to lockingly engage the female coupling 1604. A tongue and groove assembly as shown in FIGS. 60 and 61 is just one means to lockingly engage the coupling. When the male and female coupling 1602, 1604 are fully engaged and locked, an internal spring 1612 is held in compression between the two couplings. Once coupled, the hollow cylinder 1610 creates a flow path through the first valve and second valve so that the first tube 20*a* and second tube 20*b* are in fluid communication with each other. When the hollow cylinder 1610 is removed from the slits, the valves are closed, and the distal ends of each tube 20 are sealed. Unlike the previously described embodiments, when this invention is triggered, the two halves, 1602 and 1604, completely separate. This terminates fluid flow and prevents further force from acting on the needle site.

As shown in FIG. 61, the spring 1612 is held in compression between the male and female couplings 1602, 1604 by a tongue and groove assembly at the distal ends of each coupling. The spring 1612 will urge the couplings apart from each other once the locking force between the tongue and groove assemblies is overcome by a threshold force F acting outwardly and away from the first and second tubes. The spring 1612 may be encapsulated in a tearable biocompatible material 1614 (i.e. a polyolefin) or its equivalent, whereby the spring 1612 does not come into direct contact with the fluid within the hollow cylinder 1610.

As shown in FIGS. 62, 63 and 64, another embodiment 1700 of a device for occluding a flexible tube generally comprises a female coupling 1702 and male coupling 1704 lockingly engaged to create a fluid connection between a first tube 20*a* and a second tube 20*b*. FIGS. 62, 63 and 64 show a cross-sectional view of the embodiment 1700 in different occluded positions. The female coupling 1702 generally comprises a first cylindrical body 1708 and second cylindrical body 1712 adapted to retain a one-way valve 1705 which is normally closed. A peripheral groove 1720 and a first gasket 1722 are located on the outer circumference of the second body. Both the groove 1720 and gasket 1722 are adapted to engage the male coupling 1704 and create a seal with the female coupling. The male coupling 1704 comprises a one-way valve 1705 and a hollow tapered body 1706, the body being capable of opening the one-way valves. A spring 1714 is compressed between the hollow tapered body 1706 and a third cylindrical body 1710. As the two couplings are brought together several sequential events occur within the embodiment: First, the hollow tapered body begins to engage the concave portions of the one-way valves 1705 as shown in FIG. 63. Then, the hollow tapered body compresses the spring 1714 against the third cylindrical body until the gasket 1724 has fully mated with the groove 1720. Finally, once mated, the hollow tapered body fully extends through the one way valves 1705, thus creating an unrestricted flow path for any fluid inside tubes 20*a* and 20*b*. An additional fluid seal is provided by the first gasket and the inside diameter of the third cylindrical body.

The patient and male coupling 1704 may be connected by means of a trigger wire 1718. The wire creates a separating force between the female coupling 1702 and male coupling 1704 when the threshold force F acts on the female coupling 1702 as shown in FIG. 63.

As shown in FIG. 62, during normal flow conditions, the trigger wire 1718 is slack and the male and female couplings 1704, 1702 are fully engaged. However, as shown in FIGS. 63 and 64, when a threshold force F acts on the female coupling 1702 through the first tube 20*a*, the couplings begin to separate from each other resulting in a cascade of events: First, the trigger wire 1718 becomes taught and a force F' is equally and oppositely applied to the male coupling 1704 though bracket 1716. Second, the groove 1720 and gasket 1724 disengage from each other. Next, the spring 1714 urges the couplings apart resulting in the withdrawal of the tapered body 1706 from both the one-way vales, thus ensuring that flow between tubes 20a and 20b is terminated. To unocclude the tubes, the force F must be removed from the tube 20a, and the couplings must be brought back into locking engagement as shown in FIG. 62.

Figure 65:
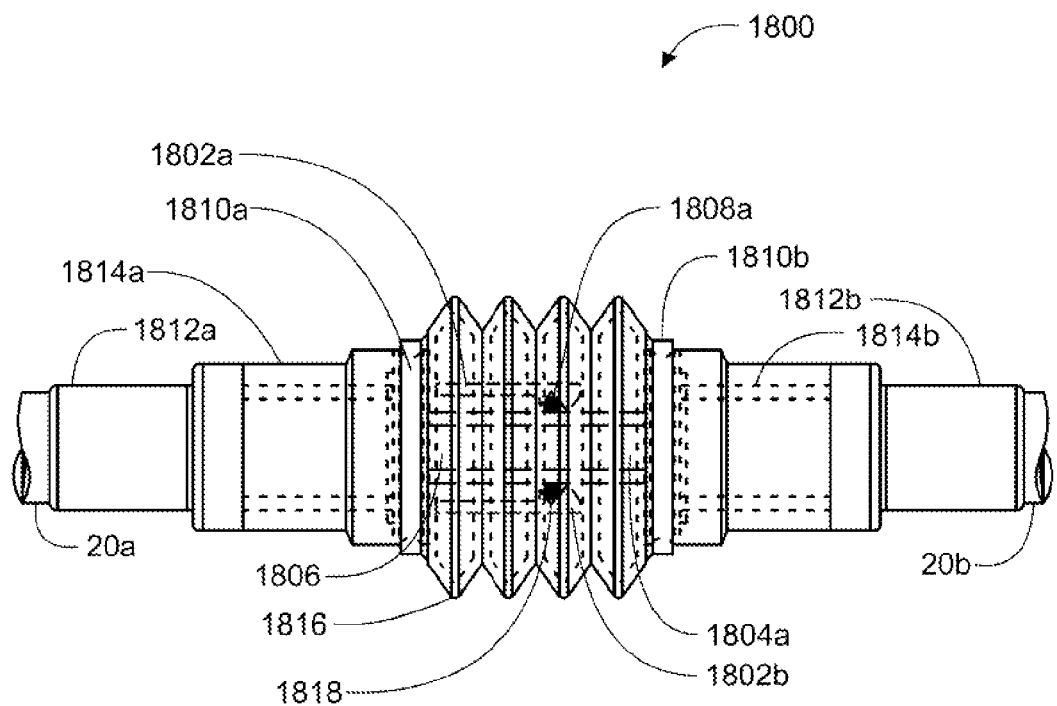
FIG. 65 is a side view of an embodiment of the invention in an unoccluded position with a flexible tube attached.
Figure 66:
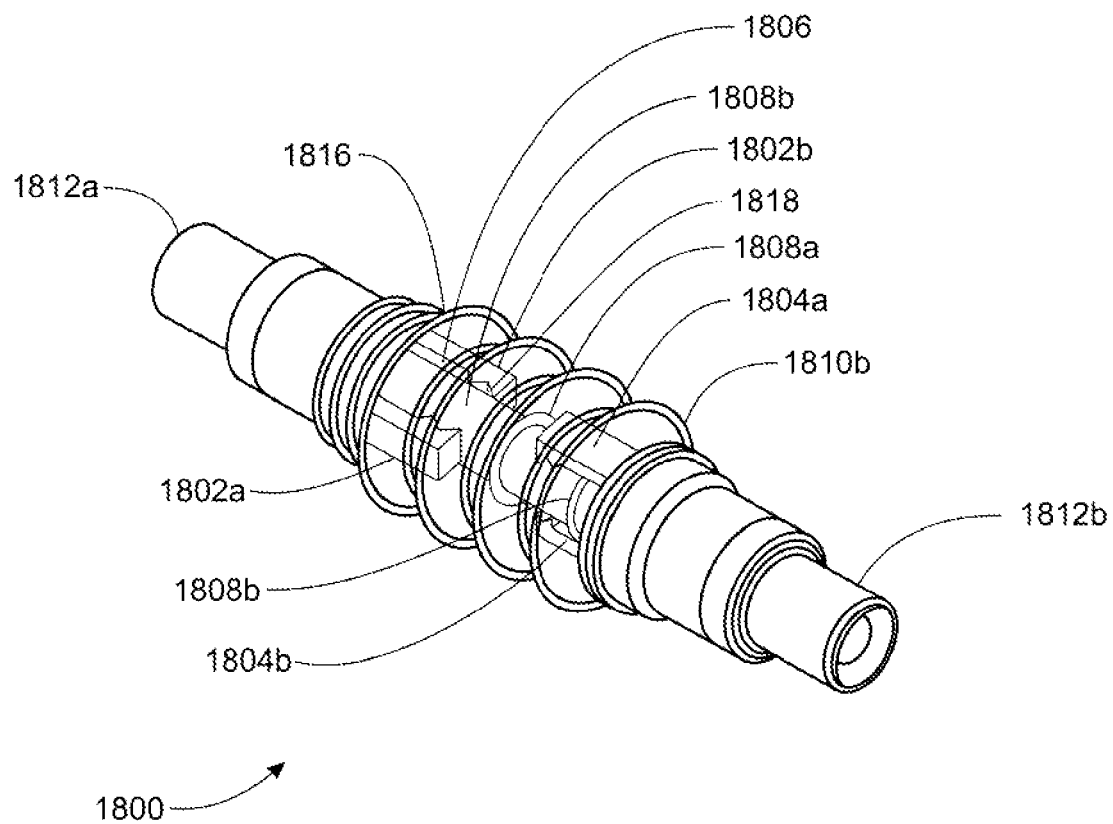
FIG. 66 is a perspective view of the embodiment of FIG. 65 in an occluded position.

As shown in FIGS. 65 and 66, another embodiment 1800 of a device for occluding a flexible tube generally comprises two one-way valve couplings 1814a,b (e.g. duckbill valves) located on either end of an interior channel 1806 lockingly engaged with two male couplings 1812a,b to create a fluid connection between a first tube 20a and a second tube 20b. Each coupling has a corresponding male/female portion of a duckbill valve disposed therein. In FIGS. 65 and 66, a portion of the housing is depicted as transparent so that connection between the duckbill valves 1814a, 1814b can be seen. Locking engagement is facilitated by a pair of latching arms 1802a,b attached to a base 1810a,b of each male valve coupling 1812a,b. Inner and outer rings 1808a,b (respectively) extend radially from the interior channel 1806 to engage with a detent 1818 on each latching arm 1802a,b.

Figure 68:
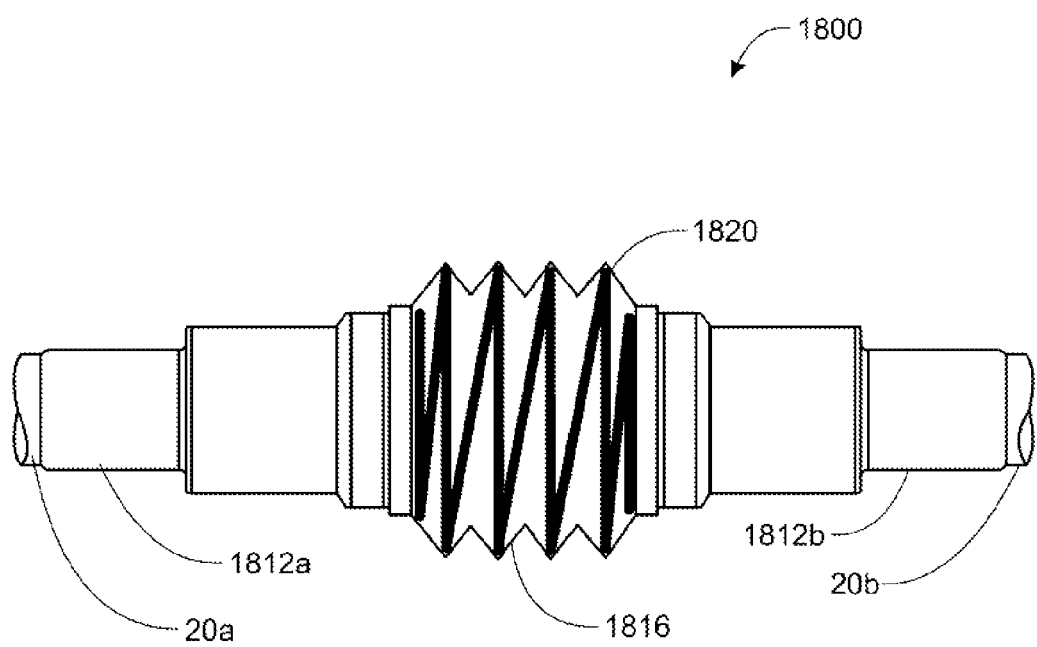
FIG. 68 is a side view of the embodiment of FIG. 65 in an unoccluded/compressed position with a flexible tube attached.

A bellows 1816 may surround the interior channel 1806 and engage with each base 1810a,b. The bellows 1816 defines an interior cavity of sufficient volume to allow the device to operate in multiple positions without unintended disengagement of the latching arms 1802a, 1802b from the rings 1808a,b. The bellows 1816 accommodates multiple positions by compressing and decompressing as the distance varies between each base 1810a,b. In various embodiments, as shown in FIG. 68 (detail omitted), the bellows 1816 may incorporate a spring 1820 to reduce the force required to disengage the latching arms 1802a, 1802b from the rings 1808a,b. The spring 1820 may be fully encapsulated within the bellows 1816 such that fluid flowing through the interior channel 1806 essentially runs through a central longitudinal axis of the spring 1820 in the first position.

In the preferred embodiment, there is one inner ring 1808a and two outer rings 1808b to facilitate multiple positions in which fluid flow may be permitted or terminated. In a first position, as shown in FIG. 65, the detent 1818 on each pair of latching arms 1802a, 1802b is engaged with the inner ring 1808a. The latching arms 1802a, 1802b are opposite each other to accommodate simultaneous attachment to the inner ring 1808a. As a result of this configuration, the male valve couplings 1812a,b are engaged with the female valve couplings 1814a,b such that fluid can freely flow through the interior channel 1806 via penetrated duckbill valves. Each base 1810a,b can provide an additional fluid seal with the use of o-rings (not shown).

Figure 67:
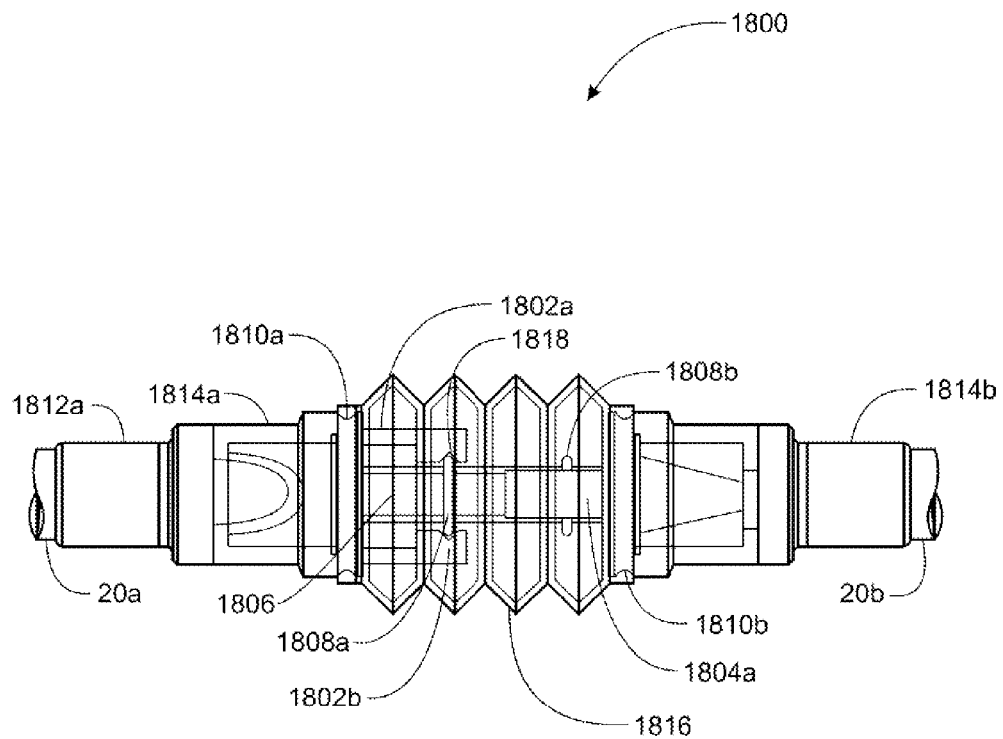
FIG. 67 is a side view of the embodiment of FIG. 65 in an occluded position with a flexible tube attached.

In a second position, as shown in FIG. 67, one pair of latching arms 1804 is disengaged from the inner ring 1808a which disengages the corresponding duckbill valve portions. As a result, one duckbill valve is unpenetrated and fluid is prevented from flowing through the interior channel 1806. In a third position, as shown in FIG. 66, each pair of latching arms 1802a, 1802b is disengaged from the inner ring 1808a but remain engaged with the outer ring 1808b. As a result, fluid flow into the interior channel 1806 is terminated as both duckbill valves are in an unpenetrated state. Positions two and three may be the result of a force acting on one or both ends of the tube 20. Additionally, a force triggering disengagement of latching arms 1802, 1804 from their respective rings may allow the spring 1820 to further urge the housing sections 1812a,b in opposite directions, thereby transitioning the device 1800 out of the first position. If a substantial force acts on one or both ends of the tubing 20, the device may completely separate, terminating fluid flow indefinitely.

As shown in FIGS. 69-76, another embodiment 1900 of a device for occluding a flexible tube generally comprises a movable housing 1904 capable of sliding over a pair of arms 1906a,b and occluding the tube 20. As shown in FIG. 69 and FIG. 70, a spring 1908 disposed between the fixed housing 1902 and movable housing 1904 has a potential energy that tends to urge the movable housing 1904 away from the fixed housing 1902 but for the trigger 1914, which holds the device in an unoccluded state. The trigger 1914, best viewed in FIGS. 70, 71 and 75, interacts with the movable housing 1904 on both sides of the arms 1906a,b. The trigger 1914 is essentially part of a flexible coupling 1912 attached to the fixed housing 1902 at one end and the tube 20 at the other end. This flexible configuration allows the trigger 1914 to move inwardly in response to pulling or stretching force exerted on the tube 20, thereby disengaging the trigger 1914 from movable housing 1904 and releasing the potential energy in the spring 1908.

Figure 74:
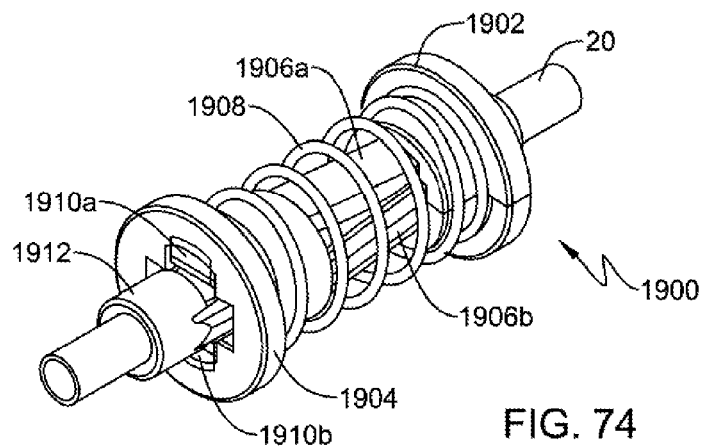
FIG. 74 is a perspective view of the embodiment shown in FIG. 69 in an occluded position with a flexible tube attached.
Figure 72:
FIG. 72 is a side view of the embodiment shown in FIG. 69 in an occluded position with a flexible tube attached.
Figure 73:
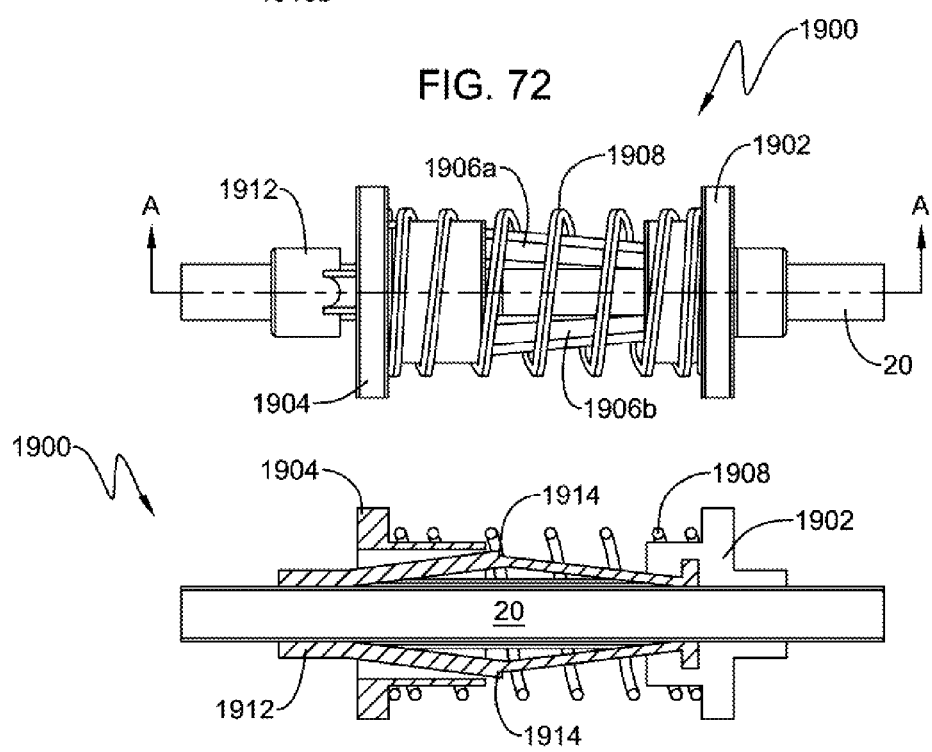
FIG. 73 is a cross-sectional view of the embodiment shown in FIG. 72 taken along the line A-A.
Figure 78:
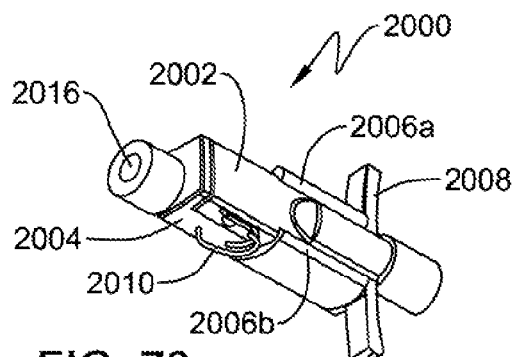
FIG. 78 is a perspective view of the embodiment shown in FIGS. 77 and 79 in an unoccluded position.

In the unoccluded state, the arms 1906a,b generally diverge from the longitudinal axis of the tube 20. Thus, occluding members 1910a,b, located at the distal ends of the arms 1906a,b, are held away from the tube 20 such that fluid may freely flow through the device 1900. In a occluded state, as shown in FIGS. 73 and 74, the occluding members 1910a,b pinch and terminate flow within the tube 20 as potential energy from the spring 1908 is released and the sliding action of the movable housing 1904 forces the arms 1906a,b together. The device may be returned to an unoccluded state by forcing the housing sections 1902, 1904 together such that the trigger 1914 is reset.

Figure 77:
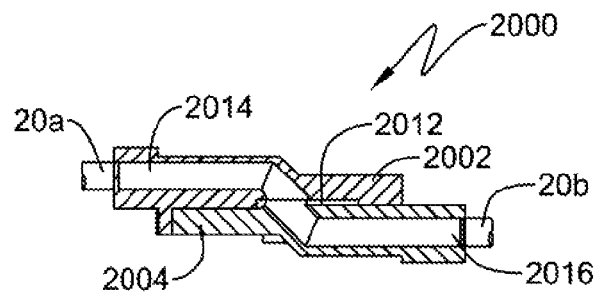
FIG. 77 is a cross-sectional view of an embodiment shown in FIG. 79 taken along the line A-A.
Figure 79:
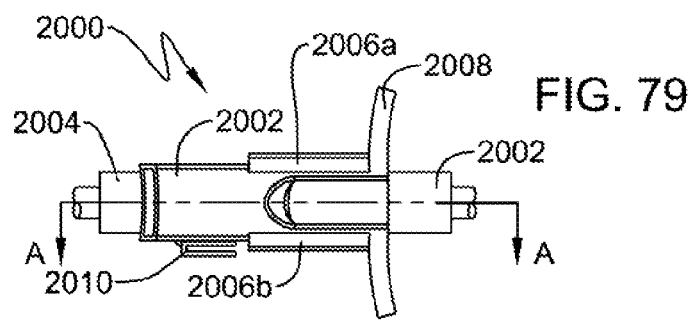
FIG. 79 is a top view of the embodiment shown in FIG. 78 in an unoccluded position with a flexible tube attached.
Figure 80:
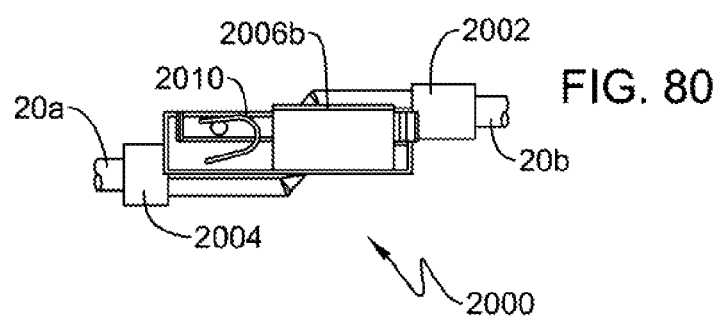
FIG. 80 is a side view of the embodiment shown in FIG. 78 in an unoccluded position with a flexible tube attached.
Figure 82:
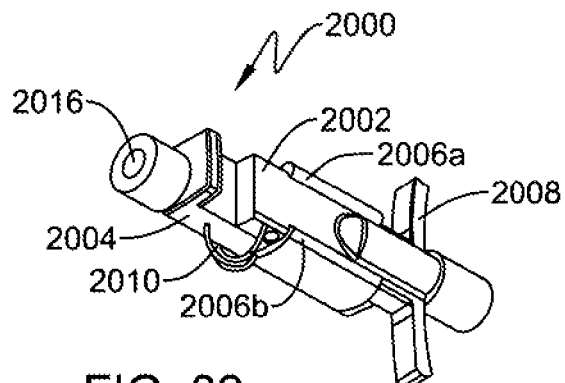
FIG. 82 is a perspective view of the embodiment shown in FIGS. 81 and 83 in an occluded position.
Figure 81:
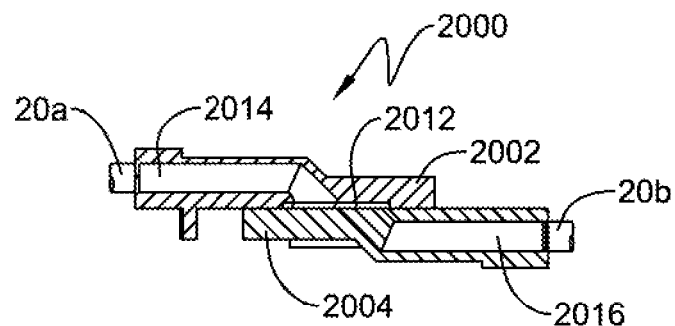
FIG. 81 is a side view of the embodiment shown in FIG. 83 taken along the line A-A.
Figure 83:
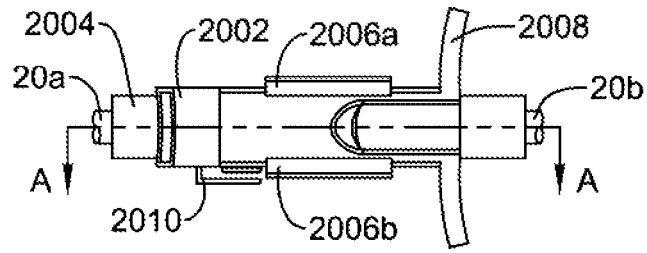
FIG. 83 is a top view of the embodiment shown in FIG. 82 in an occluded position with a flexible tube attached.
Figure 84:
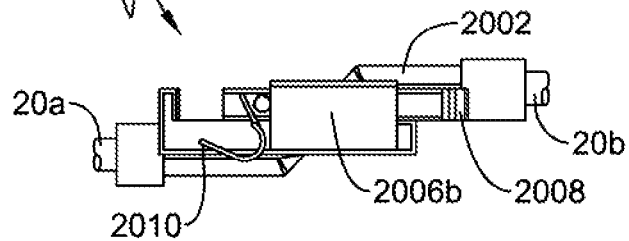
FIG. 84 is a side view of the embodiment shown in FIG. 82 in an occluded position with a flexible tube attached.

As shown in FIGS. 77-84, another embodiment 2000 of a device for occluding a flexible tube generally comprises a first channel 2014 and a second channel 2016 slideably coupled and capable of linearly disengaging in response to a force on the tube 20. As shown in FIG. 77, a first housing 2002 defines a first channel 2014 to accept one end of a flexible tube 20a. The first channel 2014 directs fluid into a second channel 2016, within a second housing 2004, via a sealable interface 2012. The sealable interface 2012 may be an elastic material, such as medical grade silicone, to prevent fluid from seeping though the device 2000 in sliding and disengaged positions. In the preferred embodiment, the sealable interface 2012 is embedded in the first housing 2002, however, in other various embodiments, both housing sections may incorporate a sealable interface. Housing sections 2002, 2004 are slideably joined via two hooked portions 2006a,b protruding from the second housing 2004. A spring 2010, located between housing sections 2002, 2004 provides the force necessary to disengage the channels 2014, 2016 in response to a force applied to either end of the tube 20.

In an unoccluded position, as shown in FIGS. 77-80, fluid may flow through the device 2000 as the channels 2014, 2016 are aligned. The compressed spring 2010 is designed using a cam-over-center methodology such that it applies a force on the housing sections 2002, 2004 which essentially holds the device 2000 together. In the event that either of the housing sections 2002, 2004 begin to slideably disengage, i.e., an axially applied force on the tube 20, the curved nature of the spring 2010 allows it to rotate and decompress. As the spring 2010 decompresses the housing sections 2002, 2004 are urged farther apart, forcing the device 2000 into an occluded position.

In the occluded position, as shown in FIGS. 81-84, the spring 2010 remains partially decompressed such that a constant force acting on the housing sections 2002, 2004 holds the channels 2014, 2016 in misalignment. The channels 2014, 2016 are occluded as the sealable interface 2012 prevents fluid from leaking out of the device 2000. Arms 2008 attached to the first housing 2002 may provide a means of returning the device 2000 to the unoccluded position, allowing the spring 2010 to be repositioned to an over-center compressed state.

In another aspect, the invention comprises an occluder assembly that surrounds a section of flexible tubing, and that derives its occluding force from a spring-loaded actuator, the spring acting longitudinally in line with the flexible tubing. A pre-determined threshold amount of tension (generated by a pulling force estimated to threaten the risk of dislodgement of an intravenous catheter) applied to the section of tubing causes a specified amount of stretching (if there is no slack) or movement (if there is slack) of the tubing, which in turn causes a releasing member to trigger the spring-loaded actuator. The actuator can then interact with an occluder to convert the longitudinal spring force into a transverse occluding force against the tubing, occluding or constricting its lumen. The assembly can include a releasing member, an occluder, an actuator, a spring and a spring housing. At least a part of the releasing member is attached to the tubing, so that stretching or movement of the tubing results in translational movement of the releasing member longitudinally along the section of tubing. Movement of the releasing member triggers release of the spring-loaded actuator. The releasing member can be in direct contact with the actuator or a spring retention element in order to trigger release of the actuator, or it can act indirectly through contact with the occluder, which in turn can be in contact with the actuator or a spring retention element. Once released, the actuator, under the force of the compressed spring, can travel longitudinally along the flexible tubing and press the occluder against the flexible tubing, occluding or constricting its lumen.

In an embodiment, the occluder can serve as an intermediary structure between the releasing member and the actuator. For example, when the assembly is in an armed state, the releasing member is engaged with the occluder to immobilize it. In addition, another portion of the occluder can hold the actuator in an armed position, the actuator being under the force a compressed spring within a spring housing. The releasing member can respond to a pre-determined threshold amount of pulling force on the tubing by moving longitudinally along with the affected segment of tubing and disengaging from the occluder, which in turn can release the actuator to press the occluder against the tubing under the force of the actuator spring.

Figure 85:
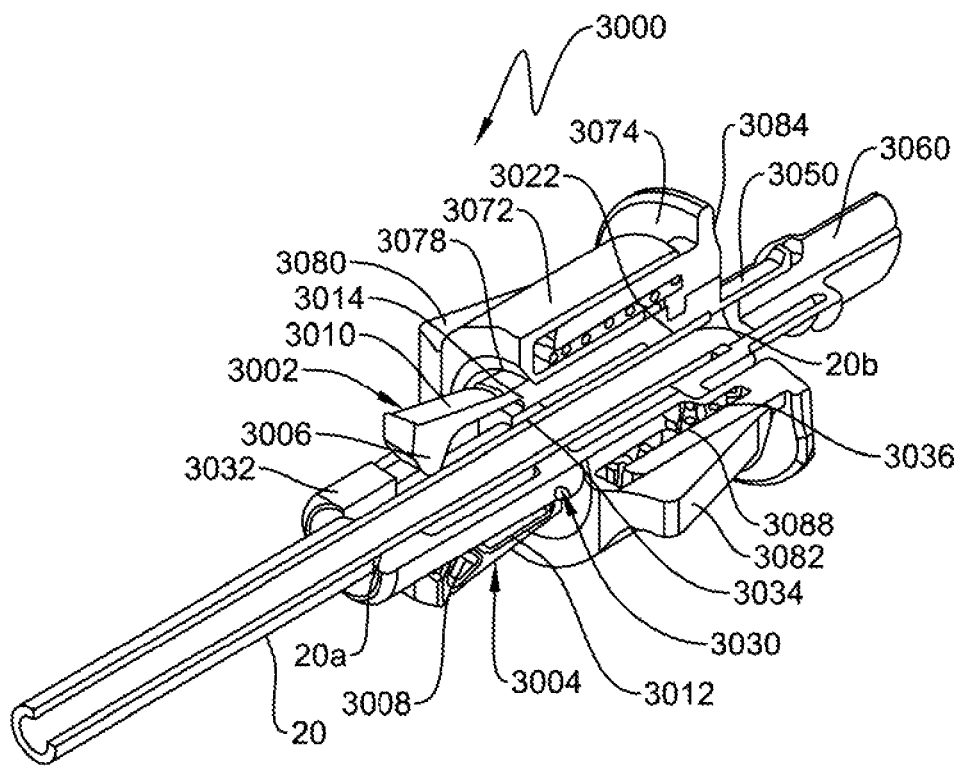
FIG. 85 is a partial cutaway view of an embodiment of the invention in an unoccluded position with a flexible tube attached.

FIG. 85 shows a partial cutaway view of an embodiment of the invention incorporating a longitudinally acting spring-loaded actuator. In the embodiment shown in FIGS. 85-87, the occluder assembly 3000 is positioned along a length of flexible tubing 20. The tubing section can either be incorporated into an otherwise standard vascular catheter (e.g., a hemodialysis or central venous catheter), or can be connectable on both ends to any other flexible tubing via a coupling (e.g., such as a Luer lock coupling). In the illustrated embodiment, a Luer lock coupling 3050 is shown at one end of the assembly, capped by cap 3060. An occluder 3002 is positioned so that an arm 3010 of occluder 3002 includes occluding element 3006. A first section 3032 of releaser 3030 is attached to a first section 20a of flexible tubing 20. A second section of releaser 3030 includes a contact element 3034 for contacting a corresponding contact element 3014 of occluder 3002. In the illustrated embodiment, releaser contact element 3034 is frictionally wedged with occluder contact element 3014, keeping arm 3010 of occluder 3002 slightly raised and relatively immobile, preventing deflection of occluder 3002 toward tubing 20.

At least a portion of occluder 3002 is attached to a second section 20b of flexible tubing 20. In the illustrated embodiment in FIG. 85, for example, a section 3022 of occluder 3002 is attached (e.g., by adhesive, ultrasonic welding, or other means) to the second section 20b of tubing 20. An actuator assembly 3070 (see FIG. 86) can be mounted over an elongate section 3026 of occluder 3002. In the illustrated embodiment, actuator assembly 3070 includes actuator 3072, spring housing 3074, and spring 3076. At least a portion of actuator assembly 3070 (such as, for example the spring housing 3074) can be permanently fixed to a second section 20b of tubing 20 or to section 3022 of occluder 3002; or it can be releasably mounted to section 3022 of occluder 3002 (allowing for potential re-use of actuator assembly 3070). In an armed position, actuator 3072 is slideably mounted on spring housing 3074, compressing spring 3076 situated within spring housing 3074. A stop 3018 formed on the outer side of occluder 3002 makes contact with a leading edge 3078 of actuator 3072.

In the armed state, contact between releaser contact element 3034 and occluder contact element 3014 positions occluder arm 3010 away from tubing 20, and positions occluder stop 3018 against leading edge 3078 of actuator 3072. In this armed position, occluder stop 3018 prevents actuator 3072 from being released by compressed spring 3076.

Figure 87:
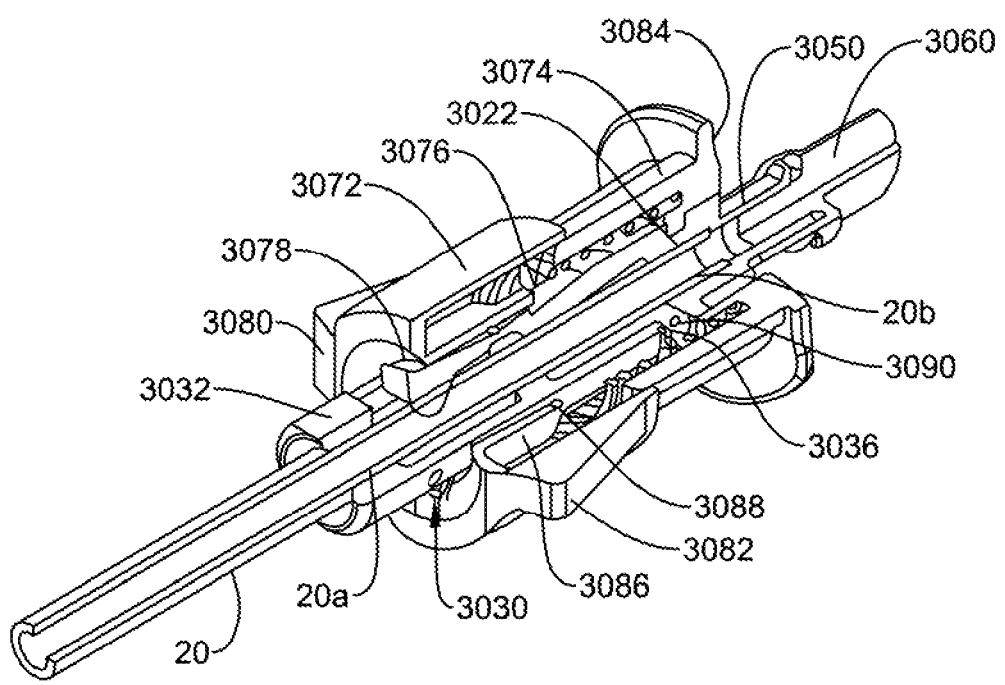
FIG. 87 is a partial cutaway view of the embodiment of FIG. 85 in an occluded position with a flexible tube attached.

When sufficient pulling force is applied longitudinally to tubing 20, either from the first end 20a or the second end 20b, a longitudinal force tending to separate releaser 3030 from occluder 3002 is generated. Once a pre-determined threshold traction force is reached, the resistance to separation of releaser contact element 3034 from occluder contact element 3014 is overcome, and occluder arm 3010 is free to move inwardly toward tubing 20. Upon movement of occluder arm 3010 occluder stop 3018 disengages from leading edge 3078 of actuator 3072, releasing actuator 3072 to slide longitudinally along occluder arm 3010, as shown in FIG. 87. Under the longitudinal force provided by spring 3076, actuator 3072 slides along occluder arm 3010, pressing occluder element 3006 against the side wall of tubing 20, thereby occluding or constricting its lumen.

In the illustrated embodiment, the amount of traction force needed to cause release of actuator 3072 can be changed by altering the holding characteristics between releaser contact element 3034 and occluder contact element 3014. The two contact elements 3034 and 3014 are wedge shaped, and their holding characteristics can be varied by changing the smoothness and composition of the mating surfaces, as well as the angle at which the surfaces wedge together. In addition, altering the lengths of engagement between the contact elements can also vary the holding characteristics, and thus the threshold amount of pulling force that must be applied to the tubing to trigger release of the device and occlusion of the tubing. More generally, contact elements whose interaction is designed to trigger a spring-loaded actuator can take many forms. Another non-limiting embodiment of contact elements can include, for example, a tooth and groove arrangement, in which the shape of the tooth element or the shape and depth of the groove element can be varied to alter the holding characteristics of the elements, and thus the force required to separate them. In other embodiments, it is also possible that the contact elements could be constructed to trigger an actuator by making contact with one another (rather than separating) upon the pulling of an attached flexible tubing segment.

Figure 86:
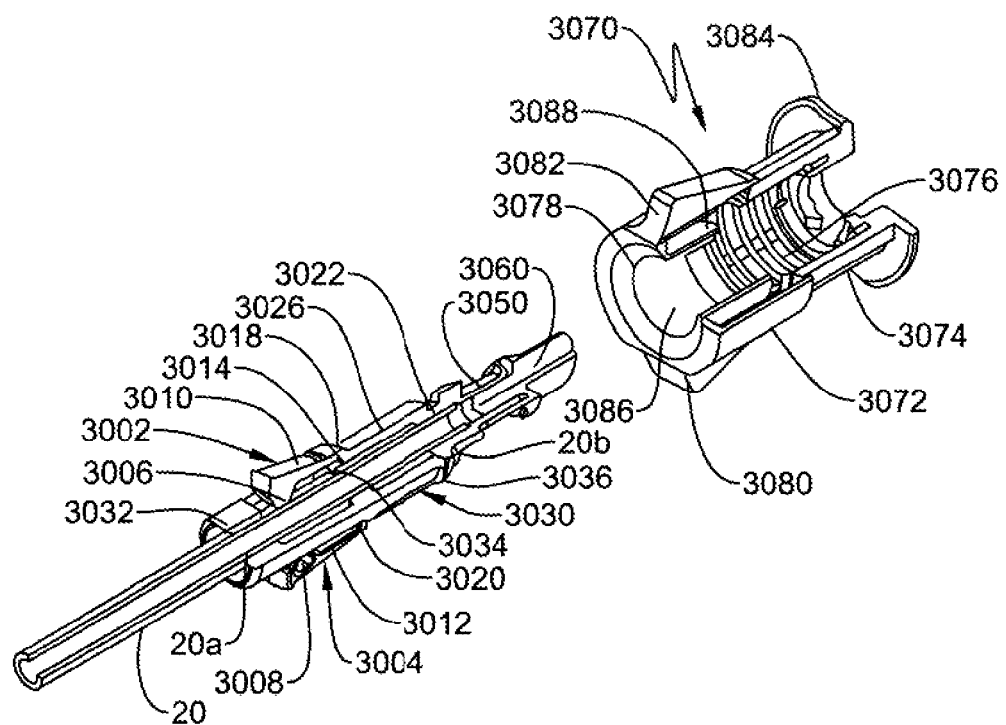
FIG. 86 is a partial cutaway view of the embodiment of FIG. 85, with the actuator assembly separated from the occluder.

Although the embodiment shown in FIGS. 85-87 is equipped with two opposing occluder arms 3010 and 3012 and occluder elements 3006 and 3008, a similar occluding mechanism can be applied to a single occluder arm or three or more occluder arms positioned around the circumference of tubing 20. With any of these embodiments, the longitudinal force applied by the spring can be converted to an approximately transverse force acting on the flexible tubing by an actuator such as actuator 3072 interacting with an occluder such as occluder 3002. In this example, the actuator is driven by the spring so that the inside surface of the actuator slides along the surface of one or a plurality of occluders, compressing them against the tubing.

The occluder assembly 3000 illustrated in FIGS. 85-87 can be re-armed after the pulling force on tubing 20 has been relieved. Finger holds 3080 and 3082 can be grasped by two fingers with the thumb positioned behind the base 3084 of spring housing 3074, and actuator 3072 can then be retracted back to its armed position, as shown in FIG. 85. With tubing 20 in a relaxed state, the releaser contact element 3034 can return to a wedged relationship with occluder contact element 3014, allowing occluder stop 3018 to once again hold actuator 3072 in its armed position.

Should the elasticity of tubing 20 be insufficient to cause a suitable re-engagement of the releaser contact element with its opposing contact element, actuator 3072 can be designed to pull the releaser contact element into proper re-engagement, as the actuator itself is being pulled by the user into an armed position. An example of this is shown in FIG. 86, in which a section of releaser 3030 can include a jog feature 3036 that can be captured by the trailing edge 3088 of actuator slide guide 3086, as it is retracted to an armed position. Retracting releaser 3030 a distance equal to gap 3090 provides the correct distance required to fully re-engage releaser contact element 3034 with occluder contact element 3014.

Figure 88:
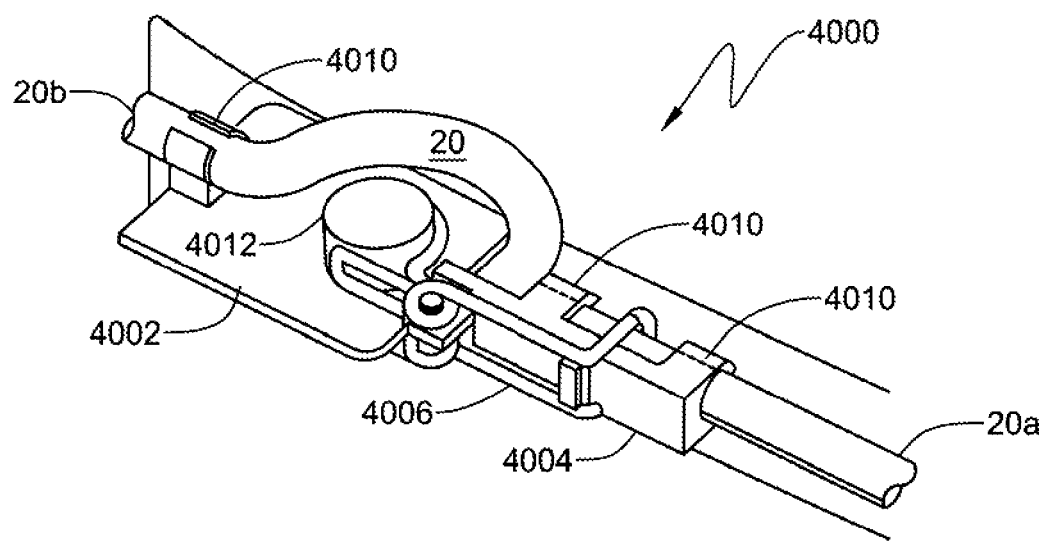
FIG. 88 is a perspective view of an embodiment of the invention in an unoccluded position with a flexible tube attached.
Figure 89:
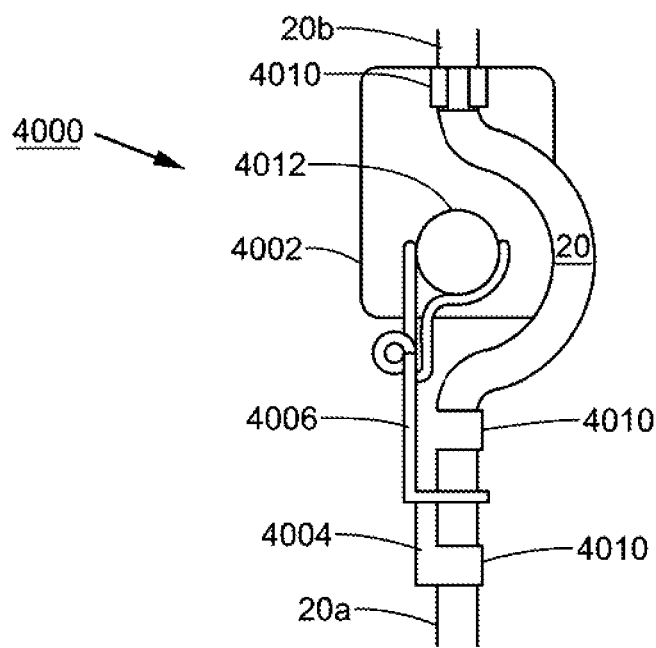
FIG. 89 is a top view of the embodiment of FIG. 88 in an unoccluded position with a flexible tube attached.

In another embodiment, as shown in FIGS. 88 and 89, an embodiment 4000 of a device for occluding a flexible tube generally comprises a first body 4002 frictionally connected to a second body 4004 by a spring-loaded clip 4006. A flexible tube 20 having a first end 20a and a second end 20b is secured to each body by a plurality of clamps 4010. When the two bodies are separated by a predetermined threshold force F (not shown) acting axially on either the first end or second end of the tube 20 so as to cause the bent section of tubing 20 to straighten, the spring-load clip 4006 occludes the tube 20 secured by the second body. More specifically, the spring-loaded clip 4006 lockingly engages a cylindrical hub 4012 located on the first body 4002. The clip 4006 generates enough compressive force to hold the bodies 4002 and 4004 together with a frictional force that is less than the predetermined force F acts on the flexible tube 20. The clip 4006 slides off the hub 4012 and triggers the occlusion when the two bodies are pulled apart from each other by the predetermined force F.

In other embodiments, a visual or auditory alarm can be included in the occluder assembly. Actuator motion during release can serve to trigger an electrical switch of a battery-operated alarm attached to or included on the occluder assembly. For example, a Hall sensor or mechanical switch can be used to detect release of the actuator, which can then activate a piezo buzzer or light emitting diode ("LED") light attached to the unit. The local alarm could be useful in extracorporeal blood flow systems such as hemodialysis or hemoperfusion systems, for example. The auditory or visual alarm could serve to alert the user of the tubing occlusion before a pressure sensor in a hemodialysis apparatus would trigger a shut-down of the hemodialysis pump. In the case of a pulling force that does not lead to dislodgement of the intravenous catheter, the user would thus have the opportunity to relieve tension on the flexible tubing and re-arm the occluder assembly before treatment (i.e. blood pumping) is automatically interrupted. An LED light can also be used to indicate to the user that the device is properly armed.

In yet other embodiments, the occluding assemblies described above, (such as, e.g., those utilizing a longitudinally acting spring force) can have two channels situated side-by-side to accommodate both an arterial and a venous line when these lines are used separately in an extracorporeal blood flow circuit. Each line can have a dedicated occluding member that can pinch each line against a common wall or septum separating the two lines in the device. Both occluding members can be pressed against their respective lines by the same actuator, as described above for occluding assemblies 100 and 3000. Thus any potential dislodgement of an intravenous catheter associated with one of the lines will automatically trigger occlusion of both lines, helping to avoid the risk of air being drawn into the patient's circulation via the remaining intact intravenous catheter.

The invention described herein need not be limited to flexible tubing used for intravenous infusion. It can also be applied, for example to medical tubing used in non-IV applications, such as tubes leading to the peritoneal cavity, the stomach, the bladder, or any other hollow organ. In addition, the invention can also be applied in circumstances in which it is desirable to stop the flow of a fluid into any dependent container once the container accumulates a specified amount of fluid and reaches a threshold weight. Furthermore, the invention can be applied to circumstances—whether medical or non-medical—in which it is desirable to stop the flow of fluid in a flexible tube if excessive tension is applied to the tubing. It can also be appreciated that a flexible tube having tensile properties can contract upon release of a distracting force. Thus, the invention described herein can also be constructed to trigger from a non-occlusive to an occlusive state, or conversely from an occlusive to a non-occlusive state, if a flexible tube held under longitudinal tension is released and allowed to relax back into its pre-tension length. A change in length in either direction can be exploited to cause the occluding device to release.

The invention claimed is:

1. A device for occluding a flexible tube comprising:
    a first body for holding a first section of the flexible tube;
    a second body defining a space for holding a second section of the flexible tube, the second body frictionally connected to and separable from the first body by a spring-loaded member mounted to the second body;
    the spring loaded member having a first end configured to engage an element of the first body by applying a spring force against the element, biasing a second end of the spring loaded member into a retracted position adjacent the space defined by the second body;
    the second end of the spring loaded member being induced to move into the space defined by the second body when the first end of the spring loaded member is disengaged from the element of the first body;
    the first and second bodies configured to hold the flexible tube on the device so that the flexible tube extends away from the device in a longitudinal direction and is immobilized in a longitudinally bent position on the device;
    wherein the spring loaded member is configured so that the spring force holding the first end of the spring loaded member on the element of the first body is overcome by a pre-determined amount of pulling force applied to the flexible tube along the longitudinal direction when mounted on the device, causing the second body to separate from the first body, and the second end of the spring loaded member to encroach the space defined by the second body.

2. The device of claim 1, wherein the spring loaded member is a spring-loaded clip.

3. The device of claim 2, wherein the element of the first body is a post, and the spring-loaded clip is configured to engage the post.

4. The device of claim 3, wherein the post is a cylindrical hub.

5. The device of claim 1, wherein the flexible tube is held in position on the first and second bodies by two or more clamps.

6. The device of claim 1, wherein the pulling force is applied on the first section of the flexible tube or the second section of the flexible tube.

7. The device of claim 1, wherein the pulling force is sufficient to begin straightening the bent position of the flexible tube.

8. The device of claim 1, wherein the predetermined pulling force is sufficient to cause the first end of the spring-loaded member to slide off the element of the first body.

9. The device of claim 1, wherein the first and second bodies continue to hold the flexible tube after the first and second bodies are separated.

* * * * *